United States Patent
Schnieders et al.

(10) Patent No.: US 12,133,898 B2
(45) Date of Patent: Nov. 5, 2024

(54) IMMUNOSTIMULATING VECTOR SYSTEM

(71) Applicant: Provecs Medical GmbH, Hamburg (DE)

(72) Inventors: Frank Schnieders, Hamburg (DE); Andrea Miegel, Hamburg (DE); Carolin Biermann-Fleischhauer, Ahrensburg (DE)

(73) Assignee: PROVECS MEDICAL GMBH, Hamburg (DE)

( * ) Notice: Subject to any disclaimer, the term of this patent is extended or adjusted under 35 U.S.C. 154(b) by 397 days.

(21) Appl. No.: 17/220,578

(22) Filed: Apr. 1, 2021

(65) Prior Publication Data

US 2021/0220486 A1  Jul. 22, 2021

Related U.S. Application Data

(62) Division of application No. 16/079,331, filed as application No. PCT/EP2017/054216 on Feb. 23, 2017, now Pat. No. 10,994,027.

(30) Foreign Application Priority Data

Feb. 25, 2016 (EP) .................................... 16157423

(51) Int. Cl.
| | | |
|---|---|---|
| *A61K 48/00* | (2006.01) | |
| *A61K 31/70* | (2006.01) | |
| *A61P 31/12* | (2006.01) | |
| *A61P 35/00* | (2006.01) | |
| *C07H 21/04* | (2006.01) | |
| *C07K 14/54* | (2006.01) | |
| *C07K 14/55* | (2006.01) | |
| *C07K 14/705* | (2006.01) | |
| *C12N 15/86* | (2006.01) | |
| *A01K 67/00* | (2006.01) | |

(52) U.S. Cl.
CPC ...... *A61K 48/0066* (2013.01); *A61K 48/0016* (2013.01); *A61K 48/0075* (2013.01); *A61K 48/0083* (2013.01); *A61K 48/0091* (2013.01); *A61P 31/12* (2018.01); *A61P 35/00* (2018.01); *C07K 14/5434* (2013.01); *C07K 14/55* (2013.01); *C07K 14/70532* (2013.01); *C07K 14/70575* (2013.01); *C12N 15/86* (2013.01); *C12N 2710/10043* (2013.01); *C12N 2840/203* (2013.01); *C12N 2840/206* (2013.01)

(58) Field of Classification Search
CPC ............ A61K 48/0066; A61K 48/0016; A61K 48/0075; A61K 48/0083; C12N 15/86; C12N 2840/203; C12N 2840/206; C12N 2710/10043
See application file for complete search history.

(56) References Cited

U.S. PATENT DOCUMENTS

| | | |
|---|---|---|
| 5,082,658 A | 1/1992 | Palladino |
| 5,994,104 A | 11/1999 | Anderson et al. |
| 6,034,072 A | 3/2000 | Ralston et al. |
| 6,475,999 B1 * | 11/2002 | Mastrangelo et al. |
| 8,067,227 B2 | 11/2011 | Waehler et al. |
| 8,900,858 B2 | 12/2014 | Trono et al. |
| 2004/0209363 A1 | 10/2004 | Watts et al. |
| 2006/0153805 A1 | 7/2006 | Waelhler et al. |
| 2012/0301919 A1 | 11/2012 | Yang et al. |

FOREIGN PATENT DOCUMENTS

| | | |
|---|---|---|
| WO | WO 2004/035799 A2 | 4/2004 |
| WO | WO 2004/036799 A2 | 4/2004 |

OTHER PUBLICATIONS

Chen et al. Evaluation of cytokine toxicity induced by vaccinia virus-mediated IL-2 and IL-12 anti-tumor immunotherapy. Cytokine 15:305-314, (Year: 2001).*
Das et al. Gene therapies for Cancer: Strategies, Challenges and Successes. J. Cell. Physiol. 230:259-271, (Year: 2014).*
Kaufman et al., "Combination interleukin-2 and interleukin-12 induces severe gastrointestinal toxicity and epithelial cell apoptosis in mice," *Cytokine* 17:43-52 (2002).
Lasek et al., "Interleukin 12: still a promising candidate for tumor immunotherapy?" *Cancer Immunol. Immunother.* 63:419-435 (2014).
Mizuguchi et al., "IRES-dependent second gene expression is significantly lower than cap-dependent first gene expression in a bicistronic vector," *Mol. Ther.* 1:376-382 (2000).
Morgan et al., "Retroviral vectors containing putative internal ribosome entry sites: development of a polycistronic gene transfer system and applications to human gene therapy," *Nucleic Acids Res.* 20:1293-1299 (1992).
European Patent Office, International Search Report in International Patent Application No. PCT/EP2017/054216 (Apr. 25, 2017).
European Patent Office, Written Opinion of the International Searching Authority in International Patent Application No. PCT/EP2017/054216 (Apr. 25, 2017).
European Patent Office, Extended European Search Report in European Patent Application No. 16157423.1, 7 pp. (Aug. 1, 2016).
Intellectual Property India, First Examination Report in Indian Patent Application No. 201817034040 (Mar. 18, 2021).

(Continued)

*Primary Examiner* — Quang Nguyen
(74) *Attorney, Agent, or Firm* — Leydig, Voit & Mayer, Ltd.

(57) ABSTRACT

A method of treating cancer, a viral infection and/or an immune system disorder, comprising administering to a subject in need thereof a therapeutically effective amount of a pharmaceutical composition comprising a vector, wherein the vector comprises (a) nucleic acid sequences encoding 4-1BB ligand (4-1BBL), single chain IL-12 (scIL-12) and IL-2, and (b) at least one regulatory nucleic acid sequence providing for an increased expression level of 4-1BBL as compared to the expression levels of scIL-12 and IL-2, and other related methods.

4 Claims, 31 Drawing Sheets

Specification includes a Sequence Listing.

(56) References Cited

OTHER PUBLICATIONS

Yoshida, et al.; A Novel Adenovirus Expressing Human 4-1BB Ligand Enhances Antitumor Immunity; *Cancer Immunol. Immunotherapy*; 2003; vol. 52; pp. 97-106.

Renaud-Gabardos, et al.; Internal Ribosome Entry Site-Based Vectors For Combined Gene Therapy; *World J. Exp. Med.*; Feb. 20, 2015; vol. 5(1); pp. 11-20.

Ping-Ying, et al.; Regulation of Dendritic Cell Function by NK Cells: Mechanisms Underlying the Synergism in the Combination Therapy of IL-12 and 4-1BB Activation; *J. Immunology*; 2004; vol. 172; pp. 4779-4789.

Dowell et al., "Long-term proliferation of functional human NK cells, with conversion of $CD56^{dim}$ NK cells to a $CD56^{bright}$ phenotype, induced by carcinoma cells co-expressing 4-1BBL and IL-12." *Cancer Immunology, Immunotherapy*, vol. 61(5): pp. 615-628 (2012).

Huang et al., "Therapeutic and tumor-specific immunity induced by combination of dendritic cells and oncolytic adenovirus expressing IL-12 and 4-1BBL." *Molecular Therapy*, vol. 18(2): pp. 264-274 (2010).

China National Intellectual Property Administration, Office Action issued in Chinese Application No. 201780025515.9 (Apr. 1, 2022).

\* cited by examiner

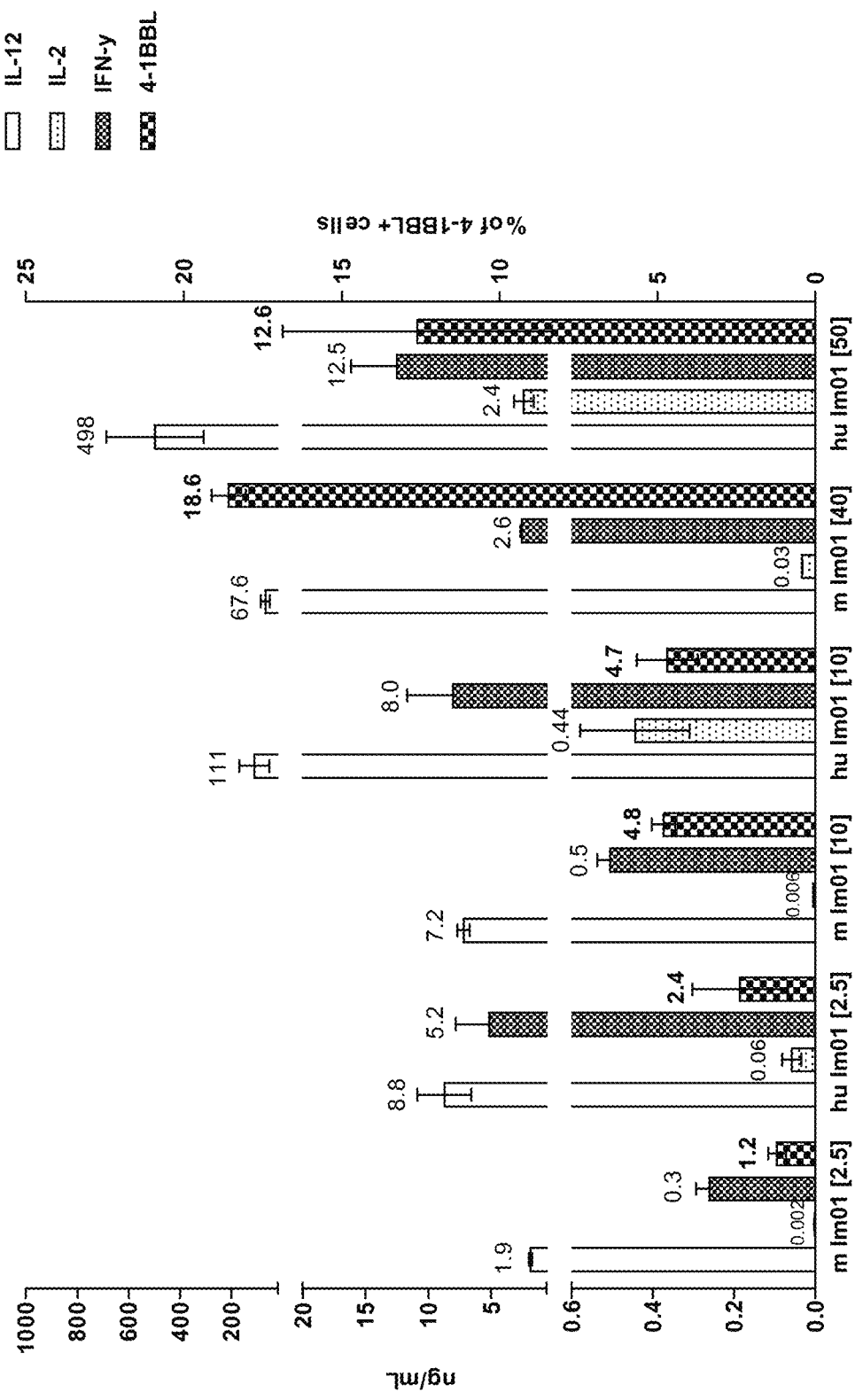
Figure 1: Transgene expression of IL-12, IL-2 and 4-1BBL and IFN-γ response of murine and human lm01

Figure 2: Schematic gene map of shuttle plasmid pE1.1 lm02
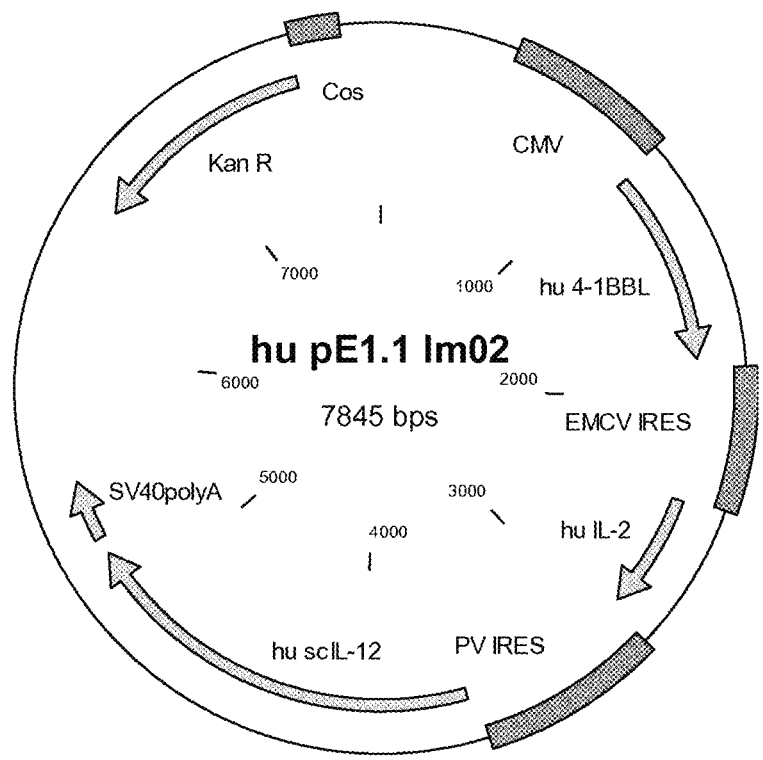

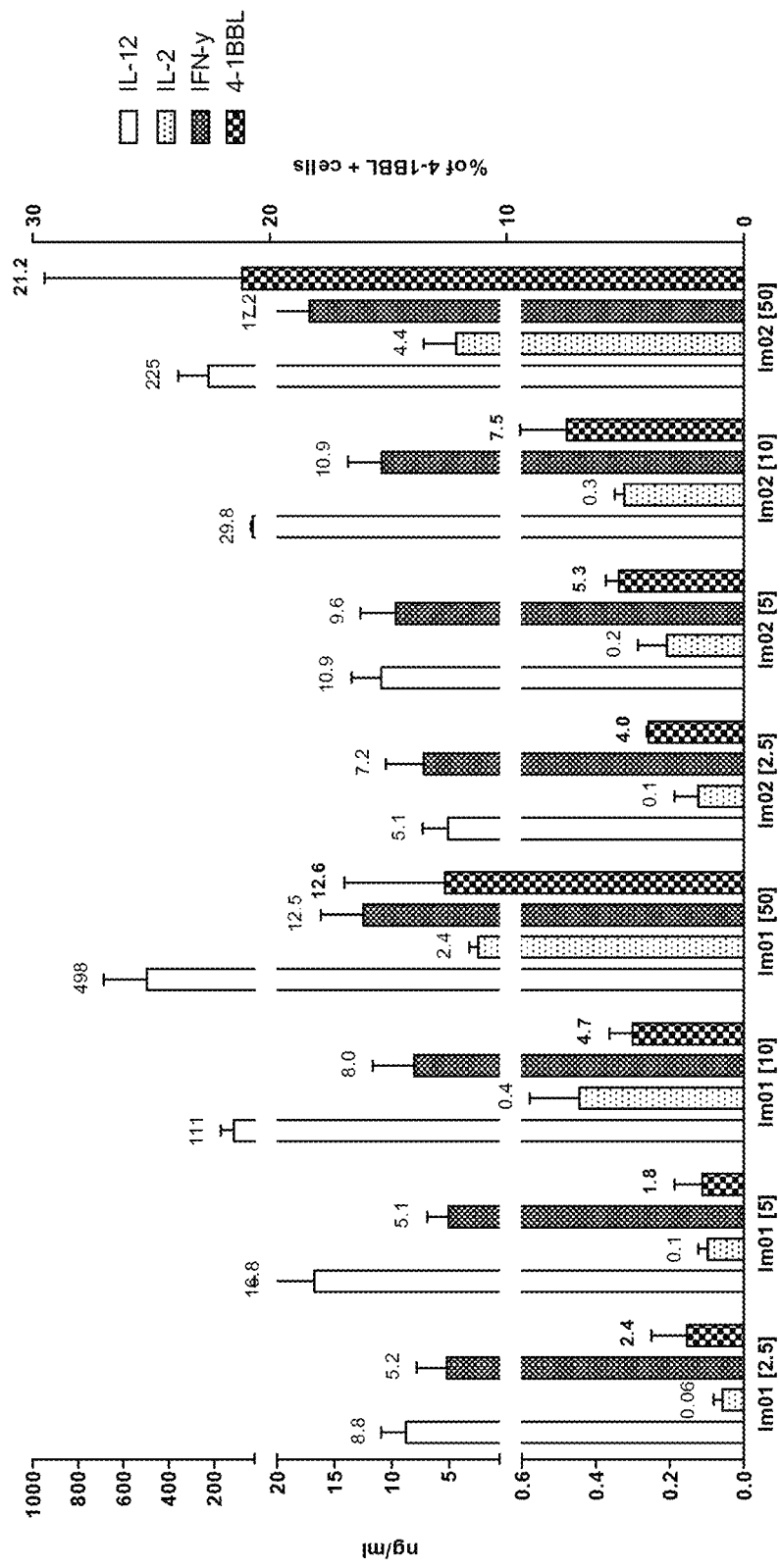

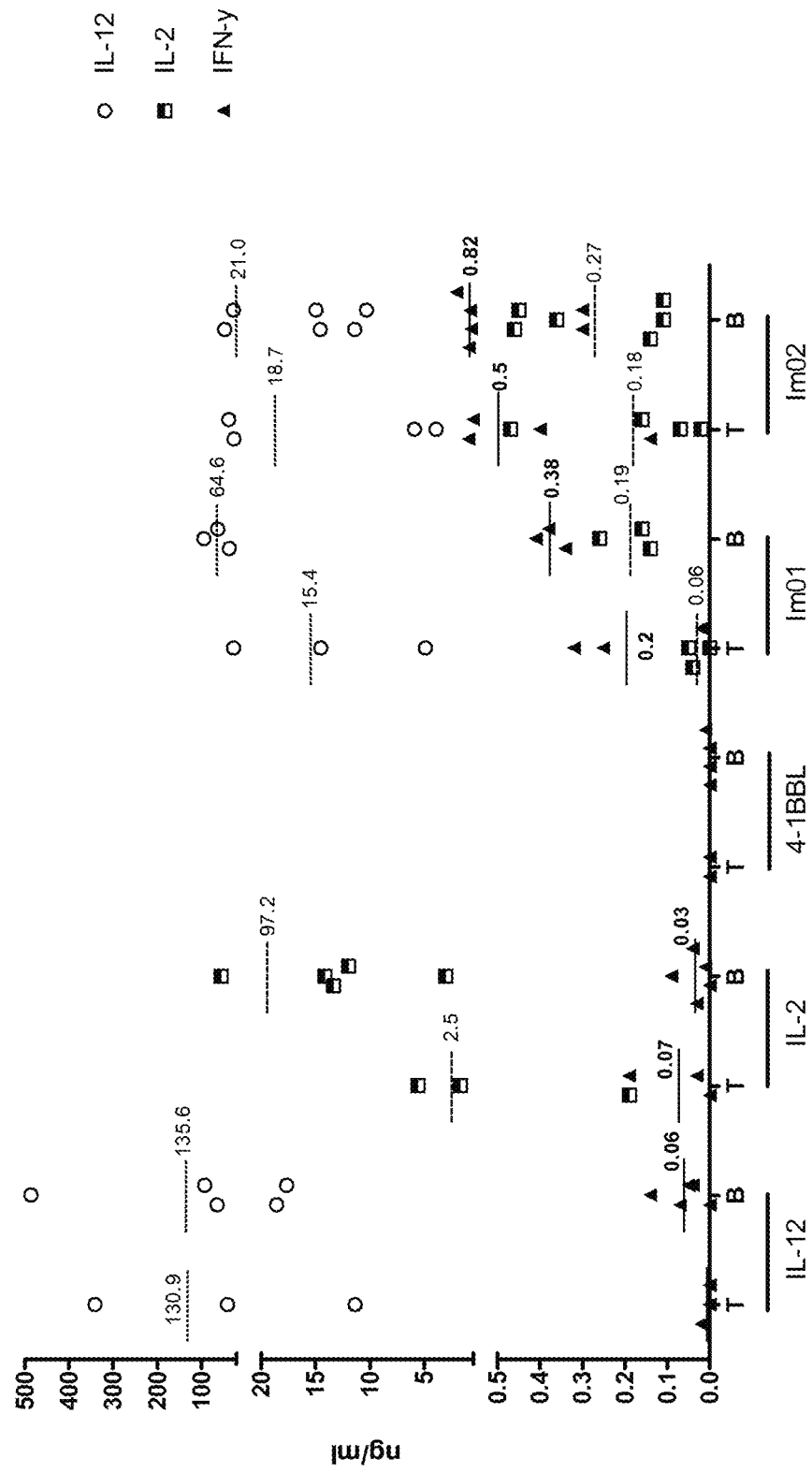
Figure 4: Comparison of Im02 and Im01 in a bladder tissue-based model

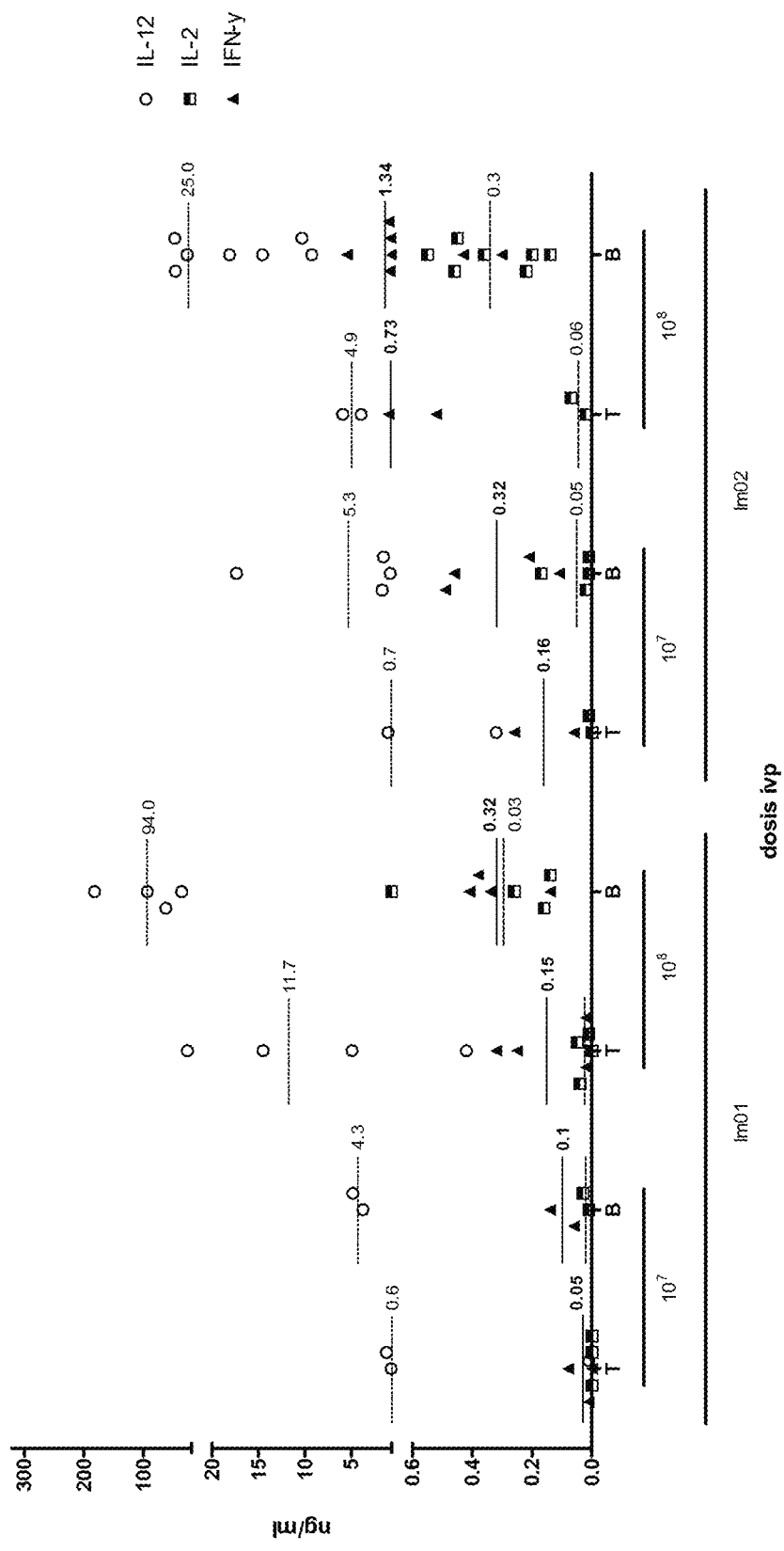

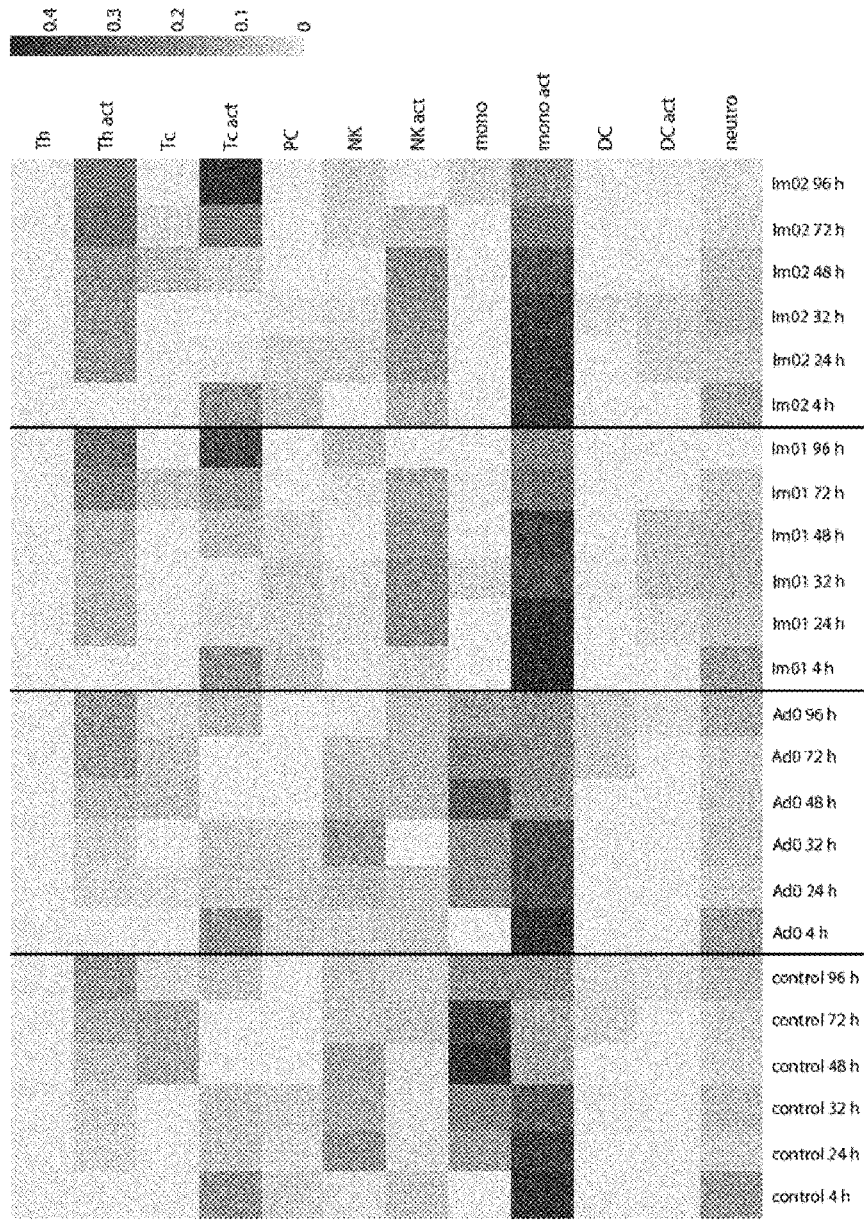
Figure 6: Heat-plot illustrating the activation of immune cell types in a co-culture of human bladder RT-4 carcinoma cells with human PBMCs.

Figure 7: Histologic examination of samples stimulated with Im02 or Ad0
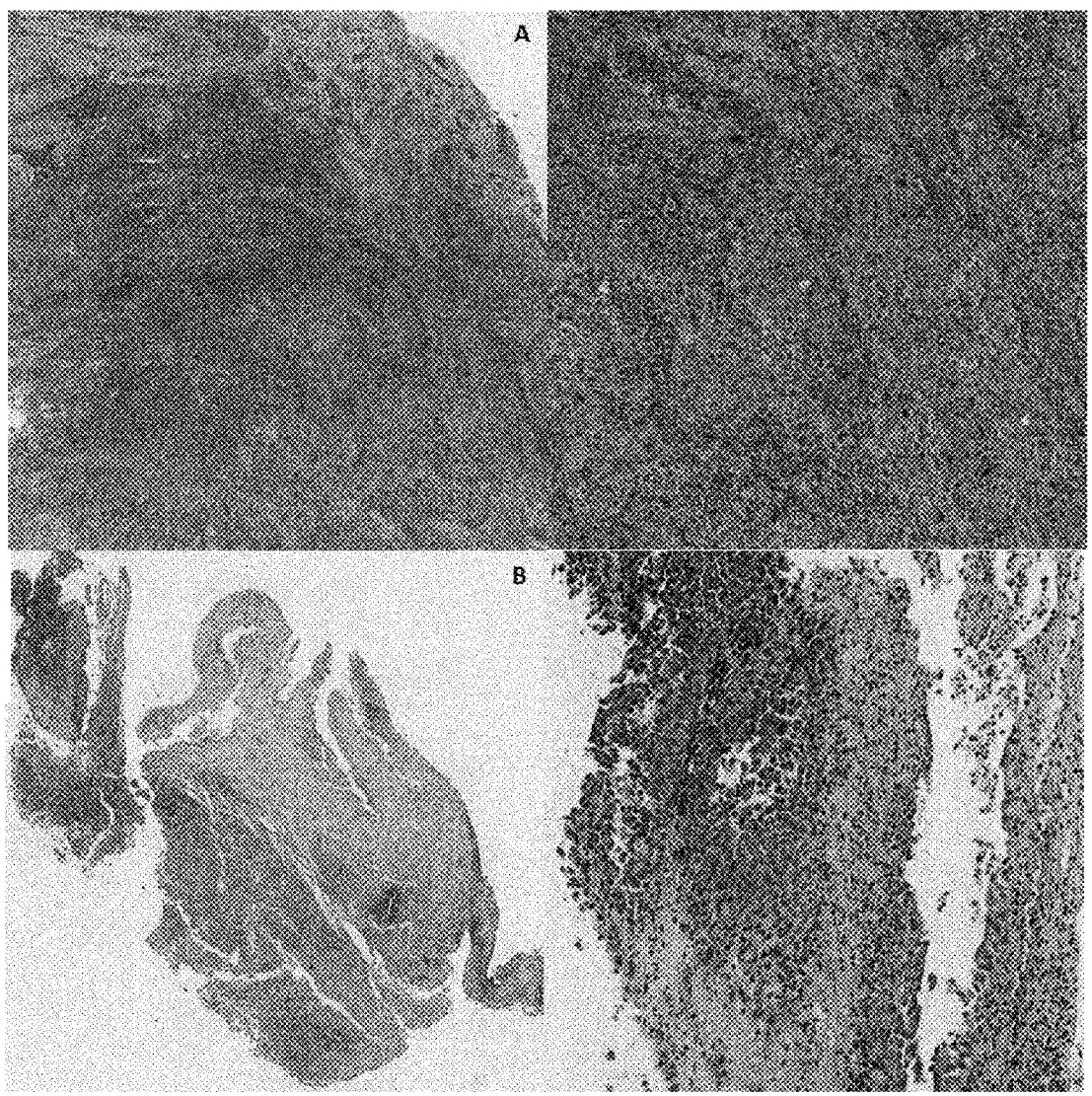

...Figure 7 continued
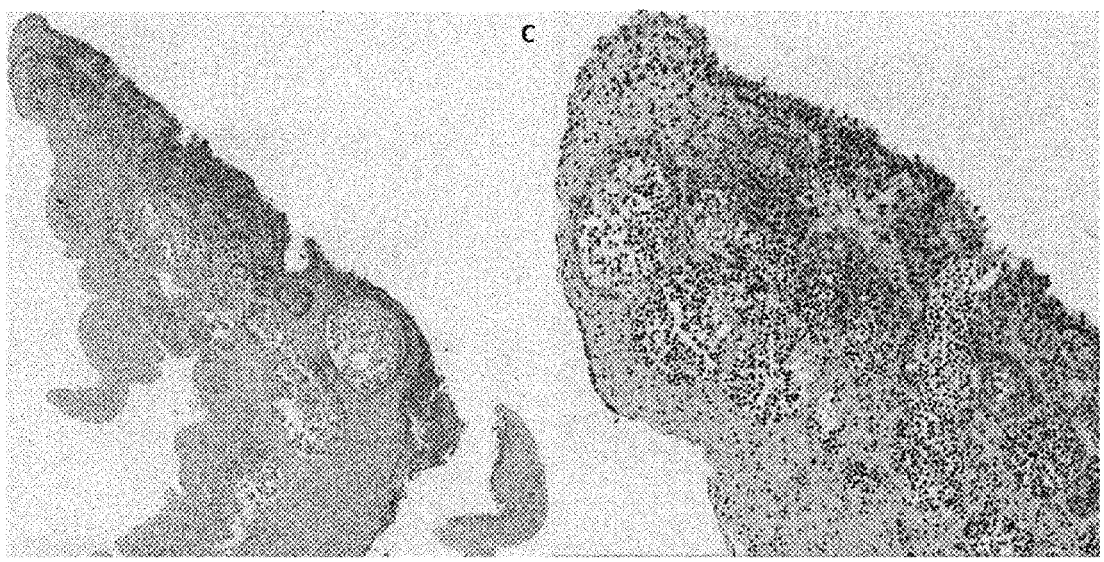

Figure 8: Histological examination of samples stimulated w/ or w/o lm02
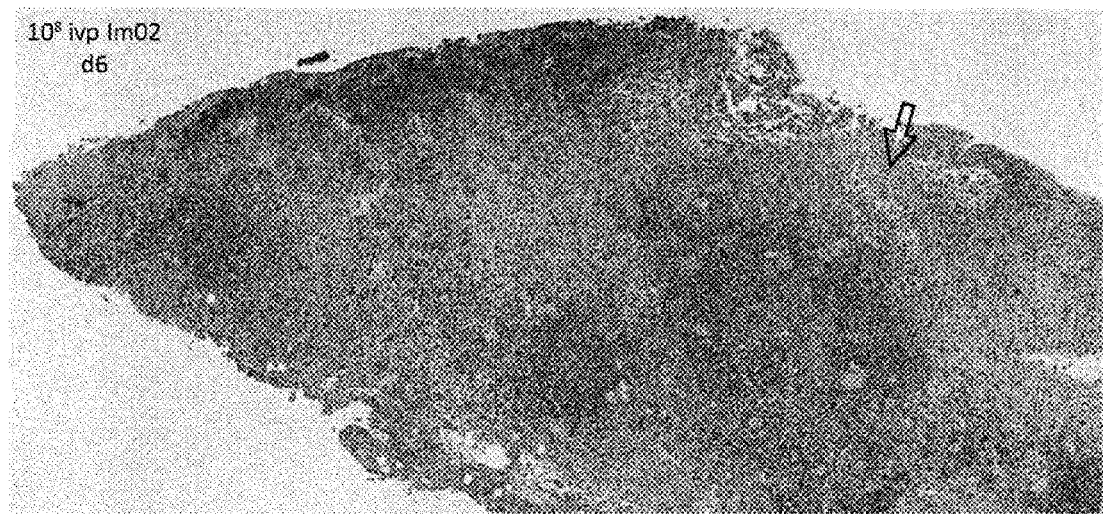

Figure 9: Target cell analysis and uptake mechanism by transmission electron microscopy
Panels 1 and 2:
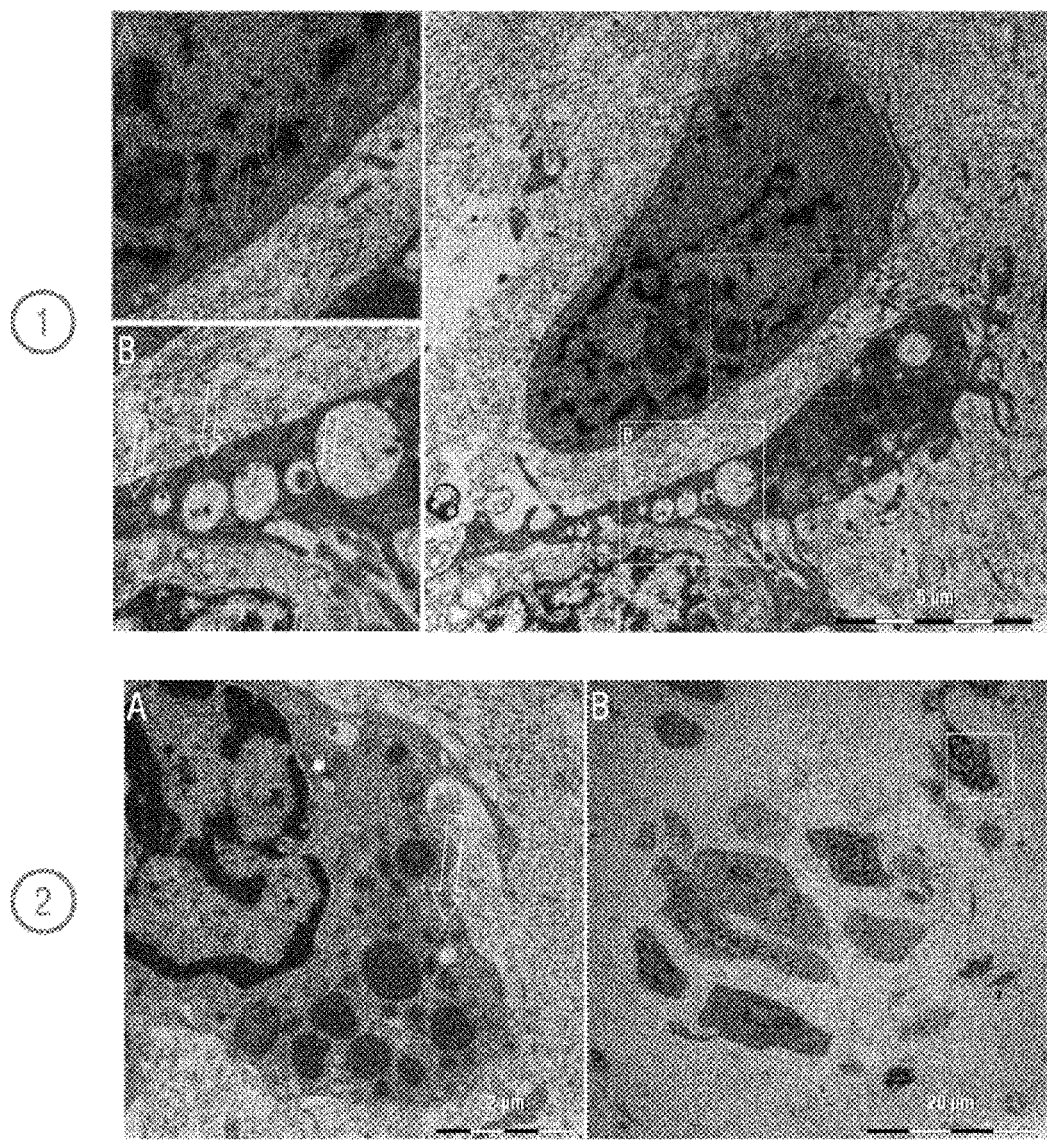

...*Figure 9 continued*
Panels 3-5:
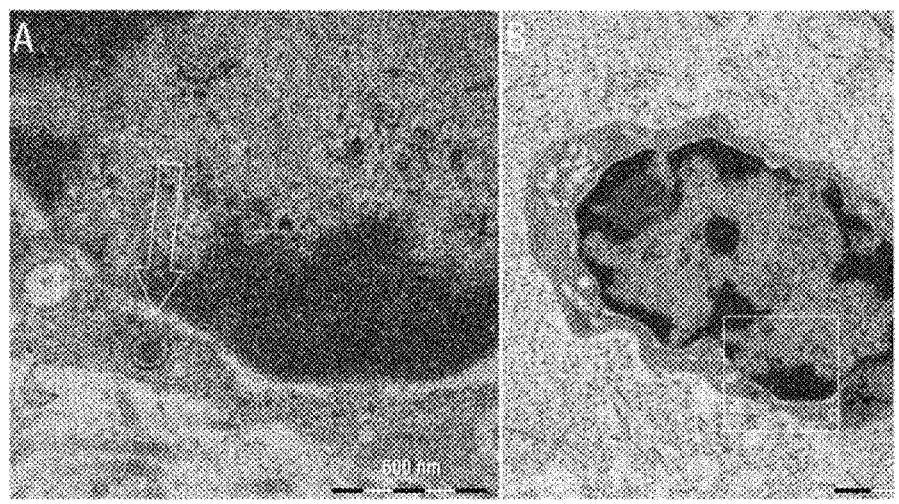
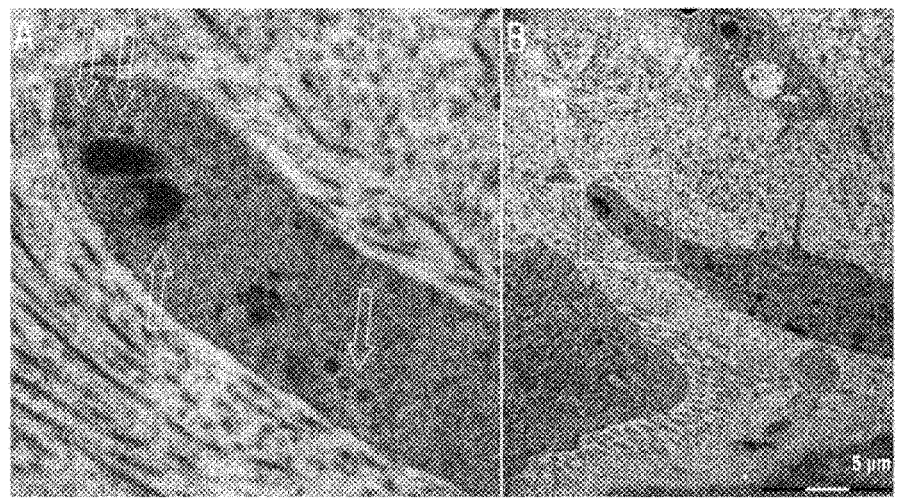
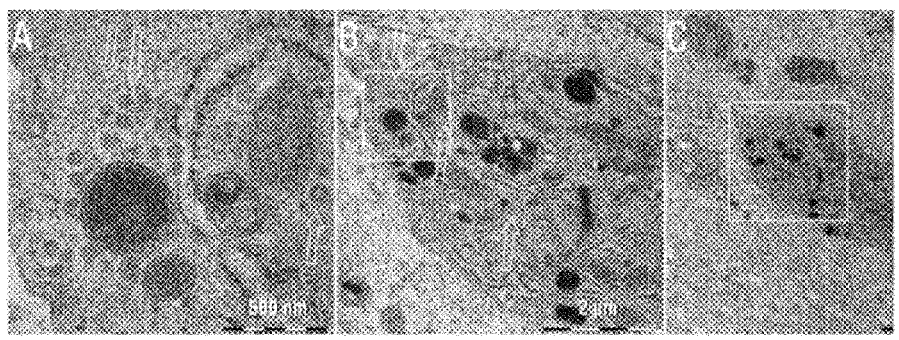

...*Figure 9 continued*
Panel 6:
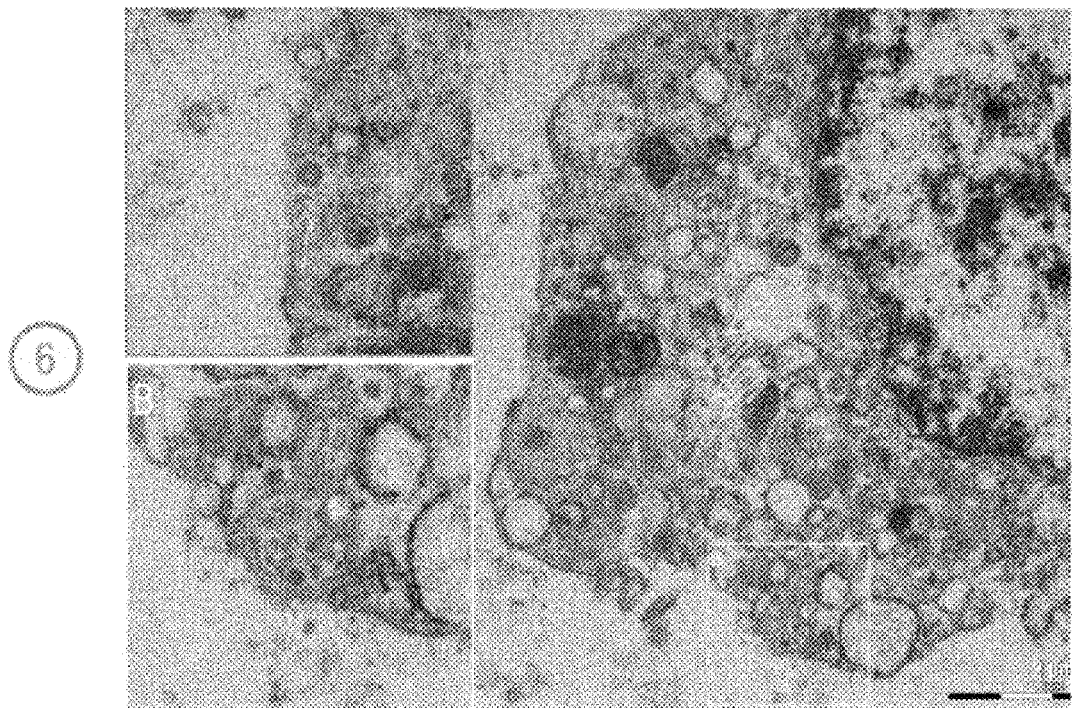

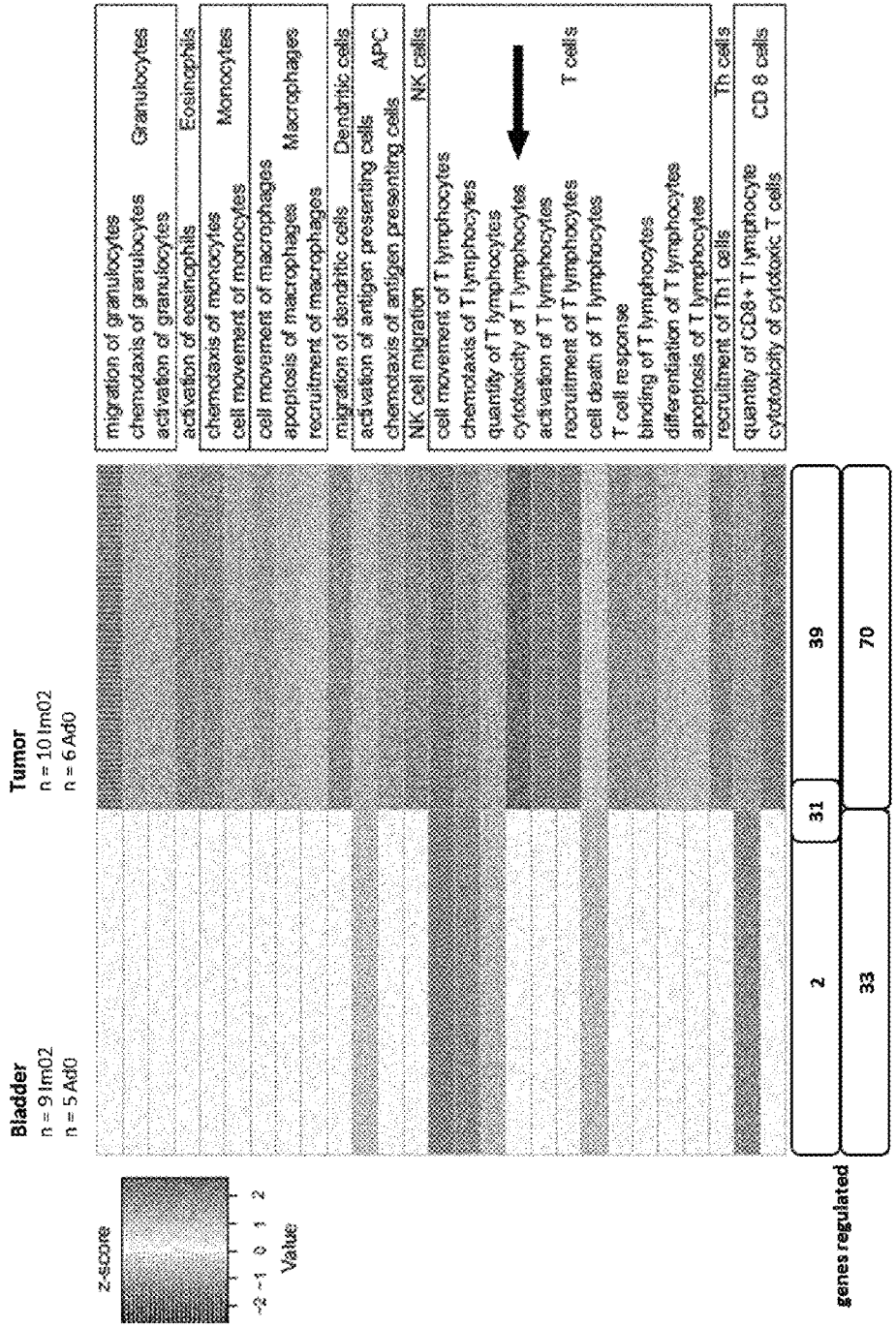
Figure 10: Comparison of differential expression in normal bladder and bladder tumor samples

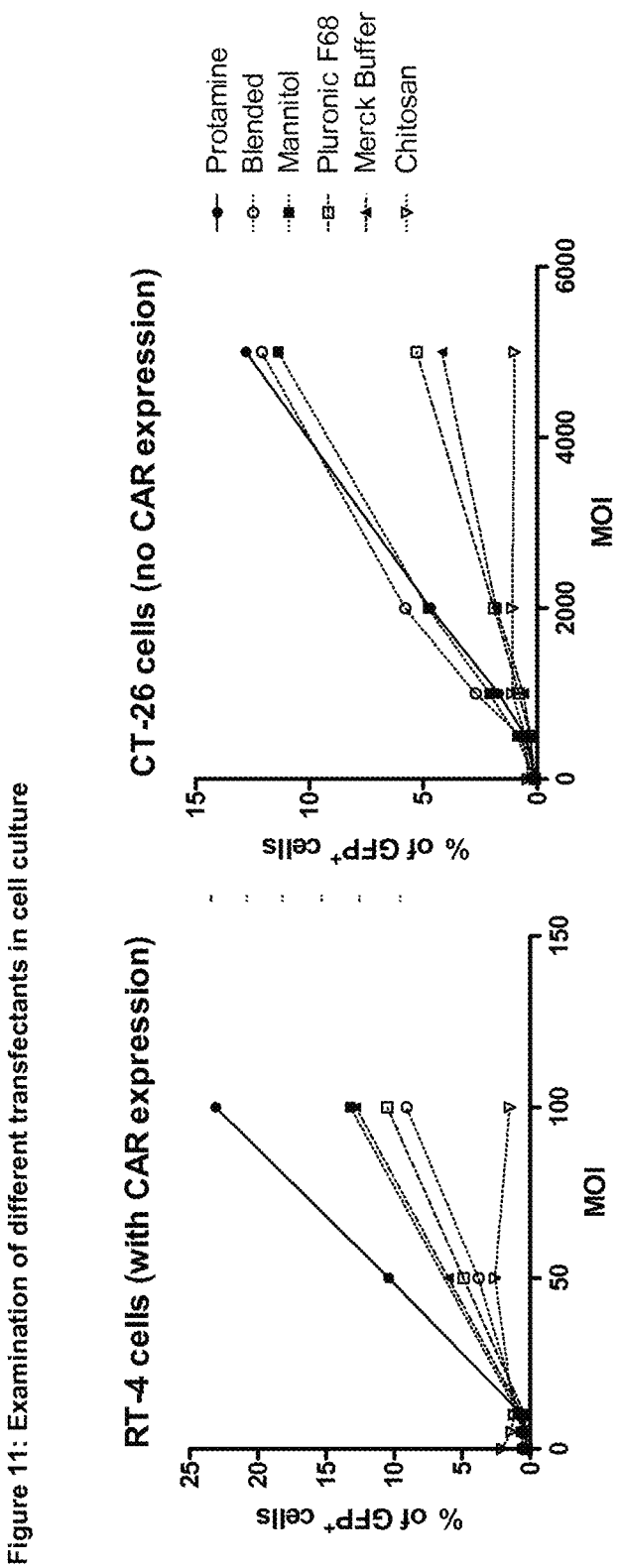

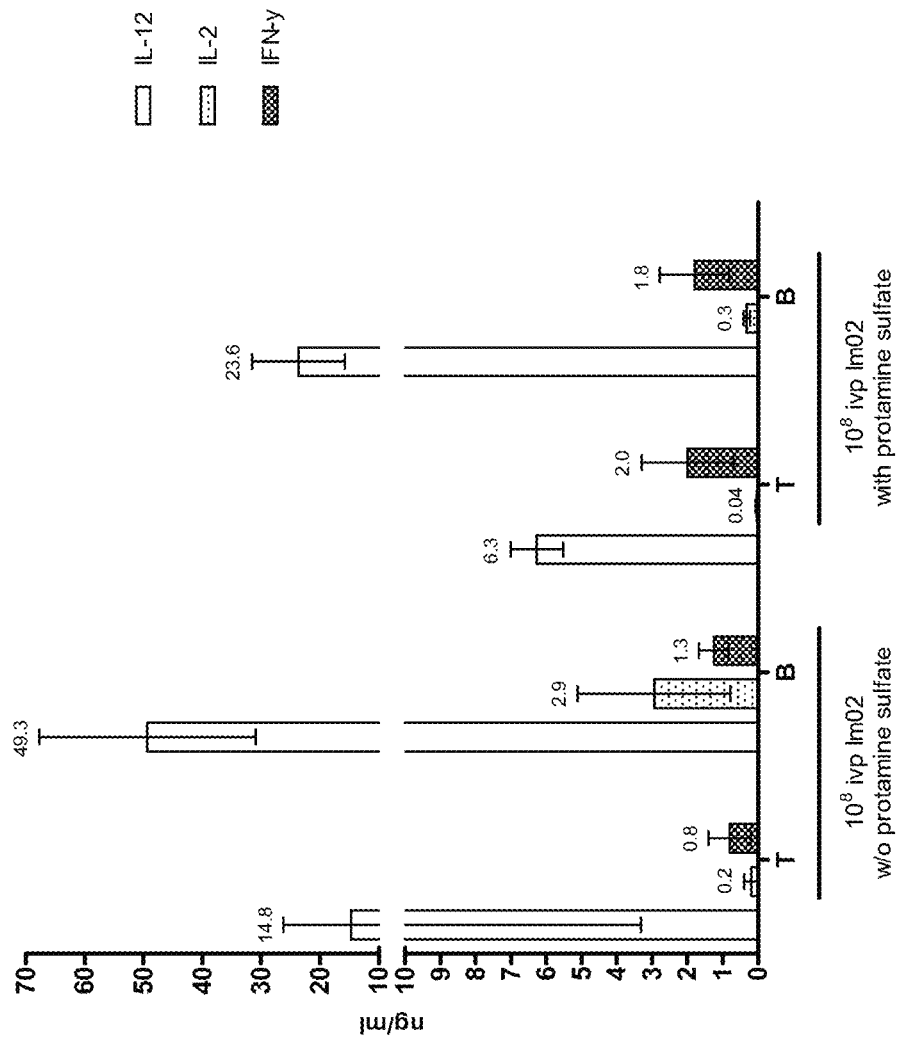

Figure 13: Nucleotide and amino acid sequence of human 4-1BBL

SEQ ID NO: 1: Nucleotide sequence of human 4-1BBL (765 nucleotides; origin: human 4-1BBL):

```
ATGGAATACGCCTCTGACGCTTCACTGGACCCCGAAGCCCCGTGGCCTCCCGCGCCCCGCGCTCGCGC
CTGCCGCGTACTGCCTTGGGCCCTGGTCGCGGGGCTGCTGCTGCTGCTGCTGCTCGCTGCCGCCTGCG
CCGTCTTCCTCGCCTGCCCTGGGCCGTGTCCGGGGCTCGCGCCTCGCCCGGCTCCGCGGCCAGCCCG
AGACTCCGCGAGGGTCCCGAGCTTTCGCCCGACGATCCCGCCGGCCTCTTGGACCTGCGGCAGGGCAT
GTTTGCGCAGCTGGTGGCCCAAAATGTTCTGCTGATCGATGGGCCCCTGAGCTGGTACAGTGACCCAG
GCCTGGCAGGCGTGTCCCTGACGGGGGGCCTGAGCTACAAAGAGGACACGAAGGAGCTGGTGGTGGCC
AAGGCTGGAGTCTACTATGTCTTCTTTCAACTAGAGCTGCGGCGCGTGGTGGCCGGCGAGGGCTCAGG
CTCCGTTTCACTTGCGCTGCACCTGCAGCCACTGCGCTCTGCTGCTGGGGCCGCCGCCCTGGCTTTGA
CCGTGGACCTGCCACCCGCCTCCTCCGAGGCTCGGAACTCGGCCTTCGGTTTCCAGGGCCGCTTGCTG
CACCTGAGTGCCGGCCAGCGCCTGGGCGTCCATCTTCACACTGAGGCCAGGGCACGCCATGCCTGGCA
GCTTACCCAGGGCGCCACAGTCTTGGGACTCTTCCGGGTGACCCCCGAAATCCCAGCCGGACTCCCTT
CACCGAGGTCGGAATAA
```

SEQ ID NO: 2: Amino acid sequence of human 4-1BBL (254 amino acid residues; translated sequence of the nucleotide sequence of SEQ ID NO: 1; origin: human 4-1BBL):

```
MEYASDASLDPEAPWPPAPRARACRVLPWALVAGLLLLLLLAAACAVFLACPWAVSGARASPGSAASP
RLREGPELSPDDPAGLLDLRQGMFAQLVAQNVLLIDGPLSWYSDPGLAGVSLTGGLSYKEDTKELVVA
KAGVYYVFFQLELRRVVAGEGSGSVSLALHLQPLRSAAGAAALALTVDLPPASSEARNSAFGFQGRLL
HLSAGQRLGVHLHTEARARHAWQLTQGATVLGLFRVTPEIPAGLPSPRSE
```

Figure 14: Nucleotide and amino acid sequence of human IL-2

SEQ ID NO: 3: Nucleotide sequence of human IL-2 (462 nucleotides; origin: human IL-2):

ATGTACAGGATGCAACTCCTGTCTTGCATTGCACTAAGTCTTGCACTTGTCACAAACAGTGCACCTAC
TTCAAGTTCTACAAAGAAAACACAGCTACAACTGGAGCATTTACTGCTGGATTTACAGATGATTTTGA
ATGGAATTAATAATTACAAGAATCCCAAACTCACCAGGATGCTCACATTTAAGTTTTACATGCCCAAG
AAGGCCACAGAACTGAAACATCTTCAGTGTCTAGAAGAAGAACTCAAACCTCTGGAGGAAGTGCTAAA
TTTAGCTCAAAGCAAAAACTTTCACTTAAGACCCAGGGACTTAATCAGCAATATCAACGTAATAGTTC
TGGAACTAAAGGGATCTGAAACAACATTCATGTGTGAATATGCTGATGAGACAGCAACCATTGTAGAA
TTTCTGAACAGATGGATTACCTTTTGTCAAAGCATCATCTCAACACTGACTTGA

SEQ ID NO: 4: Amino acid sequence of human IL-2 (153 amino acid residues; translated sequence of the nucleotide sequence of SEQ ID NO: 3; origin: human IL-2):

MYRMQLLSCIALSLALVTNSAPTSSSTKKTQLQLEHLLLDLQMILNGINNYKNPKLTRMLTFKFYMPK
KATELKHLQCLEEELKPLEEVLNLAQSKNFHLRPRDLISNINVIVLELKGSETTFMCEYADETATIVE
FLNRWITFCQSIISTLT

Figure 15: Nucleotide and amino acid sequence of human single-chain IL-12 (scIL-12)

SEQ ID NO: 5: Nucleotide sequence of human single-chain IL-12 (1,623 nucleotides; origin: artificial):

ATGTGTCACCAGCAGTTGGTCATCTCTTGGTTTTCCTGGTTTTTCTGGCATCTCCCCTCGTGGCCAT
ATGGGAACTGAAGAAAGATGTTTATGTCGTAGAATTGGATTGGTATCCGGATGCCCCTGGAGAAATGG
TGGTCCTCACCTGTGACACCCCTGAAGAAGATGGTATCACCTGGACCTTGGACCAGAGCAGTGAGGTC
TTAGGCTCTGGCAAAACCCTGACCATCCAAGTCAAAGAGTTTGGAGATGCTGGCCAGTACACCTGTCA
CAAAGGAGGCGAGGTTCTAAGCCATTCGCTCCTGCTGCTTCACAAAAAGGAAGATGGAATTTGGTCCA
CTGATATTTTAAAGGACCAGAAAGAACCCAAAAATAAGACCTTTCTAAGATGCGAGGCCAAGAATTAT
TCTGGACGTTTCACCTGCTGGTGGCTGACGACAATCAGTACTGATTTGACATTCAGTGTCAAAAGCAG
CAGAGGCTCTTCTGACCCCAAGGGGTGACGTGCGGAGCTGCTACACTCTCTGCAGAGAGTCAGAG
GGGACAACAAGGAGTATGAGTACTCAGTGGAGTGCCAGGAGGACAGTGCCTGCCCAGCTGCTGAGGAG
AGTCTGCCCATTGAGGTCATGGTGGATGCCGTTCACAAGCTCAAGTATGAAAACTACACCAGCAGCTT
CTTCATCAGGGACATCATCAAACCTGACCCACCCAAGAACTTGCAGCTGAAGCCATTAAAGAATTCTC
GGCAGGTGGAGGTCAGCTGGGAGTACCCTGACACCTGGAGTACTCCACATTCCTACTTCTCCCTGACA
TTCTGCGTTCAGGTCCAGGGCAAGAGCAAGAGAGAAAAGAAAGATAGAGTCTTCACGGACAAGACCTC
AGCCACGGTCATCTGCCGCAAAAATGCCAGCATTAGCGTGCGGGCCCAGGACCGCTACTATAGCTCAT
CTTGGAGCGAATGGGCATCTGTGCCCTGCAGT<u>**GGTGGCGGTGGAAGCGGCGGTGGCGGAAGCGGCGGT
GGCGGCAGC**</u>AGAAACCTCCCCGTGGCCACTCCAGACCCAGGAATGTTCCCATGCCTTCACCACTCCCA
AAACCTGCTGAGGGCCGTCAGCAACATGCTCCAGAAGGCCAGACAAACTCTAGAATTTTACCCTTGCA
CTTCTGAAGAGATTGATCATGAAGATATCACAAAAGATAAAACCAGCACAGTGGAGGCCTGTTTACCA
TTGGAATTAACCAAGAATGAGAGTTGCCTAAATTCCAGAGAGACCTCTTTCATAACTAATGGGAGTTG
CCTGGCCTCCAGAAAGACCTCTTTTATGATGGCCCTGTGCCTTAGTAGTATTTATGAAGACTTGAAGA
TGTACCAGGTGGAGTTCAAGACCATGAATGCAAAGCTTCTGATGGATCCTAAGAGGCAGATCTTTCTA
GATCAAAACATGCTGGCAGTTATTGATGAGCTGATGCAGGCCCTGAATTTCAACAGTGAGACTGTGCC
ACAAAAATCCTCCCTTGAAGAACCGGATTTTTATAAAACTAAAATCAAGCTCTGCATACTTCTTCATG
CTTTCAGAATTCGGGCAGTGACTATTGATAGAGTGATGAGCTATCTGAATGCTTCCTAA

...Figure 15 continued

SEQ ID NO: 6: Amino acid sequence of human single-chain IL-12 (540 amino acid residues; translated sequence of the nucleotide sequence of SEQ ID NO: 5; origin: artificial):

MCHQQLVISWFSLVFLASPLVAIWELKKDVYVVELDWYPDAPGEMVVLTCDTPEEDGITWTLDQSSEV
LGSGKTLTIQVKEFGDAGQYTCHKGGEVLSHSLLLLHKKEDGIWSTDILKDQKEPKNKTFLRCEAKNY
SGRFTCWWLTTISTDLTFSVKSSRGSSDPQGVTCGAATLSAERVRGDNKEYEYSVECQEDSACPAAEE
SLPIEVMVDAVHKLKYENYTSSFFIRDIIKPDPPKNLQLKPLKNSRQVEVSWEYPDTWSTPHSYFSLT
FCVQVQGKSKREKKDRVFTDKTSATVICRKNASISVRAQDRYYSSSWSEWASVPCSGGGGSGGGGSGG
GGSRNLPVATPDPGMFPCLHHSQNLLRAVSNMLQKARQTLEFYPCTSEEIDHEDITKDKTSTVEACLP
LELTKNESCLNSRETSFITNGSCLASRKTSFMMALCLSSIYEDLKMYQVEFKTMNAKLLMDPKRQIFL
DQNMLAVIDELMQALNFNSETVPQKSSLEEPDFYKTKIKLCILLHAFRIRAVTIDRVMSYLNAS

Figure 16: Nucleotide and amino acid sequences of the 35 kDa and 40 kDa subunits of human IL-12

SEQ ID NO: 7: Nucleotide sequence of the 40 kDa subunit of IL-12 (987 nucleotides; origin: human IL-12, Genbank NM_002187):

ATGTGTCACCAGCAGTTGGTCATCTCTTGGTTTTCCCTGGTTTTTCTGGCATCTCCCCTCGTGGCCAT
ATGGGAACTGAAGAAAGATGTTTATGTCGTAGAATTGGATTGGTATCCGGATGCCCCTGGAGAAATGG
TGGTCCTCACCTGTGACACCCCTGAAGAAGATGGTATCACCTGGACCTTGGACCAGAGCAGTGAGGTC
TTAGGCTCTGGCAAAACCCTGACCATCCAAGTCAAAGAGTTTGGAGATGCTGGCCAGTACACCTGTCA
CAAAGGAGGCGAGGTTCTAAGCCATTCGCTCCTGCTGCTTCACAAAAAGGAAGATGGAATTTGGTCCA
CTGATATTTTAAAGGACCAGAAAGAACCCAAAAATAAGACCTTTCTAAGATGCGAGGCCAAGAATTAT
TCTGGACGTTTCACCTGCTGGTGGCTGACGACAATCAGTACTGATTTGACATTCAGTGTCAAAAGCAG
CAGAGGCTCTTCTGACCCCCAAGGGGTGACGTGCGGAGCTGCTACACTCTCTGCAGAGAGAGTCAGAG
GGGACAACAAGGAGTATGAGTACTCAGTGGAGTGCCAGGAGGACAGTGCCTGCCCAGCTGCTGAGGAG
AGTCTGCCCATTGAGGTCATGGTGGATGCCGTTCACAAGCTCAAGTATGAAAACTACACCAGCAGCTT
CTTCATCAGGGACATCATCAAACCTGACCCACCCAAGAACTTGCAGCTGAAGCCATTAAAGAATTCTC
GGCAGGTGGAGGTCAGCTGGGAGTACCCTGACACCTGGAGTACTCCACATTCCTACTTCTCCCTGACA
TTCTGCGTTCAGGTCCAGGGCAAGAGCAAGAGAGAAAAGAAAGATAGAGTCTTCACGGACAAGACCTC
AGCCACGGTCATCTGCCGCAAAAATGCCAGCATTAGCGTGCGGGCCCAGGACCGCTACTATAGCTCAT
CTTGGAGCGAATGGGCATCTGTGCCCTGCAGTTAG

SEQ ID NO: 8: Amino acid sequence of the 40 kDa subunit of IL-12 (328 amino acid residues; translated sequence of the nucleotide sequence of SEQ ID NO: 7; origin: human IL-12, Genbank NM_002187):

MCHQQLVISWFSLVFLASPLVAIWELKKDVYVVELDWYPDAPGEMVVLTCDTPEEDGITWTLDQSSEV
LGSGKTLTIQVKEFGDAGQYTCHKGGEVLSHSLLLHKKEDGIWSTDILKDQKEPKNKTFLRCEAKNY
SGRFTCWWLTTISTDLTFSVKSSRGSSDPQGVTCGAATLSAERVRGDNKEYEYSVECQEDSACPAAEE
SLPIEVMVDAVHKLKYENYTSSFFIRDIIKPDPPKNLQLKPLKNSRQVEVSWEYPDTWSTPHSYFSLT
FCVQVQGKSKREKKDRVFTDKTSATVICRKNASISVRAQDRYYSSSWSEWASVPCS

_...Figure 16 continued_

SEQ ID NO: 9: Nucleotide sequence of the 35 kDa subunit of IL-12 (762 nucleotides; origin: human IL-12, Genbank NM_000882):

ATGTGGCCCCTGGGTCAGCCTCCCAGCCACCGCCCTCACCTGCCGCGGCCACAGGTCTGCATCCAGC
GGCTCGCCCTGTGTCCCTGCAGTGCCGGCTCAGCATGTGTCCAGCGCGCAGCCTCCTCCTTGTGGCTA
CCCTGGTCCTCCTGGACCACCTCAGTTTGGCCAGAAACCTCCCCGTGGCCACTCCAGACCCAGGAATG
TTCCCATGCCTTCACCACTCCCAAAACCTGCTGAGGGCCGTCAGCAACATGCTCCAGAAGGCCAGACA
AACTCTAGAATTTTACCCTTGCACTTCTGAAGAGATTGATCATGAAGATATCACAAAAGATAAAACCA
GCACAGTGGAGGCCTGTTTACCATTGGAATTAACCAAGAATGAGAGTTGCCTAAATTCCAGAGAGACC
TCTTTCATAACTAATGGGAGTTGCCTGGCCTCCAGAAAGACCTCTTTTATGATGGCCCTGTGCCTTAG
TAGTATTTATGAAGACTTGAAGATGTACCAGGTGGAGTTCAAGACCATGAATGCAAAGCTTCTGATGG
ATCCTAAGAGGCAGATCTTTCTAGATCAAAACATGCTGGCAGTTATTGATGAGCTGATGCAGGCCCTG
AATTTCAACAGTGAGACTGTGCCACAAAAATCCTCCCTTGAAGAACCGGATTTTTATAAAACTAAAAT
CAAGCTCTGCATACTTCTTCATGCTTTCAGAATTCGGGCAGTGACTATTGATAGAGTGATGAGCTATC
TGAATGCTTCCTAA

SEQ ID NO: 10: Amino acid sequence of the 35 kDa subunit of IL-12 (253 amino acid residues; translated sequence of the nucleotide sequence of SEQ ID NO: 9; origin: human IL-12, Genbank NM_000882):

MWPPGSASQPPPSPAAATGLHPAARPVSLQCRLSMCPARSLLLVATLVLLDHLSLARNLPVATPDPGM
FPCLHHSQNLLRAVSNMLQKARQTLEFYPCTSEEIDHEDITKDKTSTVEACLPLELTKNESCLNSRET
SFITNGSCLASRKTSFMMALCLSSIYEDLKMYQVEFKTMNAKLLMDPKRQIFLDQNMLAVIDELMQAL
NFNSETVPQKSSLEEPDFYKTKIKLCILLHAFRIRAVTIDRVMSYLNAS

Figure 17: Nucleotide sequence of the shuttle vector hu pE1.1 Im02 shown in Figure 2

SEQ ID NO: 11: Nucleotide sequence of the shuttle vector hu pE1.1 Im02 shown in Figure 2 (7,845 nucleotides; origin: artificial):

```
TTAACATCATCAATAATATACCTTATTTTGGATTGAAGCCAATATGATAATGAGGGGGTGGAGTTTGT
GACGTGGCGCGGGGCGTGGGAACGGGGCGGGTGACGTAGTAGTGTGGCGGAAGTGTGATGTTGCAAGT
GTGGCGGAACACATGTAAGCGACGGATGTGGCAAAAGTGACGTTTTTGGTGTGCGCCGGTGTACACAG
GAAGTGACAATTTTCGCGCGGTTTTAGGCGGATGTTGTAGTAAATTTGGGCGTAACCGAGTAAGATTT
GGCCATTTTCGCGGGAAAACTGAATAAGAGGAAGTGAAATCTGAATAATTTTGTGTTACTCATAGCGC
GTAATATTTGTCTAGGGAGATCTTCTAGACCCGGGAGCGGCCGGCCGCTGTCGACCGTAACTATAACG
GTCCTAAGGTAGCGAACCACGTCAGGTCGAGTGTTCATGAATGGAAGATATCTGCGCCCTAGCGCCGG
CGAGCTCTAGTAATCAATTACGGGGTCATTAGTTCATAGCCCATATATGGAGTTCCGCGTTACATAAC
TTACGGTAAATGGCCCGCCTGGCTGACCGCCCAACGACCCCCGCCCATTGACGTCAATAATGACGTAT
GTTCCCATAGTAACGCCAATAGGGACTTTCCATTGACGTCAATGGGTGGAGTATTTACGGTAAACTGC
CCACTTGGCAGTACATCAAGTGTATCATATGCCAAGTACGCCCCCTATTGACGTCAATGACGGTAAAT
GGCCCGCCTGGCATTATGCCCAGTACATGACCTTATGGGACTTTCCTACTTGGCAGTACATCTACGTA
TTAGTCATCGCTATTACCATGGTGATGCGGTTTTGGCAGTACATCAATGGGCGTGGATAGCGGTTTGA
CTCACGGGGATTTCCAAGTCTCCACCCCATTGACGTCAATGGGAGTTTGTTTTGGCACCAAAATCAAC
GGGACTTTCCAAAATGTCGTAACAACTCCGCCCCATTGACGCAAATGGGCGGTAGGCGTGTACGGTGG
GAGGTCTATATAAGCAGAGCTGGTTTAGTGAACCGTCAGATCCGCTAGACGGACCGACCATGGAATAC
GCCTCTGACGCTTCACTGGACCCCGAAGCCCGTGGCCTCCCGCGCCCCGCGCTCGCGCCTGCCGCGT
ACTGCCTTGGGCCCTGGTCGCGGGGCTGCTGCTGCTGCTGCTCGCTGCCGCCTGCGCCGTCTTCC
TCGCCTGCCCCTGGGCCGTGTCCGGGGCTCGCGCCTCGCCCGGCTCCGCGGCCAGCCCGAGACTCCGC
GAGGGTCCCGAGCTTTCGCCCGACGATCCCGCCGGCCTCTTGGACCTGCGGCAGGGCATGTTTGCGCA
GCTGGTGGCCCAAAATGTTCTGCTGATCGATGGGCCCCTGAGCTGGTACAGTGACCCAGGCCTGGCAG
GCGTGTCCCTGACGGGGGGCCTGAGCTACAAAGAGGACACGAAGGAGCTGGTGGTGGCCAAGGCTGGA
GTCTACTATGTCTTCTTTCAACTAGAGCTGCGGCGCGTGGTGGCCGGCGAGGGCTCAGGCTCCGTTTC
ACTTGCGCTGCACCTGCAGCCACTGCGCTCTGCTGCTGGGCCGCCGCCCTGGCTTTGACCGTGGACC
TGCCACCCGCCTCCTCCGAGGCTCGGAACTCGGCCTTCGGTTTCCAGGGCCGCTTGCTGCACCTGAGT
GCCGGCCAGCGCCTGGGCGTCCATCTTCACACTGAGGCCAGGGCACGCCATGCCTGGCAGCTTACCCA
GGGCGCCACAGTCTTGGGACTCTTCCGGGTGACCCCGAAATCCCAGCCGGACTCCCTTCACCGAGGT
CGGAATAAGAACGCTAGCTCTTGTGACTGGCGCGCCTGATCAATCGATGTTTAAACGTTATTTTCCAC
CATATTGCCGTCTTTTGGCAATGTGAGGGCCCGGAAACCTGGCCCTGTCTTCTTGACGAGCATTCCTA
GGGGTCTTTCCCCTCTCGCCAAAGGAATGCAAGGTCTGTTGAATGTCGTGAAGGAAGCAGTTCCTCTG
```

...*Fig. 17 continued*

```
GAAGCTTCTTGAAGACAAACAACGTCTGTAGCGACCCTTTGCAGGCAGCGGAACCCCCCACCTGGCGA
CAGGTGCCTCTGCGGCCAAAAGCCACGTGTATAAGATACACCTGCAAAGGCGGCACAACCCCAGTGCG
ACGTTGTGAGTTGGATAGTTGTGGAAAGAGTCAAATGGCTCTCCTCAAGCGTATTCAACAAGGGGCTG
AAGGATGCCCAGAAGGTACCCCATTGTATGGGATCTGATCTGGGGCCTCGGTGCACATGCTTTACGTG
TGTTTAGTCGAGGTTAAAAAAACGTCTAGGCCCCCCGAACCACGGGGACGTGGTTTTCCTTTGAAAAA
CACGATTCTCGAGACTAGTCGTACGACCATGTACAGGATGCAACTCCTGTCTTGCATTGCACTAAGTC
TTGCACTTGTCACAAACAGTGCACCTACTTCAAGTTCTACAAAGAAAACACAGCTACAACTGGAGCAT
TTACTGCTGGATTTACAGATGATTTTGAATGGAATTAATAATTACAAGAATCCCAAACTCACCAGGAT
GCTCACATTTAAGTTTTACATGCCCAAGAAGGCCACAGAACTGAAACATCTTCAGTGTCTAGAAGAAG
AACTCAAACCTCTGGAGGAAGTGCTAAATTTAGCTCAAAGCAAAAACTTTCACTTAAGACCCAGGGAC
TTAATCAGCAATATCAACGTAATAGTTCTGGAACTAAAGGGATCTGAAACAACATTCATGTGTGAATA
TGCTGATGAGACAGCAACCATTGTAGAATTTCTGAACAGATGGATTACCTTTTGTCAAAGCATCATCT
CAACACTGACTTGAACGCGTGCTAGCAGGCCCGGCCGGCCTTGTTAAAGACAGGATGAAGCTTAAAAC
AGCTCTGGGGTTGTACCCACCCCAGAGGCCCACGTGGCGGCTAGTACTCCGGTATTGCGGTACCCTTG
TACGCCTGTTTTATACTCCCTTCCCGTAACTTAGACGCACAAAACCAAGTTCAATAGAAGGGGGTACA
AACCAGTACCACCACGAACAAGCACTTCTGTTTCCCCGGTGATGTCGTATAGACTGCTTGCGTGGTTG
AAAGCGACGGATCCGTTATCCGCTTATGTACTTCGAGAAGCCCAGTACCACCTCGGAATCTTCGATGC
GTTGCGCTCAGCACTCAACCCCAGAGTGTAGCTTAGGCTGATGAGTCTGGACATCCCTCACCGGTGAC
GGTGGTCCAGGCTGCGTTGGCGGCCTACCTATGGCTAACGCCATGGGACGCTAGTTGTGAACAAGGTG
TGAAGAGCCTATTGAGCTACATAAGAATCCTCCGGCCCCTGAATGCGGCTAATCCCAACCTCGGAGCA
GGTGGTCACAAACCAGTGATTGGCCTGTCGTAACGCGCAAGTCCGTGGCGGAACCGACTACTTTGGGT
GTCCGTGTTTCCTTTTATTTTATTGTGGCTGCTTATGGTGACAATCACAGATTGTTATCATAAAGCGA
ATTGGATTGCGTACGCGGACCGAACTAGTTTCGCCGCCTCCAACATGTGTCACCAGCAGTTGGTCATC
TCTTGGTTTTCCCTGGTTTTTCTGGCATCTCCCTCGTGGCCATATGGGAACTGAAGAAAGATGTTTA
TGTCGTAGAATTGGATTGGTATCCGGATGCCCCTGGAGAAATGGTGGTCCTCACCTGTGACACCCCTG
AAGAAGATGGTATCACCTGGACCTTGGACCAGAGCAGTGAGGTCTTAGGCTCTGGCAAAACCCTGACC
ATCCAAGTCAAAGAGTTTGGAGATGCTGGCCAGTACACCTGTCACAAAGGAGGCGAGGTTCTAAGCCA
TTCGCTCCTGCTGCTTCACAAAAGGAAGATGGAATTTGGTCCACTGATATTTAAAGGACCAGAAAG
AACCCAAAAATAAGACCTTTCTAAGATGCGAGGCCAAGAATTATTCTGGACGTTTCACCTGCTGGTGG
CTGACGACAATCAGTACTGATTTGACATTCAGTGTCAAAAGCAGCAGAGGCTCTTCTGACCCCCAAGG
GGTGACGTGCGGAGCTGCTACACTCTCTGCAGAGAGAGTCAGAGGGGACAACAAGGAGTATGAGTACT
CAGTGGAGTGCCAGGAGGACAGTGCCTGCCCAGCTGCTGAGGAGAGTCTGCCCATTGAGGTCATGGTG
GATGCCGTTCACAAGCTCAAGTATGAAAACTACACCAGCAGCTTCTTCATCAGGGACATCATCAAACC
TGACCCACCCAAGAACTTGCAGCTGAAGCCATTAAAGAATTCTCGGCAGGTGGAGGTCAGCTGGGAGT
ACCCTGACACCTGGAGTACTCCACATTCCTACTTCTCCCTGACATTCTGCGTTCAGGTCCAGGGCAAG
AGCAAGAGAGAAAAGAAAGATAGAGTCTTCACGGACAAGACCTCAGCCACGGTCATCTGCCGCAAAAA
```

...Fig. 17 continued

```
TGCCAGCATTAGCGTGCGGGCCCAGGACCGCTACTATAGCTCATCTTGGAGCGAATGGGCATCTGTGC
CCTGCAGTGGTGGCGGTGGAAGCGGCGGTGGCGGAAGCGGCGGTGGCGGCAGCAGAAACCTCCCCGTG
GCCACTCCAGACCCAGGAATGTTCCCATGCCTTCACCACTCCCAAAACCTGCTGAGGGCCGTCAGCAA
CATGCTCCAGAAGGCCAGACAAACTCTAGAATTTTACCCTTGCACTTCTGAAGAGATTGATCATGAAG
ATATCACAAAAGATAAAACCAGCACAGTGGAGGCCTGTTTACCATTGGAATTAACCAAGAATGAGAGT
TGCCTAAATTCCAGAGAGACCTCTTTCATAACTAATGGGAGTTGCCTGGCCTCCAGAAAGACCTCTTT
TATGATGGCCCTGTGCCTTAGTAGTATTTATGAAGACTTGAAGATGTACCAGGTGGAGTTCAAGACCA
TGAATGCAAAGCTTCTGATGGATCCTAAGAGGCAGATCTTTCTAGATCAAAACATGCTGGCAGTTATT
GATGAGCTGATGCAGGCCCTGAATTTCAACAGTGAGACTGTGCCACAAAAATCCTCCCTTGAAGAACC
GGATTTTTATAAAACTAAAATCAAGCTCTGCATACTTCTTCATGCTTTCAGAATTCGGGCAGTGACTA
TTGATAGAGTGATGAGCTATCTGAATGCTTCCTAAAAACCGGCCCGGCCGGCCCCGCGGCCGCTCGAG
CCTAAGCTTCTAGATAAGATATCCGATCCACCGGATCTAGATAACTGATCATAATCAGCCATACCACA
TTTGTAGAGGTTTTACTTGCTTTAAAAAACCTCCCACACCTCCCCCTGAACCTGAAACATAAAATGAA
TGCAATTGTTGTTGTTAACTTGTTTATTGCAGCTTATAATGGTTACAAATAAAGCAATAGCATCACAA
ATTTCACAAATAAAGCATTTTTTTCACTGCATTCTAGTTGTGGTTTGTCCAAACTCATCAATGTATCT
TAGCGCCGGCGGGTCGACAGCCTAGTGGTACCCACGAGGTGGCAGGAGCTGCATCGATGTCGCTTCCT
CGCTCACTGACTCGCTGCGCTCGGTCGTTCGGCTGCGGCGAGCGGTATCAGCTCACTCAAAGGCGGTA
ATACGGTTATCCACAGAATCAGGGGATAACGCAGGAAAGAACATGTGAGCAAAAGGCCAGCAAAAGGC
CAGGAACCGTAAAAAGGCCGCGTTGCTGGCGTTTTTCCATAGGCTCCGCCCCCTGACGAGCATCACA
AAAATCGACGCTCAAGTCAGAGGTGGCGAAACCCGACAGGACTATAAAGATACCAGGCGTTTCCCCCT
GGAAGCTCCCTCGTGCGCTCTCCTGTTCCGACCCTGCCGCTTACCGGATACCTGTCCGCCTTTCTCCC
TTCGGGAAGCGTGGCGCTTTCTCATAGCTCACGCTGTAGGTATCTCAGTTCGGTGTAGGTCGTTCGCT
CCAAGCTGGGCTGTGTGCACGAACCCCCCGTTCAGCCCGACCGCTGCGCCTTATCCGGTAACTATCGT
CTTGAGTCCAACCCGGTAAGACACGACTTATCGCCACTGGCAGCAGCCACTGGTAACAGGATTAGCAG
AGCGAGGTATGTAGGCGGTGCTACAGAGTTCTTGAAGTGGTGGCCTAACTACGGCTACACTAGAAGGA
CAGTATTTGGTATCTGCGCTCTGCTGAAGCCAGTTACCTTCGGAAAAAGAGTTGGTAGCTCTTGATCC
GGCAAACAAACCACCGCTGGTAGCGGTGGTTTTTTTGTTTGCAAGCAGCAGATTACGCGCAGAAAAAA
AGGATCTCAAGAAGATCCTTTGATCTTTTCTACGGGGTCTGACGCTCAGTGGAACGAAAACTCACGTT
AAGGGATTTTGGTCATGAGATTATCAAAAAGGATCTTCACCTAGATCCTTTTAAATTAAAAATGAAGT
TTTAAATCAATCTAAAGTATATATGAGTAAACTTGGTCTGACAGTTACCAATGCTTAATCAGTGAGGC
ACCTATCTCAGCGATCTGTCTATTTCGTTCATCCATAGTTGCCTGACTCCCCACAGAGTGGCAGAGAC
TGCATTCGAAAACGTTTGAATTGATAATTATTATCATTTGCGGGTCAATTCTTAGAAAAACTCATCGA
GCATCAAATGAAACTGCAATTTATTCATATCAGGATTATCAATACCATATTTTTGAAAAAGCCGTTTC
TGTAATGAAGGAGAAAACTCACCGAGGCAGTTCCATAGGATTGCAAGATCCTGGTATCGGTCTGCGAT
TCCGACTCGTCCAACATCAATACAACCTATTAATTTCCCCTCGTCAAAAATAAGGTTATCAAGTGAGA
AATCACCATGAGTGACGACTGAATCCGGTGAGAATGGCAAAAGCTTATGCATTTCTTTCCAGACTTGT
```

*...Fig. 17 continued*

```
TCAACAGGCCAGCCATTACGCTCGTCATCAAAATCACTCGCATCAACCAAACCGTTATTCATTCGTGA
TTGCGCCTGAGCGAGACGAAATACGCGATCGCTGTTAAAAGGACAATTACAAACAGGAATCGAATGCA
ACCGGCGCAGGAACACTGCCAGCGCATCAACAATATTTTCACCTGAATCAGGATATTCTTCTAATACC
TGGAATGCTGTTTTCCCGGGGATCGCAGTGGTGAGTAACCATGCATCATCAGGAGTACGGATAAAATG
CTTGATGGTCGGAAGAGGCATAAATTCCGTCAGCCAGTTTAGTCTGACCATCTCATCTGTAACATCAT
TGGCAACGCTACCTTTGCCATGTTTCAGAAACAACTCTGGCGCATCGGGCTTCCCATACAATCGATAG
ATTGTCGCACCTGATTGCCCGACATTATCGCGAGCCATTTATACCCATATAAATCAGCATCCATGTT
GGAATTTAATCGCGGCCTCGAGCAAGACGTTTCCCGTTGAATATGGCTCATAACACCCCTTGTATTAC
TGTTTATGTAAGCAGACAGTTTTATTGTTCATGCGAAAACGTTTGAATTGATAATTATTATCATTTGC
GGGTCCTTTCCGGCGATCCGCCTTGTTACGGGGCGGCGACCTCGCGGGTTTTCGCTATTTATGAAAAT
TTTCCGGTTTAAGGCGTTTCCGTTCTTCTTCGTCATAACTTAATGTTTTTATTTAAAATACCCTCTGA
AAAGAAAGGAAACGACAGCTGAAAGCGAGCTTTTTGGCCTCTGTCGTTTCCTTTCTCTGTTTTTGTCC
GTGGAATGAACAATGGAAGTCGGCCTCGTGATACGCCTATTTTTATAGGTTAATGTCATGATAATAAT
GGTTTCTTAGCGATATTTAAATTAA
```

Figure 18: Schematic overview and nucleotide sequence of the expression cassette comprising CMV, human 4-1BBL, EMCV IRES, human IL-2, PV IRES, human scIL-12, and SV40polyA as contained in hu pE1.1 Im02 depicted in Figure 2 and in SEQ ID NO: 11 (Figure 17), respectively Schematic overview of the expression cassette comprising CMV, human 4-1BBL, EMCV IRES, human IL-2, PV IRES, human scIL-12, and SV40polyA as contained in shuttle vector hu pE1.1 Im02 depicted in Figure 2:

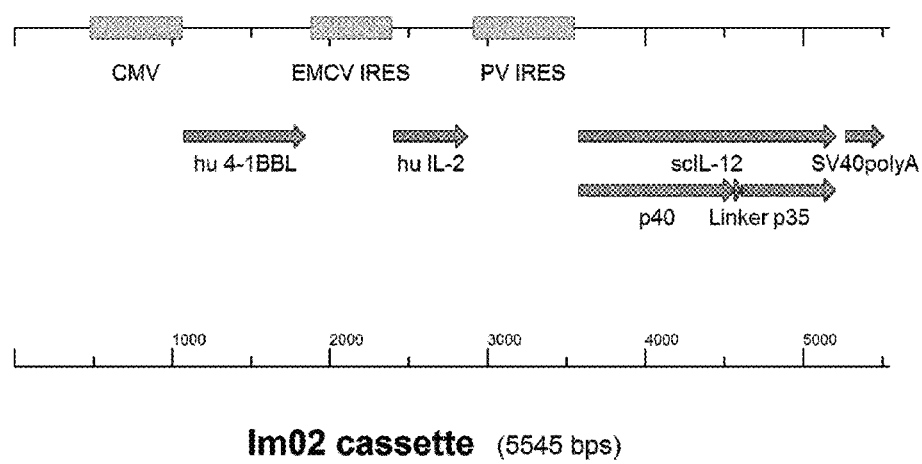

Im02 cassette (5545 bps)

...Figure 18 continued

SEQ ID NO: 12: Nucleotide sequence of the expression cassette comprising CMV, human 4-1BBL, EMCV IRES, human IL-2, PV IRES, human scIL-12, and SV40polyA as contained in shuttle vector hu pE1.1 Im02 depicted in Figure 2 and in SEQ ID NO: 11 (Figure 17), respectively (5,545 nucleotides; origin: artificial):

```
TAACATCATCAATAATATACCTTATTTTGGATTGAAGCCAATATGATAATGAGGGGGTGGAGTTTGTG
ACGTGGCGCGGGGCGTGGGAACGGGGCGGGTGACGTAGTAGTGTGGCGGAAGTGTGATGTTGCAAGTG
TGGCGGAACACATGTAAGCGACGGATGTGGCAAAAGTGACGTTTTTGGTGTGCGCCGGTGTACACAGG
AAGTGACAATTTTCGCGCGGTTTTAGGCGGATGTTGTAGTAAATTTGGGCGTAACCGAGTAAGATTTG
GCCATTTTCGCGGGAAAACTGAATAAGAGGAAGTGAAATCTGAATAATTTTGTGTTACTCATAGCGCG
TAATATTTGTCTAGGGAGATCTTCTAGACCCGGGAGCGGCCGGCCGCTGTCGACCGTAACTATAACGG
TCCTAAGGTAGCGAACCACGTCAGGTCGAGTGTTCATGAATGGAAGATATCTGCGCCCTAGCGCCGGC
GAGCTCTAGTAATCAATTACGGGGTCATTAGTTCATAGCCCATATATGGAGTTCCGCGTTACATAACT
TACGGTAAATGGCCCGCCTGGCTGACCGCCCAACGACCCCGCCCATTGACGTCAATAATGACGTATG
TTCCATAGTAACGCCAATAGGGACTTTCCATTGACGTCAATGGGTGGAGTATTTACGGTAAACTGCC
CACTTGGCAGTACATCAAGTGTATCATATGCCAAGTACGCCCCCTATTGACGTCAATGACGGTAAATG
GCCCGCCTGGCATTATGCCCAGTACATGACCTTATGGGACTTTCCTACTTGGCAGTACATCTACGTAT
TAGTCATCGCTATTACCATGGTGATGCGGTTTTGGCAGTACATCAATGGGCGTGGATAGCGGTTTGAC
TCACGGGGATTTCCAAGTCTCCACCCCATTGACGTCAATGGGAGTTTGTTTTGGCACCAAAATCAACG
GGACTTTCCAAAATGTCGTAACAACTCCGCCCCATTGACGCAAATGGGCGGTAGGCGTGTACGGTGGG
AGGTCTATATAAGCAGAGCTGGTTTAGTGAACCGTCAGATCCGCTAGACGGACCGACCATGGAATACG
CCTCTGACGCTTCACTGGACCCCGAAGCCCCGTGGCCTCCCGCGCCCCGCGCTCGCGCCTGCCGCGTA
CTGCCTTGGGCCCTGGTCGCGGGGCTGCTGCTGCTGCTGCTGCTCGCTGCCGCCTGCGCCGTCTTCCT
CGCCTGCCCCTGGGCCGTGTCCGGGGCTCGCGCCTCGCCCGGCTCCGCGGCCAGCCCGAGACTCCGCG
AGGGTCCCGAGCTTTCGCCCGACGATCCCGCCGGCCTCTTGGACCTGCGGCAGGGCATGTTTGCGCAG
CTGGTGGCCCAAAATGTTCTGCTGATCGATGGGCCCCTGAGCTGGTACAGTGACCCAGGCCTGGCAGG
CGTGTCCCTGACGGGGGCCTGAGCTACAAAGAGGACACGAAGGAGCTGGTGGTGGCCAAGGCTGGAG
TCTACTATGTCTTCTTTCAACTAGAGCTGCGGCGCGTGGTGGCCGGCGAGGGCTCAGGCTCCGTTTCA
CTTGCGCTGCACCTGCAGCCACTGCGCTCTGCTGCTGGGGCCGCCGCCCTGGCTTTGACCGTGGACCT
GCCACCCGCCTCCTCCGAGGCTCGGAACTCGGCCTTCGGTTTCCAGGGCCGCTTGCTGCACCTGAGTG
CCGGCCAGCGCCTGGGCGTCCATCTTCACACTGAGGCCAGGGCACGCCATGCCTGGCAGCTTACCCAG
GGCGCCACAGTCTTGGGACTCTTCCGGGTGACCCCCGAAATCCCAGCCGGACTCCCTTCACCGAGGTC
GGAATAAGAACGCTAGCTCTTGTGACTGGCGCGCCTGATCAATCGATGTTTAAACGTTATTTTCCACC
ATATTGCCGTCTTTTGGCAATGTGAGGGCCCGGAAACCTGGCCCTGTCTTCTTGACGAGCATTCCTAG
```

...*Fig. 18 continued*

```
GGGTCTTTCCCCTCTCGCCAAAGGAATGCAAGGTCTGTTGAATGTCGTGAAGGAAGCAGTTCCTCTGG
AAGCTTCTTGAAGACAAACAACGTCTGTAGCGACCCTTTGCAGGCAGCGGAACCCCCCACCTGGCGAC
AGGTGCCTCTGCGGCCAAAAGCCACGTGTATAAGATACACCTGCAAAGGCGGCACAACCCCAGTGCGA
CGTTGTGAGTTGGATAGTTGTGGAAAGAGTCAAATGGCTCTCCTCAAGCGTATTCAACAAGGGGCTGA
AGGATGCCCAGAAGGTACCCCATTGTATGGGATCTGATCTGGGGCCTCGGTGCACATGCTTTACGTGT
GTTTAGTCGAGGTTAAAAAAACGTCTAGGCCCCCCGAACCACGGGGACGTGGTTTTCCTTTGAAAAAC
ACGATTCTCGAGACTAGTCGTACGACCATGTACAGGATGCAACTCCTGTCTTGCATTGCACTAAGTCT
TGCACTTGTCACAAACAGTGCACCTACTTCAAGTTCTACAAAGAAAACACAGCTACAACTGGAGCATT
TACTGCTGGATTTACAGATGATTTTGAATGGAATTAATAATTACAAGAATCCCAAACTCACCAGGATG
CTCACATTTAAGTTTTACATGCCCAAGAAGGCCACAGAACTGAAACATCTTCAGTGTCTAGAAGAAGA
ACTCAAACCTCTGGAGGAAGTGCTAAATTTAGCTCAAAGCAAAAACTTTCACTTAAGACCCAGGGACT
TAATCAGCAATATCAACGTAATAGTTCTGGAACTAAAGGGATCTGAAACAACATTCATGTGTGAATAT
GCTGATGAGACAGCAACCATTGTAGAATTTCTGAACAGATGGATTACCTTTTGTCAAAGCATCATCTC
AACACTGACTTGAACGCGTGCTAGCAGGCCCGGCCGGCCTTGTTAAAGACAGGATGAAGCTTAAAACA
GCTCTGGGGTTGTACCCACCCCAGAGGCCCACGTGGCGGCTAGTACTCCGGTATTGCGGTACCCTTGT
\CGCCTGTTTTATACTCCCTTCCCGTAACTTAGACGCACAAAACCAAGTTCAATAGAAGGGGGTACAA
\CCAGTACCACCACGAACAAGCACTTCTGTTTCCCCGGTGATGTCGTATAGACTGCTTGCGTGGTTGA
\AGCGACGGATCCGTTATCCGCTTATGTACTTCGAGAAGCCCAGTACCACCTCGGAATCTTCGATGCG
fTGCGCTCAGCACTCAACCCCAGAGTGTAGCTTAGGCTGATGAGTCTGGACATCCCTCACCGGTGACG
GTGGTCCAGGCTGCGTTGGCGGCCTACCTATGGCTAACGCCATGGGACGCTAGTTGTGAACAAGGTGT
GAAGAGCCTATTGAGCTACATAAGAATCCTCCGGCCCTGAATGCGGCTAATCCCAACCTCGGAGCAG
GTGGTCACAAACCAGTGATTGGCCTGTCGTAACGCGCAAGTCCGTGGCGGAACCGACTACTTTGGGTG
TCCGTGTTTCCTTTTATTTTATTGTGGCTGCTTATGGTGACAATCACAGATTGTTATCATAAAGCGAA
TTGGATTGCGTACGCGGACCGAACTAGTTTCGCCGCCTCCAACATGTGTCACCAGCAGTTGGTCATCT
CTTGGTTTTCCCTGGTTTTTCTGGCATCTCCCCTCGTGGCCATATGGGAACTGAAGAAAGATGTTTAT
GTCGTAGAATTGGATTGGTATCCGGATGCCCCTGGAGAAATGGTGGTCCTCACCTGTGACACCCCTGA
AGAAGATGGTATCACCTGGACCTTGGACCAGAGCAGTGAGGTCTTAGGCTCTGGCAAAACCCTGACCA
TCCAAGTCAAAGAGTTTGGAGATGCTGGCCAGTACACCTGTCACAAAGGAGGCGAGGTTCTAAGCCAT
TCGCTCCTGCTGCTTCACAAAAGGAAGATGGAATTTGGTCCACTGATATTTAAAGGACCAGAAAGA
ACCCAAAAATAAGACCTTTCTAAGATGCGAGGCCAAGAATTATTCTGGACGTTTCACCTGCTGGTGGC
TGACGACAATCAGTACTGATTTGACATTCAGTGTCAAAAGCAGCAGAGGCTCTTCTGACCCCCAAGGG
GTGACGTGCGGAGCTGCTACACTCTCTGCAGAGAGAGTCAGAGGGGACAACAAGGAGTATGAGTACTC
AGTGGAGTGCCAGGAGGACAGTGCCTGCCCAGCTGCTGAGGAGAGTCTGCCCATTGAGGTCATGGTGG
ATGCCGTTCACAAGCTCAAGTATGAAAACTACACCAGCAGCTTCTTCATCAGGGACATCATCAAACCT
GACCCACCCAAGAACTTGCAGCTGAAGCCATTAAAGAATTCTCGGCAGGTGGAGGTCAGCTGGGAGTA
CCCTGACACCTGGAGTACTCCACATTCCTACTTCTCCCTGACATTCTGCGTTCAGGTCCAGGGCAAGA
```

*...Fig. 18 continued*

```
GCAAGAGAGAAAAGAAAGATAGAGTCTTCACGGACAAGACCTCAGCCACGGTCATCTGCCGCAAAAAT
GCCAGCATTAGCGTGCGGGCCCAGGACCGCTACTATAGCTCATCTTGGAGCGAATGGGCATCTGTGCC
CTGCAGTGGTGGCGGTGGAAGCGGCGGTGGCGGAAGCGGCGGTGGCGGCAGCAGAAACCTCCCCGTGG
CCACTCCAGACCCAGGAATGTTCCCATGCCTTCACCACTCCCAAAACCTGCTGAGGGCCGTCAGCAAC
ATGCTCCAGAAGGCCAGACAAACTCTAGAATTTTACCCTTGCACTTCTGAAGAGATTGATCATGAAGA
TATCACAAAAGATAAAACCAGCACAGTGGAGGCCTGTTTACCATTGGAATTAACCAAGAATGAGAGTT
GCCTAAATTCCAGAGAGACCTCTTTCATAACTAATGGGAGTTGCCTGGCCTCCAGAAAGACCTCTTTT
ATGATGGCCCTGTGCCTTAGTAGTATTTATGAAGACTTGAAGATGTACCAGGTGGAGTTCAAGACCAT
GAATGCAAAGCTTCTGATGGATCCTAAGAGGCAGATCTTTCTAGATCAAAACATGCTGGCAGTTATTG
ATGAGCTGATGCAGGCCCTGAATTTCAACAGTGAGACTGTGCCACAAAAATCCTCCCTTGAAGAACCG
GATTTTTATAAAACTAAAATCAAGCTCTGCATACTTCTTCATGCTTTCAGAATTCGGGCAGTGACTAT
TGATAGAGTGATGAGCTATCTGAATGCTTCCTAAAAACCGGCCCGGCCGGCCCCGCGGCCGCTCGAGC
CTAAGCTTCTAGATAAGATATCCGATCCACCGGATCTAGATAACTGATCATAATCAGCCATACCACAT
TTGTAGAGGTTTTACTTGCTTTAAAAAACCTCCCACACCTCCCCCTGAACCTGAAACATAAAATGAAT
GCAATTGTTGTTGTTAACTTGTTTATTGCAGCTTATAATGGTTACAAATAAAGCAATAGCATCACAAA
TTTCACAAATAAAGCATTTTTTTCACTGCATTCTAGTTGTGGTTTGTCCAAACTCATCAATGTATCTT
AGCGCCGGCGGGTCGACAGCCTAGTGGTACCCACGAG
```

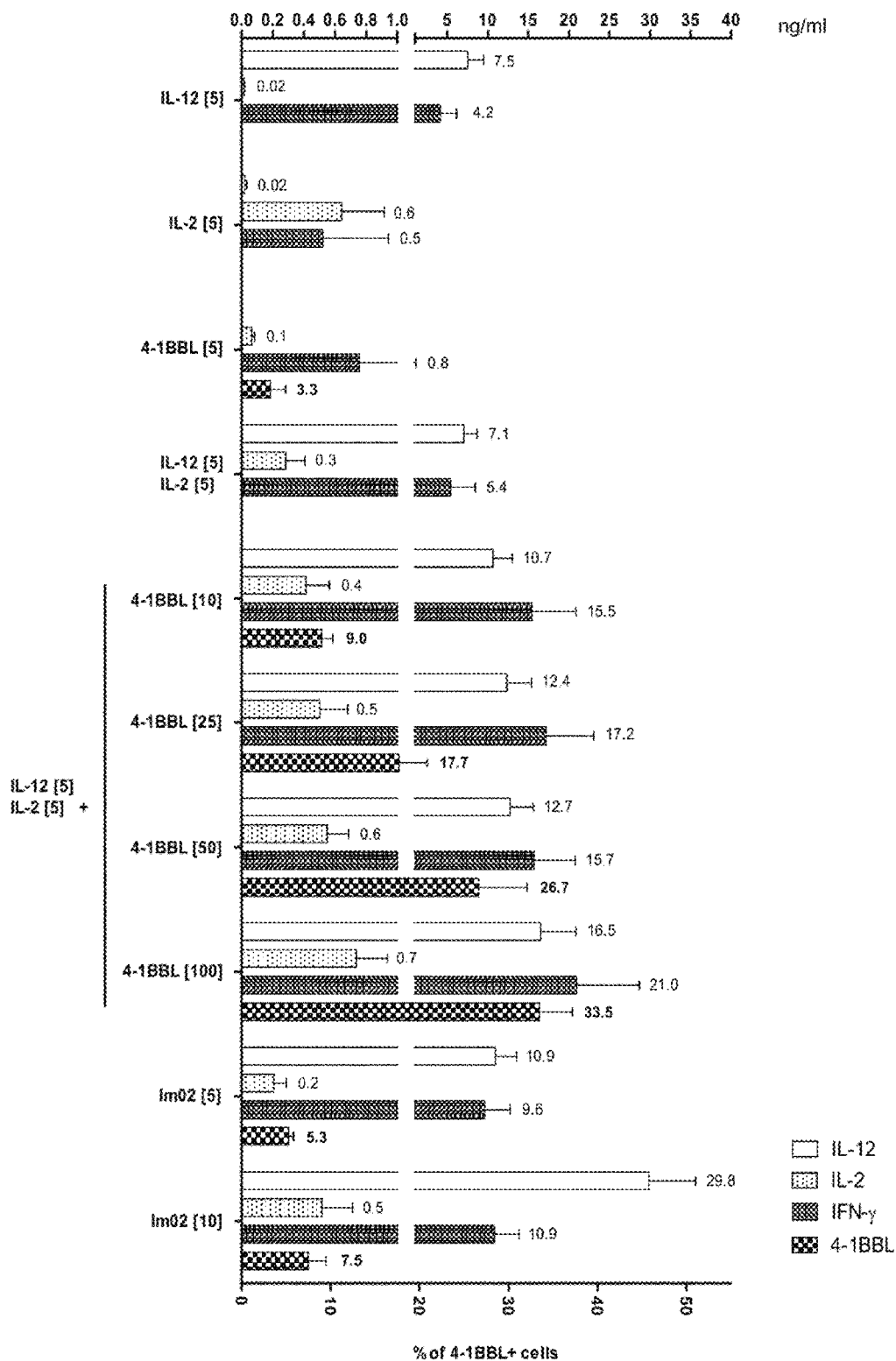
Figure 19: Transgene expression of 4-1BBL, IL-2, and scIL-12 of Im02 and of single-gene expressing vectors at different MOI, and IFN-γ response Figure 20: Schematic gene map of shuttle plasmid pE1.1 lm01
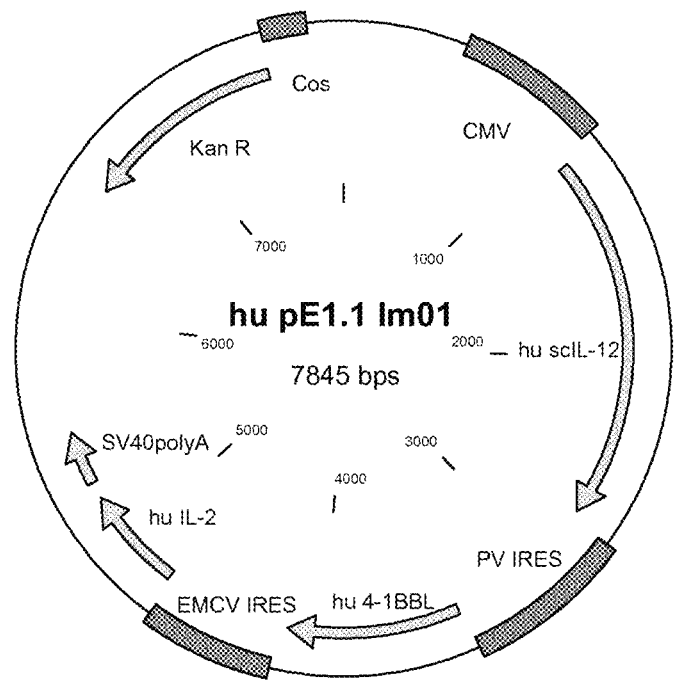

IMMUNOSTIMULATING VECTOR SYSTEM

CROSS-REFERENCE TO RELATED APPLICATIONS

This patent application is a divisional application of pending U.S. patent application Ser. No. 16/079,331, filed Aug. 23, 2018, which is the U.S. national phase of International Patent Application No. PCT/EP2017/054216, filed on Feb. 23, 2017, which claims the benefit of European Application No. 16157423.1, filed Feb. 25, 2016, the disclosures of which are incorporated herein by reference in their entireties.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 38,217 bytes ASCII (Text) file named "752005_ST25.txt," created Apr. 1, 2021.

TECHNICAL FIELD

The present disclosure relates generally to the field of immunology, and more specifically to the field of immunotherapy. In particular, the present disclosure relates to a novel vector system for immunostimulation and methods of using same in immunotherapy. The novel vector system is characterized by one or more vectors comprising nucleic acid sequences encoding 4-1BB ligand (4-1BBL, CD137 ligand), single chain IL-12 (scIL-12) and IL-2.

BACKGROUND

The immune system provides the means for recognizing and destroying foreign invaders, such as bacteria or viruses, as well as damaged, diseased, or abnormal cells in the body, including cancer cells. Primary players in immune system responses include macrophages and natural killer cells, which provide a general, or nonspecific, level of immune protection. Other cell types, including cytotoxic T lymphocytes (CTLs) and B lymphocytes, act against specific targets. Immune responses include humoral responses, in which B cells produce antigen-specific antibodies, and cell-mediated responses, in which antigens or antigen-bearing cells are recognized and destroyed by various types of T cells by using a variety of different mechanisms. Cell-mediated immune responses including a CTL response are considered to be key to the elimination of tumor cells and virus-infected cells.

It is generally believed that the natural capacity of the immune system to detect and destroy abnormal cells prevents the development of many cancers. Nevertheless, some cancer cells have developed strategies to evade destruction by the immune system. For example, several different mechanisms exist which cancer cells can use to suppress immune responses. They can also undergo genetic changes that lead to the loss of cancer-associated antigens, making them less "visible" to the immune system. Similar considerations apply with respect to different viruses, which have also adopted immune evasion strategies, leading to a failure of the host's immune system to control viral infection.

The goal of immunotherapy is to overcome these barriers to an effective immune response. Immunotherapy-based biological therapies restore or increase the activities of specific immune-system components or counteract immunosuppressive signals produced by cancer cells or during viral infectious diseases. Tumor cells, among others, are killed by CTLs in an antigen-specific manner. Thus, agents that promote T-cell activation and impart strong cytolytic and inflammatory properties are ideal candidates for enhancing tumor-specific immunity.

New forms of therapy continue to be needed, and one major avenue of immunotherapeutics is based on gene transfer technology. Gene therapy has been established as a way to deliver immune therapy. Non-replicating viruses and viral vectors were originally proposed 20 years ago as anticancer agents using, inter alia, immune activating (e.g., IL-2) modalities (see, for example, Crofts and Krimsky, 2005, Hum Gene Ther. 16: 169-177). WO 2004/035799 describes an adenoviral vector comprising nucleic acid sequences, which code for single chain IL-12 (scIL-12), the costimulatory protein 4-1BB ligand (4-1BBL), and IL-2, for gene therapy in the treatment of infectious diseases and cancer.

The present disclosure relates to a novel vector-based immunotherapy, which represents an improvement over prior gene therapy approaches effective for converting an inactive into an active immune microenvironment and thereby treating cancer and viral infections.

SUMMARY OF THE DISCLOSURE

The present disclosure provides a vector comprising nucleic acid sequences of genes encoding 4-1BB ligand (4-1BBL), single chain IL-12 (scIL-12) and IL-2, wherein the vector provides for an increased expression of 4-1BBL as compared to the expression levels of scIL-12 and IL-2. Specifically, the nucleic acid sequences encoding 4-1BBL, scIL-12 and IL-2 are organized in the vector in 5' to 3' orientation in a sequential order 1, 2, 3, with the proviso that the gene encoding scIL-12 is not at position 1. The present disclosure also provides methods and uses of the novel vector for converting an inactive into an active immune microenvironment and thereby treating cancer or infectious diseases. Methods and compositions of the present disclosure include the construction and verification of the claimed viral vector that elicits an immune response against cancer cells and viral infections to enhance and/or stimulate immunity against cancer and viral infections.

Aspects of the disclosure include:

1. Vector comprising nucleic acid sequences encoding 4-1BB ligand (4-1BBL), single chain IL-12 (scIL-12) and IL-2, and further comprising at least one regulatory nucleic acid sequence, preferably a promoter sequence, providing for an increased expression level of 4-1BBL as compared to the expression levels of scIL-12 and IL-2.

2. The vector of item 1, wherein the expression level of 4-1BBL is increased as compared to the expression level of 4-1BBL obtained by the expression construct of vector Im01 (FIG. 20).

3. The vector of item 1 or 2, wherein the expression level of scIL-12 is decreased and/or the expression level of IL-2 is increased as compared to the expression levels of scIL-12 and/or IL-2 obtained by the expression construct of vector Im01 (FIG. 20).

4. The vector of any one of items 1 to 3, wherein the nucleic acid sequences encoding 4-1BBL, scIL-12 and IL-2 are organized in 5' to 3' orientation in a sequential order 1, 2, 3, with the proviso that the nucleic acid sequence encoding scIL-12 is not at position 1.

5. The vector of any one of items 1 to 4, wherein the vector is any one of an adenoviral vector, an adeno-associated virus vector, a lentiviral vector, a herpes simplex virus vector, a pox virus vector, an RNA vector, a plasmid vector, a nanoparticle vector, and naked DNA.

6. The vector of any one of items 1 to 5, wherein the nucleic acid sequence encoding 4-1BBL is human cDNA, the nucleic acid sequence encoding scIL-12 is human cDNA, and/or the nucleic acid sequence encoding IL-2 is human cDNA.

7. The vector of any one of items 1-6, wherein the nucleic acid sequence encoding 4-1BBL shows at least 70% sequence identity to the nucleic acid sequence of SEQ ID NO: 1, wherein the variant nucleic acid sequence encodes a 4-1BBL protein capable of specifically binding activated T cells.

8. The vector of any one of items 1-6, wherein the nucleic acid sequence encoding IL-2 shows at least 70% sequence identity to the nucleic acid sequence of SEQ ID NO: 3, wherein the variant nucleic acid sequence encodes an IL-2 protein having immune stimulating activity.

9. The vector of any one of items 1-6, wherein the nucleic acid sequence encoding scIL-12 shows at least 70% sequence identity to the nucleic acid sequence of SEQ ID NO: 5, wherein the variant nucleic acid sequence encodes a scIL-12 protein having immune stimulating activity.

10. The vector of any one of items 1-9, wherein the nucleic acid sequences encoding scIL-12 and IL-2 are located downstream of the nucleic acid sequence encoding 4-1BBL.

11. The vector of item 10, wherein the nucleic acid sequence encoding IL-2 is located downstream of the nucleic acid sequence encoding 4-1BBL, and the nucleic acid sequence encoding scIL-12 is located downstream of the nucleic acid sequence encoding IL-2.

12. The vector of item 10 or 11, wherein a promoter is located upstream of the nucleic acid sequence encoding 4-1BBL, but not upstream of the nucleic acid sequences encoding scIL-12 and/or IL-2.

13. The vector of any one of items 1-12, wherein the nucleic acid sequences encoding 4-1BBL, scIL-12 and IL-2 are linked by internal ribosomal entry sites (IRES).

14. A cancer cell or an immune cell, transduced or transfected with the vector of any one of items 1-13.

15. A medicament comprising the vector of any one of items 1-13 or the cancer or immune cell of item 14.

16. The vector of any one of items 1-13, the cancer or immune cell of item 14, or the medicament of item 15, for use in, or for use in a method of, treating cancer, a viral infection and/or an immune system disorder.

17. The vector for use according to item 16, or the cancer or immune cell for use according to item 16, or the medicament for use according to item 16, wherein the cancer is any one of bladder cancer, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, mesothelioma, osteogenic sarcoma, primary macro globulinemia, and retinoblastoma.

18. The vector of any one of items 1-13, or the cancer or immune cell of item 14, or the medicament of item 15, for use in, or for use in a method of, preventing or treating cancer metastasis.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

FIG. 1 shows a comparison of transgene expression of IL-12, IL-2 and 4-1BBL and IFN-γ response of murine and human Im01. MOI (multiplicity of infection) numbers indicated in [brackets]; "m"=murine; "hu"=human.

FIG. 2 shows a schematic gene map of the shuttle plasmid pE1.1 Im02. The cDNAs of the three therapeutic genes of human 4-1BBL (CD137L), IL-2 and single-chain IL-12 are organized in a tricistronic construct linked by internal ribosomal entry sites (IRES) and driven by a Cytomegalovirus (CMV) promoter. Transcript polyadenylation is induced by a SV40 derived signal. The expression cassette for Im02 is illustrated as a precursor transfer plasmid based on plasmid pE1.1, suitable for sub-cloning into a plasmid carrying, e.g., adenoviral vector DNA.

FIG. 3 shows a comparison of transgene expression and IFN-γ response of Im02 and the earlier vector Im01. MOI (multiplicity of infection) numbers indicated in [brackets]. Indicated data points are the mean of four individual donors each with four replicates.

FIG. 4 shows a comparison of Im02 and Im01 in a bladder tissue-based model. "T"=bladder tumor tissue; "B"=normal bladder tissue.

FIG. 5 shows a comparison of Im02 and Im01 at different dose levels. Dosis ivp means dosis of infectious virus particles. "T"=bladder tumor tissue; "B"=normal bladder tissue.

FIG. 6 shows a heat-plot illustrating the activation of immune cell types in a co-culture of human bladder RT-4 carcinoma cells with human PBMCs. Subsequent rows show basic and activated ("act") immune cell types. RT-4 cells without vector ("control") and cells transduced with an empty adenovirus vector ("Ad0") were used as controls. Th=T helper cells; Tc=cytotoxic T cells (CD8+ T cells); PC=plasma cells; NK=natural killer cells; mono=monocytes; DC=dendritic cells; neutro=neutrophils.

FIG. 7 shows histologic examination after Hematoxylin and Eosin staining of samples stimulated with Im02 or Ad0 or without treatment as control. A: Bladder tumor tissue without culture; B: Bladder tumor tissue, $10^8$ ivp Ad0, 6 days after treatment; C: Bladder tumor tissue, $10^8$ ivp Im02, 6 days after treatment.

FIG. 8 shows histological examination after Hematoxylin and Eosin staining of samples stimulated with or without Im02. Upper panel: Urothelial tumor tissue without culture, lower panel: Bladder tumor tissue, stimulated with $10^8$ ivp Im02, 6 days after treatment.

FIG. 9 shows target cell analysis and uptake mechanism by transmission electron microscopy. Panel 1: Overview (right image), and Detail (A): particle uptake without vesicle by an unknown cell type. Detail (B), white: vesicular particle uptake by a cell of Langerhans cell/macrophage/dendritic cell morphology. Panel 2: Overview (B) and Detail (A): vesicular adenoviral particle uptake by a cell of Langerhans cell/macrophage/dendritic cell morphology. Panel 3: Overview (B) and Detail (A): Adenoviral particle uptake by a strong vesicular structure by a cell of lymphocyte morphology. Panel 4: Overview (B) and Detail (A): Adenoviral particle uptake without vesicle by a cell of fibroblast morphology. Panel 5: Overview (B) and Detail (A): Large groups of adenoviral particles without vesicle taken up by an unknown target cell type. Panel 6: Overview: Adenoviral particles without vesicle coating (white arrows) between abundant vesicular structures in a target cell with morphological features of an epithelial or tumor cell. Detail (A): Early endocytosis figure of an adenoviral particle attached to the plasma membrane. Detail (B): Pinocytosis of an adenoviral particle in a large vesicle containing also other non-viral structures.

FIG. 10 shows a comparison of differential expression in normal bladder and bladder tumor samples. Im02 means the adenoviral vector as described in Example 2. Ad0 means empty adenoviral vector, used as control. n=number of bladder/tumor samples.

FIG. 11 shows the examination of different transfectants in cell culture. GFP=green fluorescent protein. CAR=Coxsackie-Adenovirus-Receptor. MOI=multiplicity of infection (infectious viral particles per target cell).

FIG. 12 shows effects of protamine sulfate on transgene expression and IFN-γ induction. Im02 means the adenoviral vector as described in Example 2; Ad0=empty adenoviral vector, used as a control. ivp=infectious viral particles. "T"=bladder tumor tissue; "B"=normal bladder tissue.

FIG. 13 shows the nucleotide and amino acid sequence of human 4-1BBL (CD137L).

FIG. 14 shows the nucleotide and amino acid sequence of human IL-2.

FIG. 15 shows the nucleotide and amino acid sequence of human single-chain IL-12 (scIL-12) comprising the p40 and p35 subunits of human IL-12 linked by a linker. The linker sequence is shown in boldface and underlined in SEQ ID NO: 5 and 6, respectively.

FIG. 16 shows the nucleotide and amino acid sequences of the 35 kDa and 40 kDa subunits of human IL-12.

FIG. 17 shows the nucleotide sequence (SEQ ID NO: 11) of the shuttle vector hu pE1.1 Im02 depicted in FIG. 2. The nucleotide sequence has a total of 7,845 bp. The CMV promoter, human 4-1BBL, EMCV IRES, human IL-2, PV IRES, human scIL-12, and SV40polyA can be identified in the nucleotide sequence of SEQ ID NO: 11 as follows: CMV promoter: bp 484-1,059; human 4-1BBL: bp 1,080-1,844; EMCV IRES: bp 1,885-2,388; human IL-2: bp 2,409-2,870; PV IRES: bp 2,914-3,545; human scIL-12: p40 subunit bp 3,581-4,564, linker bp 4,565-4,609, p35 subunit bp 4,610-5,203; and SV40polyA: bp 5,271-5,510.

FIG. 18 shows a schematic overview and the nucleotide sequence of the expression cassette comprising CMV, human 4-1BBL, EMCV IRES, human IL-2, PV IRES, human scIL-12, and SV40polyA as contained in the shuttle plasmid hu pE1.1 Im02 depicted in FIG. 2 and in SEQ ID NO: 11 (FIG. 17), respectively.

FIG. 19 shows transgene expression of 4-1BBL, IL-2, and scIL-12 of Im02 and of single-gene expressing vectors at different MOI, and IFN-γ response. The axis at the bottom designated "% of 4-1BBL+ cells" means cells that are positive for expression of 4-1BBL. The bar on the left-hand side indicates the combination of IL-12 and IL-2, each at [5] MOI, with different MOIs of 4-1BBL ([10], [25], [50], and [100]). Im02 means the adenoviral vector as described in Example 2. MOI=multiplicity of infection (i.e., infectious virus particles per target cell). Transgene expression of 4-1BBL, IL-2 and scIL-12, and IFN-γ response of Im02, and combinations of single-gene expressing vectors reveal that IFN-γ expression is dependent on increasing 4-1BBL levels.

FIG. 20 shows a schematic gene map of the shuttle plasmid pE1.1 Im01. The cDNAs of the three therapeutic genes of human 4-1BBL (CD137L), IL-2 and single-chain IL-12 are organized in a tricistronic construct linked by internal ribosomal entry sites (IRES) and driven by a Cytomegalovirus (CMV) promoter. Transcript polyadenylation is induced by a SV40 derived signal. The expression cassette for Im01 is illustrated as a precursor transfer plasmid based on plasmid pE1.1, suitable for sub-cloning into a plasmid carrying, e.g., adenoviral vector DNA.

DETAILED DESCRIPTION OF THE DISCLOSURE

As used herein and in the appended claims, the singular forms "a", "and", and "the" include plural referents unless the context clearly dictates otherwise. Thus, for example, reference to "an antigen" includes a plurality of such antigens, and reference to "a cell" or "the cell" includes reference to one or more cells and equivalents thereof (e.g., plurality of cells) known to those skilled in the art, and so forth. Similarly, reference to "a compound" or "a composition" includes a plurality of such compounds or compositions, and refers to one or more compounds or compositions, respectively, unless the context clearly dictates otherwise. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The term "codon optimized sequences" generally refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as "expression enhanced sequences".

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. The regulatory sequence may be homologous or heterologous to the desired gene sequence. For example, a wide range of promoters may be utilized, including viral or mammalian promoter as described herein. The promoter is oriented relative to a DNA sequence such that it is capable of initiating transcription of the said DNA sequence. The term "regulatory nucleic acid sequence" refers collectively to promoter sequences, polyadenylation signals, transcription termination sequences, upstream regulatory domains, origins of replication, enhancers and the like, which collectively provide for the replication, transcription and translation of a coding sequence in a recipient cell. Not all of these control sequences need always be present so long as the selected coding sequence is capable of being replicated, transcribed and translated in an appropriate host cell. One skilled in the art can readily identify regulatory nucleic acid sequence from public databases and materials. Furthermore, one skilled in the art can identify a regulatory sequence that is applicable for the intended use, for example, in vivo, ex vivo, or in vitro. Preferably, the term "regulatory nucleic acid sequence" refers to a promoter or promoter sequence.

In various embodiments, the term "regulatory nucleic acid sequence" also refers to IRES sequences (internal ribosomal entry sites). This applies in particular to various preferred embodiments, in which the term "regulatory nucleic acid sequences" encompasses one promoter per tricistronic expression cassette/vector containing the nucleic acid sequences encoding 4-1BBL, scIL-12 and IL-2, and further encompasses an IRES sequence for each cistron that is not localized immediately downstream of the promoter. The combination of a promoter and IRES sequences is considered, and has been demonstrated, to provide for an improved expression level or expression rate of 4-1BBL as compared to the expression levels or expression rates of IL-2 and scIL-12 in a tricistronic expression cassette/vector containing the nucleic acid sequences encoding 4-1BBL, IL-2 and scIL-12 (in this order) with a promoter for 4-1BBL, and IRES sequences for IL-2 and scIL-12.

The phrases "operatively positioned," "operatively linked," "under control" and "under transcriptional control" mean that a promoter is in a correct functional location and/or orientation in relation to a nucleic acid sequence to control transcriptional initiation and/or expression of that sequence. A promoter may or may not be used in conjunction with an "enhancer", which refers to a cis-acting regulatory sequence involved in the transcriptional activation of a nucleic acid sequence.

WO 2004/035799 describes an adenoviral vector comprising an expression construct comprising the genes for mouse/human single-chain IL-12 (scIL-12), 4-1BB ligand (4-1BBL), and IL-2 in this order in 5' to 3' orientation, i.e., the gene encoding scIL-12 at position 1, the gene encoding 4-1BBL at position 2, and the gene encoding IL-2 at position 3. This expression construct is shown in FIG. 1 of WO 2004/035799, and the corresponding vector was named "Ad-3". In the present disclosure, the internal vector code for the said earlier vector "Ad-3" is "Im01", see also Example 1 of the present disclosure.

Transgene expression of scIL-12, 4-1BBL, and IL-2 of murine and human Im01 has revealed that the expression level of the transgenes clearly varies between murine and human species, as shown in Example 1 and FIG. 1 of the present disclosure. Notably, expression of Im01 carrying the genes of human scIL-12, human 4-1BBL, and human IL-2 ("human Im01" or "hu Im01") resulted in a marked increase in IL-12 as compared to expression of Im01 carrying the genes of mouse scIL-12, mouse 4-1BBL, and mouse IL-2 ("mouse Im01" or "m Im01"). Thus, despite the same vector architecture of mouse and human Im01 as regards the organization of the order of the genes of scIL-12, 4-1BBL, and IL-2, marked differences in the expression level of the transgenes were observed. At least some of these differences in transgene expression between mouse and human Im01 were completely unexpected.

The vector provided by the present disclosure comprises a new architecture as regards the three genes encoding scIL-12, 4-1BBL, and IL-2. The novel vector provides for an increased expression of 4-1BBL as compared to the expression levels of scIL-12 and IL-2. In particular, the vector provided by the present disclosure comprises an expression cassette, wherein the three nucleic acid sequences (or the three genes) encoding scIL-12, 4-1BBL, and IL-2 are organized in 5' to 3' orientation in a sequential order 1, 2, and 3, with the proviso that the gene encoding scIL-12 is not at position 1. This novel vector architecture provides for, inter alia, an increased expression of 4-1BBL as compared to the arrangement of the same genes in human Im01, concurrent with a decrease of IL-12. Surprisingly, it has been found that this novel vector architecture leads to an increase in IFN-γ response (see Example 3 and FIG. 3 and Example 11 and FIG. 19 of the present disclosure). The surprising effects provided for by the novel vector of the present disclosure have been proven to be particularly beneficial for immunotherapy of patients in need of such therapy. Specifically, it has been shown that the vector of the present disclosure is particularly effective for converting an inactive into an active immune microenvironment, thereby treating cancer or viral infections. Therefore, the vector of the present disclosure is particularly suitable for use in cancer immunotherapy. For example, FIGS. 4 and 5 of the present disclosure demonstrate that the vector of the present disclosure exhibits an improved effect in immunostimulation in the tumor microenvironment as compared to the earlier vector Im01, as explained in corresponding Examples 4 and 5. Furthermore, a transcriptome analysis has shown that the therapeutic gene expression profile of the vector of the present disclosure is unique and superior, in particular superior over that of the earlier vector Im01 (see Example 6 and Tables 1 and 2). In addition, as shown in FIG. 6, gene expression analysis of the activation of major immune cell types has shown that the activation of T helper cells and cytotoxic T cells (CD8+ T cells) by the vector of the present disclosure is superior over the activation of the same immune cells by the earlier vector Im01 (see Example 7).

The novel vector of the present disclosure comprises three genes encoding 4-1BB ligand (4-1BBL), single-chain IL-12 (sc-IL12), and IL-2, wherein the said genes are organized in 5' to 3' orientation such that the gene encoding scIL-12 is not at the most upstream position of the said three genes. Thus, the novel vector of the present disclosure comprises three genes encoding 4-1BB ligand (4-1BBL), single-chain IL-12 (sc-IL12), and IL-2, wherein the said genes are organized in 5' to 3' orientation in a sequential order 1, 2, and 3, with the proviso that the gene encoding scIL-12 is not at position 1. More specifically, the vector comprises nucleic acid sequences of genes encoding 4-1BBL, sc-IL12, and IL-2, wherein the said genes are organized in 5' to 3' orientation in a sequential order 1, 2, and 3, with the proviso that the gene encoding scIL-12 is not at position 1. More specifically, the vector comprises nucleic acid sequences of genes encoding 4-1BBL, sc-IL12, and IL-2, wherein the said nucleic acid sequences of the said genes are organized in 5' to 3' orientation in a sequential order 1, 2, and 3, with the proviso that the nucleic acid sequence of the gene encoding scIL-12 is not at position 1.

In various embodiments of the present disclosure, the novel vector comprises an expression construct (or expression cassette) comprising three genes (more specifically nucleic acid sequences of three genes) encoding 4-1BB ligand (4-1BBL), single-chain IL-12 (sc-IL12), and IL-2, wherein the said genes are organized in the expression cassette such that the gene encoding scIL-12 is not at the most upstream position of the expression cassette. The most upstream position of the expression cassette may be more specifically described as the position at the 5' end of the expression cassette. Also, the most upstream position of the expression cassette may be more specifically described as the position immediately downstream of a promoter regulating transcription of the three genes of the expression cassette. The promoter may be a promoter that is part of the expression cassette, or a promoter upstream of the expression cassette. The organization of the three transgenes (i.e., the three genes encoding 4-1BBL, sc-IL12, and IL-2) in the expression cassette may be more specifically described to the effect that the nucleic acid sequences of the said three genes are organized in 5' to 3' orientation in a sequential order 1, 2, and 3, with the proviso that the nucleic acid sequence of the gene encoding scIL-12 is not at position 1 of the three genes of the expression cassette.

In various embodiments of the present disclosure, the novel vector of the present disclosure comprises an expression construct (or expression cassette) comprising three genes encoding 4-1BB ligand (4-1BBL), single-chain IL-12 (sc-IL12), and IL-2, wherein the said genes are organized in 5' to 3' orientation in a sequential order 1, 2, and 3, with the proviso that the gene encoding scIL-12 is not at position 1. More specifically, the vector comprises an expression construct (or expression cassette) comprising nucleic acid sequences of genes encoding 4-1BBL, sc-IL12, and IL-2, wherein the said genes are organized in 5' to 3' orientation in a sequential order 1, 2, and 3, with the proviso that the gene encoding scIL-12 is not at position 1. More specifically, the vector comprises an expression construct (or expression cassette) comprising nucleic acid sequences of genes encoding 4-1BBL, sc-IL12, and IL-2, wherein the said nucleic acid sequences of the said genes are organized in 5' to 3' orientation in a sequential order 1, 2, and 3, with the proviso that the nucleic acid sequence of the gene encoding scIL-12 is not at position 1. In various embodiments, the expression cassette or expression construct of the present disclosure comprises a promoter. The promoter may be more specifically described as promoter regulating transcription of the expression cassette (or expression construct). In various embodiments, the expression cassette comprises one promoter that is located upstream of (or at the 5' end of) the expression cassette (or upstream of the 5' end of the expression cassette).

As described herein, the "position 1" of the proviso clause mentioned above may be more specifically described as position 1 of the said sequential order 1, 2, and 3.

In various embodiments, organization of the three genes encoding scIL-12, 4-1BBL, and IL-2 in 5' to 3' orientation means organization of the three genes encoding scIL-12, 4-1BBL, and IL-2 in 5' to 3' orientation relative to the expression cassette or expression construct of the present disclosure comprising the three genes encoding 4-1BB ligand (4-1BBL), single-chain IL-12 (sc-IL12), and IL-2. Thus, 5' to 3' orientation refers to the 5' to 3' orientation of the expression cassette (or expression construct) or the promoter of the expression cassette.

In various other embodiments of the present disclosure, organization of the three genes encoding scIL-12, 4-1BBL, and IL-2 in 5' to 3' orientation means organization of the three genes encoding scIL-12, 4-1BBL, and IL-2 in 5' to 3' orientation relative to a promoter, which is not part of the expression cassette (or expression construct) of the disclosure, but which is located upstream of the expression cassette (or expression construct), i.e., upstream of the 5' end of the expression cassette (or expression construct). Here, 5' to 3' orientation refers to the 5' to 3' orientation of the promoter upstream of the 5' end of the expression cassette (or expression construct). The promoter located upstream of the expression cassette (or upstream of the 5' end of the expression cassette) may be more specifically described as the promoter regulating transcription of the expression cassette (or expression construct).

Also, 5' to 3' orientation may refer to the 5' to 3' orientation of the promoter upstream of that gene of the three transgenes of the present disclosure (i.e., encoding scIL-12, 4-1BBL, and IL-2), which is at the most upstream position of the said three transgenes.

The vector provided by the present disclosure comprises a new architecture as regards the three genes encoding scIL-12, 4-1BBL, and IL-2 which can also be described to the effect that the said three genes are organized in 5' to 3' orientation in a sequential order 1, 2, and 3, with the proviso that the gene encoding scIL-12 is not at position 1, wherein said position 1 is downstream of a promoter, in particular downstream of a promoter for expression of the said three genes. Thus, with respect to the expression cassette (or expression construct) of the present disclosure comprising the three genes encoding 4-1BB ligand (4-1BBL), single-chain IL-12 (sc-IL12), and IL-2, the said three genes are organized in 5' to 3' orientation in a sequential order 1, 2, and 3, with the proviso that the gene encoding scIL-12 is not at position 1, wherein said position 1 is downstream of a promoter, in particular downstream of a promoter for transcription/expression of the said expression cassette (or expression construct).

As described herein, "located upstream" may be more specifically described as "located directly upstream". Furthermore, "located at the 5' end" or "located upstream of the 5' end" may be more specifically described as "located at the 5' end of the transcription initiation site" or "located upstream of the 5' end of the transcription initiation site".

The novel vector of the present disclosure is capable of expressing the genes (or nucleic acid sequences of the genes) encoding 4-1BBL, sc-IL12, and IL-2. Thus, more specifically, the novel vector of the present disclosure is an expression vector, even more specifically a recombinant expression vector.

As described herein, in various embodiments, the term "nucleic acid sequences of genes encoding 4-1BBL, sc-IL12, and IL-2" means "nucleic acid sequences encoding 4-1BBL, sc-IL12, and IL-2", and vice versa. Accordingly, in various embodiments, the term "nucleic acid sequence of a gene encoding 4-1BBL" means "nucleic acid sequence encoding 4-1BBL", and vice versa. Thus, in various embodiments, the term "nucleic acid sequence of a gene encoding scIL-12" means "nucleic acid sequence encoding scIL-12", and vice versa, and "nucleic acid sequence of a gene encoding IL-2" means "nucleic acid sequence encoding IL-2", and vice versa. Likewise, in various embodiments, the term "nucleic acid sequences of genes encoding sc-IL12 and IL-2" means "nucleic acid sequences encoding sc-IL12 and IL-2", and vice versa. As further described herein, in various embodiments, the term "genes encoding 4-1BBL, sc-IL12, and IL-2" means "nucleic acid sequences encoding 4-1BBL, sc-IL12, and IL-2", and vice versa. Accordingly, in various embodiments, the term "gene encoding 4-1BBL" means "nucleic acid sequence encoding 4-1BBL", and vice versa. Likewise, in various embodiments, the term "genes encoding sc-IL12 and IL-2" means "nucleic acid sequences encoding sc-IL12 and IL-2", and vice versa.

The novel vector of the present disclosure provides for a higher expression of 4-1BBL as compared to the expression of scIL-12 and IL-2. Therefore, also provided by the present disclosure is a vector system comprising one or more vectors comprising nucleic acid sequences encoding at least 4-1BB ligand (4-1BBL), single chain IL-12 (scIL-12) and IL-2, wherein the vector system provides for a higher expression of 4-1BBL as compared to the expression of scIL-12 and IL-2. The higher expression of 4-1BBL is regulated by different promoter strength of the promoters regulating transcription of the three transgenes. The said one or more vectors are expression vectors capable of expressing the nucleic acid sequences encoding 4-1BBL, scIL-12 and IL-2. More specifically, the expression vectors are recombinant expression vectors. In various embodiments, the vector system comprising one or more vectors provides for the production of higher or increased levels of 4-1BBL at constant levels of IL-12 and IL-2. In various embodiments, the vector system comprising one or more vectors can be used in a medical setting in order to achieve that at least 5% of cancer cells or immune cells, transduced or transfected with the novel vector/vector system or a virus particle disclosed herein, are expressing 4-1BBL.

In one aspect, the present disclosure provides a vector system comprising one or more vectors comprising nucleic acid sequences encoding at least 4-1BBL, scIL-12 and IL-2, wherein the vector system provides for the production of higher or increased levels of 4-1BBL at constant levels of IL-12 and IL-2. This reflects the finding shown in FIG. 19 that IFN-γ expression is dependent on increasing 4-1BBL levels. Combinations of constant levels of IL-12 and IL-2, both at MOI [5], with increasing levels of 4-1BBL up to MOI [100], lead to increasing IFN-γ induction at moderate IL-12 levels, as shown in FIG. 19. In various embodiments, the vector system of the present disclosure may be used in a medical setting, preferably treatment of cancer, with increased levels of 4-1BBL at constant levels of IL-12 and IL-2. Specifically, the vector system may be used in a medical setting with a vector encoding 4-1BBL at MOI [10] and a vector encoding IL-2 and IL-12 at MOI [5]. Also, the vector system may be used in a medical setting with a vector encoding 4-1BBL at MOI [10] and two vectors each encoding IL-2 and IL-12, respectively, at MOI [5]. In various embodiments, the vector system may be used in a medical setting with a vector encoding 4-1BBL at MOI [25] and one or two vectors encoding IL-2 and IL-12 at MOI [5]. In various other embodiments, the vector system may be used in a medical setting with a vector encoding 4-1BBL at MOI [50] and one or two vectors encoding IL-2 and IL-12 at MOI [5]. In various further embodiments, the vector system may be used in a medical setting with a vector encoding 4-1BBL at MOI [100] and one or two vectors encoding IL-2 and IL-12 at MOI [5]. Preferably, the MOI applied for the vector encoding 4-1BBL achieves that at least 5% of cancer cells or immune cells, transduced or transfected with the novel vector/vector system or a virus particle disclosed herein, are expressing 4-1BBL.

The medical setting referred to above encompasses, without being limited thereto, the treatment of cancer or viral infections. Preferably, the medical setting means the treatment of cancer, more preferably the treatment of solid cancers or solid tumors.

The novel vector system of the present disclosure is capable of expressing the genes (or nucleic acid sequences of the genes) encoding 4-1BBL, sc-IL12, and IL-2. Thus, more specifically, the novel vector system of the present disclosure is an expression vector system comprising one or more expression vectors, even more specifically a recombinant expression vector system comprising one or more recombinant expression vectors. In various preferred embodiments, the vector type of the one or more vectors comprising the nucleic acid sequences encoding at least 4-1BBL, scIL-12 and IL-2 is the same for all vectors of the vector system. The vector typically is of a type that is capable of carrying the nucleic acid sequences encoding at least 4-1BBL, scIL-12 and IL-2. Thus, the vector is of a type having the capacity of taking up the nucleic acid sequences encoding at least 4-1BBL, scIL-12 and IL-2. Preferably, each of the one or more vectors comprising the nucleic acid sequences encoding at least 4-1BBL, scIL-12 and IL-2 is any one of an adenoviral vector, a retroviral vector, a lentiviral vector, a poxvirus vector, a vaccinia virus vector, preferably MVA, an adenovirus vector, an adenovirus-associated virus vector, a herpes virus vector, an alpha virus vector, and a measles virus vector. More preferably, each of the one or more vectors comprising the nucleic acid sequences encoding at least 4-1BBL, scIL-12 and IL-2 is an adenoviral vector, a retroviral vector, a poxvirus vector, a vaccinia virus vector, preferably MVA, an adenovirus vector, an adenovirus-associated virus vector, or a herpes virus vector. Still more preferably, each of the one or more vectors comprising the nucleic acid sequences encoding at least 4-1BBL, scIL-12 and IL-2 is an adenoviral vector, a herpes virus vector, or a vaccinia virus vector, preferably MVA.

The present disclosure demonstrates a relationship between IFN-γ expression and increasing 4-1BBL levels in the context of the immunostimulating vector system that is based on one or more vectors comprising nucleic acid sequences encoding at least 4-1BBL, scIL-12 and IL-2. As described in Example 11 and shown in FIG. 19, transgene expression of 4-1BBL, IL-2 and scIL-12 and IFN-γ response of Im02, and combinations of single-gene expressing vectors reveal that IFN-γ expression is dependent on increasing 4-1BBL levels. Combinations of constant levels of IL-12 and IL-2, both at MOI [5], with increasing levels of 4-1BBL up to MOI [100], lead to increasing IFN-γ induction at moderate IL-12 levels, as shown in FIG. 19. The important finding of the present disclosure is that maximum induction of IFN-γ and the related immune activation can be achieved not only by the specific arrangement of the nucleic acid sequences encoding 4-1BBL, scIL-12 and IL-2 as depicted in vector Im02, but also by alternative embodiments that provide for an increased or higher expression of 4-1BBL as compared to the expression of scIL-12 and IL-2. Thus, the present disclosure provides a vector comprising nucleic acid sequences encoding 4-1BBL, scIL-12 and IL-2, wherein the vector provides for the production of higher or increased levels of 4-1BBL at constant levels of IL-12 and IL-2. More specifically, the present disclosure also provides a vector comprising nucleic acid sequences encoding 4-1BBL, scIL-12 and IL-2, and further comprising at least one regulatory nucleic acid sequence providing for an increased or higher expression level of 4-1BBL as compared to the expression levels of scIL-12 and IL-2. This aspect reflects the finding that vector Im02 has been shown to provide for a higher expression of 4-1BBL as compared to the expression of scIL-12 and IL-2, and that combinations of constant levels of IL-12 and IL-2, both at MOI [5], with increasing levels of 4-1BBL up to MOI [100], lead to increasing IFN-γ induction at moderate IL-12 levels, as discussed above.

FIGS. 3 and 19 show that the expression level of 4-1BBL obtained with a vector or vector system of the present disclosure is increased as compared to the expression level of 4-1BBL obtained by the expression construct of vector Im01. Therefore, in a preferred embodiment, the expression level of 4-1BBL is increased as compared to the expression level of 4-1BBL obtained by the expression construct of vector Im01.

FIGS. 3 and 19 also show that the expression level of scIL-12 is decreased as compared to the expression level of scIL-12 obtained by the expression construct of vector Im01. Therefore, in a preferred embodiment, the expression level of scIL-12 is decreased as compared to the expression level of scIL-12 obtained by the expression construct of vector Im01.

FIGS. 3 and 19 further show that the expression level of IL-2 is increased as compared to the expression level of IL-2 obtained by the expression construct of vector Im01. Therefore, in a preferred embodiment, the expression level of IL-2 is increased as compared to the expression level of IL-2 obtained by the expression construct of vector Im01.

The present disclosure encompasses a vector comprising nucleic acid sequences encoding 4-1BBL, scIL-12 and IL-2, and further comprising at least one regulatory nucleic acid sequence providing for an increased or higher expression level of 4-1BBL as compared to the expression level of 4-1BBL obtained by the expression construct of vector Im01. Preferably, the expression level of scIL-12 is decreased as compared to the expression level of scIL-12 obtained by the expression construct of vector Im01 and/or the expression level of IL-2 is increased as compared to the expression level of IL-2 obtained by the expression construct of vector Im01. More specifically, the at least one regulatory nucleic acid sequence provides for a decreased expression level of scIL-12 as compared to the expression level of scIL-12 obtained by the expression construct of vector Im01 and/or the at least one regulatory nucleic acid sequence provides for an increased expression level of IL-2 as compared to the expression level of IL-2 obtained by the expression construct of vector Im01.

The expression construct of vector Im01 is depicted in Example 1, and comprises a CMV promoter, two IRES elements, scIL-12, 4-1BBL, IL-2 and a poly-A signal organized in 5' to 3' orientation in the following sequential order: 5'-CMV-scIL-12-IRES-4-1BBL-IRES-IL-2-poly-A signal-3'.

More specifically, the expression construct of vector Im01 corresponds to the expression construct of the vector designated "Ad-3" shown in FIG. 1 of WO 2004/035799 A2. The expression construct of vector "Ad-3" is hereby incorporated into the present disclosure by reference. In FIG. 1 of WO 2004/035799 A2, the designation "Ad-3" means the complete vector carrying the corresponding expression construct or cassette shown in said FIG. 1. Accordingly, expression construct of vector "Ad-3" means the expression construct depicted in the bottom line of FIG. 1 of WO 2004/035799 A2. In the present disclosure, the expression construct of vector Im01 preferably corresponds to the expression construct of vector "Ad-3" as shown in FIG. 1 of WO 2004/035799 A2 and comprising human cDNA of the nucleic acid sequences encoding scIL-12, 4-1BBL, and IL-2. Accordingly, the expression construct of vector Im01 as referred to in the present disclosure comprises the following elements organized in 5' to 3' orientation in the following sequential order: 5'-CMV-human scIL-12-PV-IRES-human 4-1BBL-EMCV-IRES-human IL-2-SV-40 poly-A-3'.

In various embodiments of the present disclosure, reference to "expression levels obtained by the expression construct of vector Im01" means "expression levels obtained by the vector Im01". Vector Im01 is an adenoviral vector. Thus, in various embodiments of the present disclosure, reference to "expression levels obtained by the vector Im01" includes an adenoviral vector comprising the expression construct of vector "Ad-3" as shown in FIG. 1 of WO 2004/035799 A2 with human cDNA of the nucleic acid sequences encoding scIL-12, 4-1BBL, and IL-2. More specifically, reference to "expression levels obtained by the vector Im01" means expression levels obtained by an adenoviral vector comprising the following elements organized in 5' to 3' orientation in the following sequential order: 5'-CMV-human scIL-12-PV-IRES-human 4-1BBL-EMCV-IRES-human IL-2-SV-40 poly-A-3'. Thus, in preferred embodiments, reference to "expression levels obtained by the expression construct of vector Im01" means "expression levels obtained by the expression construct of vector Im01" as shown in FIG. 20. Accordingly, with reference to FIG. 20, vector Im01 means the shuttle vector hu pE1.1 Im01. The expression construct of vector Im01 shown in FIG. 20 encompasses the CMV promoter, human scIL-12, PV IRES, human 4-1BBL, EMCV IRES, human IL-2, and SV40polyA. The nucleotide sequence of the shuttle vector hu pE1.1 Im01 depicted in FIG. 20 has a total of 7,845 bp. The nucleotide sequences of the CMV promoter, human scIL-12, PV IRES, human 4-1BBL, EMCV IRES, human IL-2, and SV40polyA can be identified in the nucleotide sequence of SEQ ID NO: 11 (FIG. 17), which shows the nucleotide sequence of the shuttle vector hu pE1.1 Im02 depicted in FIG. 2. The nucleotide sequences of the CMV promoter, human scIL-12, PV IRES, human 4-1BBL, EMCV IRES, human IL-2, and SV40polyA of the shuttle vector hu pE1.1 Im01 correspond to the respective nucleotide sequences of the CMV promoter, human 4-1BBL, EMCV IRES, human IL-2, PV IRES, human scIL-12, and SV40polyA of the shuttle vector hu pE1.1 Im02.

In various preferred embodiments, reference to "expression levels obtained by the expression construct of vector Im01" means expression levels obtained by the expression construct of vector Im01 cloned or sub-cloned into a plasmid or vector carrying, e.g., adenoviral vector DNA. More preferably, reference to "expression levels obtained by the expression construct of vector Im01" means expression levels obtained by the expression construct of vector Im01 cloned or sub-cloned into an adenoviral vector.

In various embodiments, the vector type is the same for the vector comprising the nucleic acid sequences encoding 4-1BBL, scIL-12 and IL-2, and the vector comprising the expression construct of vector Im01. The vector typically is of a type that is capable of carrying the nucleic acid sequences encoding 4-1BBL, scIL-12 and IL-2. Thus, the vector is of a type having the capacity of taking up the nucleic acid sequences encoding 4-1BBL, scIL-12 and IL-2. Preferably, each of the one or more vectors comprising the nucleic acid sequences encoding 4-1BBL, scIL-12 and IL-2 is any one of an adenoviral vector, a retroviral vector, a lentiviral vector, a poxvirus vector, a vaccinia virus vector, preferably MVA, an adenovirus vector, an adenovirus-associated virus vector, a herpes virus vector, an alpha virus vector, and a measles virus vector. More preferably, each of the one or more vectors comprising the nucleic acid sequences encoding 4-1BBL, scIL-12 and IL-2 is an adenoviral vector, a retroviral vector, a poxvirus vector, a vaccinia virus vector, preferably MVA, an adenovirus vector, an adenovirus-associated virus vector, or a herpes virus vector. Still more preferably, each of the one or more vectors comprising the nucleic acid sequences encoding 4-1BBL, scIL-12 and IL-2 is an adenoviral vector, a herpes virus vector, or a vaccinia virus vector, preferably MVA.

In various embodiments of the present disclosure, reference to "expression levels obtained by the expression construct of vector Im01" or "expression levels obtained by the vector Im01" means expression levels obtained by application of a standard in vitro expression system comprising a tumor cell line, preferably human A549 cells, to be transduced with the vector (i.e., a vector or vector system of the present disclosure, or vector Im01 or a vector, preferably an adenoviral vector, comprising the expression construct of vector Im01), and a subsequent overlay of human blood immune cells as target cells.

Thus, the disclosure provides a vector comprising nucleic acid sequences encoding 4-1BBL, scIL-12 and IL-2, and further comprising at least one regulatory nucleic acid sequence providing for an increased expression level of 4-1BBL as compared to the expression levels of scIL-12 and IL-2, wherein the expression levels are determined in an in vitro expression system (or expression assay) comprising a tumor cell line, preferably a human A549 cell line, transduced with a vector, preferably an adenoviral vector, comprising the expression construct of vector Im01, and human blood immune cells, preferably peripheral blood mononuclear cells (PBMCs).

In the present disclosure, the terms expression level or transgene expression level and expression rate or transgene expression rate may be used interchangeably.

The expression levels of 4-1BBL, IL-2 and scIL-12 provided by the vector or vector system of the present disclosure induce an immune response that is transgene-specific, i.e., is specific for the expression levels of 4-1BBL, IL-2 and scIL-12 provided by the vector or vector system of the present disclosure. The expression levels provided by the vector or vector system of the present disclosure induces an immune response that is particularly specific for the increased expression level of 4-1BBL as compared to the expression levels of scIL-12 and IL-2. Preferably, the expression levels of 4-1BBL, IL-2 and scIL-12 provided by the vector or vector system of the present disclosure induce an immune response that is particularly specific for the increased expression level of 4-1BBL as compared to the expression levels of scIL-12 and IL-2, wherein the expression level of 4-1BBL is increased as compared to the expression level of 4-1BBL obtained by the expression construct of vector Im01. More preferably, the expression levels of 4-1BBL, IL-2 and scIL-12 provided by the vector or vector system of the present disclosure induce an immune response that is particularly specific for the increased expression level of 4-1BBL as compared to the expression levels of scIL-12 and IL-2, wherein the expression level of scIL-12 is decreased and/or the expression level of IL-2 is increased as compared to the expression levels of scIL-12 and/or IL-2 obtained by the expression construct of vector Im01. Still more preferably, the expression levels of 4-1BBL, IL-2 and scIL-12 provided by the vector or vector systems of the present disclosure induce an immune response that is particularly specific for the increased expression level of 4-1BBL as compared to the expression levels of scIL-12 and IL-2, wherein the expression level of 4-1BBL is increased as compared to the expression level of 4-1BBL obtained by the expression construct of vector Im01, and wherein the expression level of scIL-12 is decreased and/or the expression level of IL-2 is increased as compared to the expression levels of scIL-12 and/or IL-2 obtained by the expression construct of vector Im01.

The transgene-specific immune response preferably means transgene-specific IFN-γ response or transgene-specific expression or production of IFN-γ. Cytokine levels including IFN-γ levels can routinely be assayed by ELISA.

In preferred embodiments, the transgene-specific immune response induced by the expression levels of 4-1BBL, IL-2 and scIL-12 is detected or determined by an in vitro assay, preferably ELISA.

In various embodiments of the present disclosure, the nucleic acid sequences encoding 4-1BBL, IL-2 and scIL-12 are expressed by one vector from two individual regulatory nucleic acid sequences, wherein one regulatory nucleic acid sequence is located upstream of the nucleic acid sequence encoding 4-1BBL, and the other regulatory nucleic acid sequence is located upstream of an expression cassette comprising nucleic acid sequences encoding IL-2 and scIL-12. Preferably, the said expression cassette comprises nucleic acid sequences encoding IL-2 and scIL-12 in 5' to 3' orientation in the order 5'-IL-2-scIL-12-3'. According to the present disclosure, the two regulatory nucleic acid sequences provide for an increased or higher expression level of 4-1BBL as compared to the expression levels of scIL-12 and IL-2 and/or provide for an increased or higher expression level of 4-1BBL as compared to the expression level of 4-1BBL obtained by the expression construct of vector Im01. Preferably, the two regulatory nucleic acid sequences also or further provide for a decreased expression level of scIL-12 as compared to the expression level of scIL-12 obtained by the expression construct of vector Im01 and/or an increased expression level of IL-2 as compared to the expression level of IL-2 obtained by the expression construct of vector Im01. Preferably, the regulatory nucleic acid sequences are promoter sequences.

In various embodiments of the present disclosure, the nucleic acid sequences encoding 4-1BBL, IL-2 and scIL-12 are expressed by one vector from three individual regulatory nucleic acid sequences, wherein one regulatory nucleic acid sequence is located upstream of the nucleic acid sequence encoding 4-1BBL, one regulatory nucleic acid sequence is located upstream of the nucleic acid sequence encoding IL-2, and one regulatory nucleic acid sequence is located upstream of the nucleic acid sequence encoding scIL-12. According to the present disclosure, the three regulatory nucleic acid sequences provide for an increased or higher expression level of 4-1BBL as compared to the expression levels of scIL-12 and IL-2 and/or provide for an increased or higher expression level of 4-1BBL as compared to the expression level of 4-1BBL obtained by the expression construct of vector Im01. Preferably, the three regulatory nucleic acid sequences also or further provide for a decreased expression level of scIL-12 as compared to the expression level of scIL-12 obtained by the expression construct of vector Im01 and/or an increased expression level of IL-2 as compared to the expression level of IL-2 obtained by the expression construct of vector Im01. Preferably, the regulatory nucleic acid sequences are promoter sequences.

As described herein, regulatory nucleic acid sequence(s) preferably means promoter(s) (sequence(s)) or, more specifically, expression promoter(s) sequence(s)). Strong promoters that may be used for the intended increased or high expression of level of 4-1BBL include, without being limited thereto, any one of: Cytomegalovirus (CMV), Elongation Factor 1 Alpha (EF1A), Rous Sarcoma Virus (RSV), Simian Virus 40 (SV40). CMV is a particularly preferred promoter. These promoters can be used in various embodiments of the present disclosure, and represent preferred promoters that can provide for an increased expression level of 4-1BBL as compared to the expression levels of scIL-12 and IL-2. This applies in particular for embodiments, in which the three nucleic acid sequences encoding 4-1BBL, IL-2 and scIL-12 are organized in a tricistronic cassette in 5' to 3' orientation in a sequential order 1, 2, 3 with the nucleic acid sequence encoding 4-1BBL located upstream of the nucleic acid sequences encoding IL-2 and scIL-12, preferably wherein the three nucleic acid sequences encoding 4-1BBL, IL-2 and scIL-12 are organized from 5' to 3' in the following order: 5'-4-1BBL-IL-2-scIL-12-3'.

Promoters that may be used for the intended expression of IL-2 and/or IL-12 include, without being limited thereto, Phosphoglycerate Kinase (PGK) and Ubiquitin C (UBC). These promoters can be used in various embodiments of the present disclosure, and represent preferred promoters that can provide for the intended expression level of IL-2 and IL-12. In particular, these promoters can be used in embodiments, in which the nucleic acid sequences encoding 4-1BBL, IL-2 and scIL-12 are expressed by one vector from two individual regulatory nucleic acid sequences, wherein one regulatory nucleic acid sequence is located upstream of the nucleic acid sequence encoding 4-1BBL, and the other regulatory nucleic acid sequence is located upstream of an expression cassette comprising the nucleic acid sequences encoding IL-2 and scIL-12. These promoters can furthermore be used in embodiments, in which the nucleic acid sequences encoding 4-1BBL, IL-2 and scIL-12 are expressed by one vector from three individual regulatory nucleic acid sequences, wherein one regulatory nucleic acid sequence is located upstream of the nucleic acid sequence encoding 4-1BBL, one regulatory nucleic acid sequence is located upstream of the nucleic acid sequence encoding IL-2, and one regulatory nucleic acid sequence is located upstream of the nucleic acid sequence encoding scIL-12.

In various embodiments, the at least one regulatory nucleic acid sequence of the vector comprising nucleic acid sequences encoding 4-1BBL, scIL-12 and IL-2, provides for the same expression level or expression ratio of 4-1BBL, scIL-12 and IL-2 that is obtained with the vector Im02.

The one or more vectors of the novel vector/vector system of the present disclosure may be any one of an adenoviral vector, an adeno-associated virus vector, a lentiviral vector, a retroviral vector, a herpes simplex virus vector, a pox virus vector, a RNA vector, a plasmid vector, a nanoparticle vector, and naked DNA, or a combination thereof.

In various embodiments of the disclosure, the one or more vectors of the novel vector/vector system are viral vectors. Viral vectors may be live, attenuated, replication-conditional or replication-deficient, and may also be a non-pathogenic (defective), replication-competent viral vector.

In certain embodiments of the present disclosure, the one or more vectors of the novel vector/vector system of the present disclosure are selected from retroviral vector genome, lentiviral vector genome, poxvirus vector genome, vaccinia virus vector genome, adenovirus vector genome, adenovirus-associated virus vector genome, herpes virus vector genome, alpha virus vector genome, plasmid DNA and RNA.

Safety features of the viral vector, e.g., integration deficiency, are desirably incorporated. In certain embodiments integration deficiency may be conferred by elements of the vector genome but may also derive from elements of the packaging system (e.g., a non functional integrase protein that may not be part of the vector genome but supplied in trans).

In various embodiments, the one or more vectors of the novel vector/vector system of the disclosure are replicative vectors. Preferably, the replicative vectors are replicating viral vectors, more preferably replicating adenoviral vectors. In various other embodiments, the one or more vectors of the novel vector/vector system of the present disclosure are non-replicative vectors, preferably non-replication competent viral vectors, more preferably non-replication competent adenoviral vectors.

If the one or more vectors of the novel vector/vector system of the disclosure are RNA vectors, these may comprise inserted modified ribonucleotides.

Exemplary viral vectors of the present disclosure include, but are not limited to, retroviral vectors, lentiviral vectors, poxvirus vectors, vaccinia virus vectors, adenovirus vectors, adenovirus-associated virus vectors, herpes virus vectors, and alpha virus vectors. Preferably, the viral vector is an adenoviral vector.

In certain embodiments, an adenovirus vector or adenovirus-associated virus vector may be used for expressing the three genes 4-1BB ligand (4-1BBL), single chain IL-12 (scIL-12) and IL-2. Several adenovirus vector systems and methods for administering the vectors have been described (see, e.g., Mercier et al., *Proc. Natl. Acad. Sci. USA*, 2004, 101:6188-93).

Retroviral vectors may include those based upon murine leukemia virus (MuLV), gibbon ape leukemia virus (GaLV), ecotropic retroviruses, simian immunodeficiency virus (SIV), human immunodeficiency virus (HIV), and combinations thereof.

In certain embodiments, the one or more vectors of the novel vector/vector system of the disclosure is a retroviral vector, preferably a lentiviral vector. Suitable genome-based lentiviral vectors for human gene therapy include those based on Human Immunodeficiency Virus (HIV-1), HIV-2, feline immunodeficiency virus (FIV), equine infectious anemia virus, Vesicular Stomatitis Virus (VSV), and Simian Immunodeficiency Virus (SIV).

In various embodiments, the vector is plasmid DNA or cosmid DNA. Plasmid DNA or cosmid DNA containing one or more polynucleotides encoding at least 4-1BBL, scIL-12 and IL-2 as described herein are readily constructed using standard techniques well known in the art. The vector may be typically constructed in a plasmid form that can then be transfected into a packaging or producer cell line. The plasmid generally comprises sequences useful for replication of the plasmid in bacteria. Such plasmids are well known in the art. In addition, vectors that include a prokaryotic origin of replication may also include a gene whose expression confers a detectable or selectable marker such as a drug resistance.

In one embodiment, recombinant expression vectors are provided comprising a polynucleotide sequence encoding at least 4-1BBL, scIL-12 and IL-2 that induce an immune response in an infectious disease or cancer setting. For directing expression of 4-1BBL, scIL-12 and IL-2, the encoding polynucleotide sequences in each vector should include at least one appropriate expression control sequence (also called a regulatory expression sequence or feature) that is operatively linked to the encoding polynucleotide sequence(s). Expression control elements that may be used for regulating the expression of the encoded polypeptides are known in the art and include, but are not limited to, inducible promoters, constitutive promoters, secretion signals, enhancers, leaders and other regulatory sequences.

As described herein, the expression vector may comprise at least one regulatory expression sequence (expression control sequence). In certain embodiments, when the expression vector comprises a viral vector genome, expression of 4-1BBL, scIL-12 and IL-2 is desired in particular target cells. Typically, for example, in a viral vector the polynucleotide sequence encoding 4-1BBL, scIL-12 and/or IL-2 is located between the 5' LTR and 3' LTR sequences. Furthermore, the encoding nucleotide sequence(s) is preferably operatively linked in a functional relationship with other genetic or regulatory sequences or features, for example transcription regulatory sequences including promoters or enhancers, that regulate expression of the genes encoding 4-1BBL, scIL-12 and IL-2 in a particular manner. With respect to viral vector constructs, an "internal" promoter/enhancer is one that is located between the 5' LTR and the 3' LTR sequences in the viral vector and is operatively linked to the encoding polynucleotide sequence of interest. The internal promoter/enhancer may be any promoter, enhancer or promoter/enhancer combination known to increase expression of a gene with which it is in a functional relationship. A "functional relationship" and "operatively linked" mean, without limitation, that the sequence is in the correct location and orientation with respect to the promoter and/or enhancer such that the sequence of interest will be expressed when the promoter and/or enhancer is contacted with the appropriate molecules. In certain instances, the useful transcriptional regulatory sequences are those that are highly regulated with respect to activity, both temporally and spatially. The choice of an internal promoter/enhancer is based on the desired expression pattern of the three genes 4-1BBL, scIL-12 and IL-2 and the specific properties of known promoters/enhancers. Thus, the internal promoter may be constitutively active. Non-limiting examples of constitutive promoters that may be used include the CMV promoter. In various embodiments of the disclosure, the novel vector/vector system comprises an internal promoter/enhancer, which provides for a higher expression of 4-1BBL as compared to scIL-12 and IL-2. Many enhancers in viral genomes and in mammalian genomes have been identified and characterized (see, e.g., publically available databases such as GenBank). Enhancers are typically cis-acting elements of DNA, usually about 10 to 300 bp in length, that act on a promoter to increase its transcription. Many enhancer sequences are now known from mammalian genes and from eukaryotic cell viruses. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the polynucleotide sequence encoding the gene(s) of interest, but is preferably located at a site 5' from the promoter. An enhancer can be used in combination with a heterologous promoter. One of ordinary skill in the art will be able to select the appropriate enhancer based on the desired expression pattern of 4-1BBL, scIL-12 and IL-2.

In various embodiments, the promoter may be a tissue specific promoter. In some embodiments, the promoter is a target cell-specific promoter. In addition, promoters may be selected to allow for inducible expression of 4-1BBL, scIL-12 and/or IL-2. A number of systems for inducible expression are known in the art, including the tetracycline responsive system, the lac operator-repressor system, as well as promoters responsive to a variety of environmental or physiological changes, including heat shock, metal ions, interferons, hypoxia, steroids, and radiation. A combination of promoters may also be used to obtain the desired expression of each of the three genes encoding 4-1BBL, scIL-12 and IL-2. The artisan of ordinary skill will be able to select a promoter based on the desired expression pattern of the polynucleotide sequence(s) in the organism or the target tissue or target cell of interest.

As described herein, the expression vector, including a viral vector genome, may comprise at least one RNA Polymerase II or III responsive promoter. This promoter can be operatively linked to the polynucleotide sequence(s) encoding at least 4-1BBL, scIL-12 and/or IL-2 and can also be linked to a termination sequence. In addition, more than one RNA Polymerase II or III promoter may be incorporated. RNA polymerase II and III promoters are well known to the person of skill in the art.

When targeting delivery of a recombinant expression vector, including a viral vector genome, to a particular target cell or target tissue for inducing a cell-mediated immune response, the vector genome will usually contain a promoter that is recognized by the target cell or target tissue and that is operatively linked to the sequence(s) of interest, viral components (when the vector is a viral vector), and other sequences discussed herein.

Promoters may be inducible, constitutive, temporally active or tissue specific. Inducible promoters are useful tools in genetic engineering because the expression of genes to which they are operatively linked can be turned on or off, e.g., in a particular tissue. Inducible promoters can be grouped as chemically-regulated promoters, and physically-regulated promoters. Typical chemically-regulated promoters include, not are not limited to, steroid-regulated promoter (e.g., rat glucocorticoid receptor (GR)-based promoter, human estrogen receptor (ER)-based promoter), metal-regulated promoters (e.g., metallothionein gene-based promoters), and pathogenesis-related promoters (e.g., Arabidopsis and maize pathogen-related (PR) protein-based promoters). Typical physically-regulated promoters include, but are not limited to, temperature-regulated promoters (e.g., heat shock promoters), and light-regulated promoters (e.g., soybean SSU promoter). Other exemplary promoters are well known to the person skilled in the art.

In various embodiments, the human cytomegalovirus (CMV) immediate early gene promoter, the SV40 early promoter and the Rous sarcoma virus long terminal repeat can be used. The use of other viral or mammalian cellular or bacterial phage promoters, which are well-known in the art to achieve expression of polynucleotides, is contemplated as well. The one of skill in the art will be able to select an appropriate promoter based on the specific circumstances. Many different promoters are described in the art, as are methods for operatively linking the promoter to the polynucleotide sequence to be expressed. Both native promoter sequences and many heterologous promoters may be used to direct expression in a packaging cell and a target cell or target tissue. Heterologous promoters are typically used because they generally permit greater transcription and higher yields of the desired protein as compared to the native promoter. The promoter may be obtained, for example, from the genomes of viruses such as polyoma virus, fowlpox virus, adenovirus, bovine papilloma virus, avian sarcoma virus, cytomegalovirus, a retrovirus, hepatitis-B virus and Simian Virus 40 (SV40). The promoter may also be, for example, a heterologous mammalian promoter, for example, the actin promoter or an immunoglobulin promoter, a heat-shock promoter, or the promoter normally associated with the native sequence, provided such promoters are compatible with the target cell or target tissue. In one embodiment, the promoter is the naturally occurring viral promoter in a viral expression system. In some embodiments, the promoter is a tumor cell-specific promoter. Expression vectors may also contain sequences necessary for the termination of transcription and for stabilizing the mRNA. These sequences are often found in the 5' and, occasionally 3', untranslated regions of eukaryotic or viral DNAs or cDNAs and are well known in the art.

The novel vector/vector system of the disclosure may further encode one or more immunogens, which include, but are not limited to, immunogens from an oncogenic virus (e.g., EBV, HPV, HBV, HCV, HTLV, and KSHV) and tumor-associated antigens. Preferably, the tumor associated antigen is a tumor-associated antigen from bladder cancer, liver cancer, Merkel cell carcinoma, renal cell carcinoma, prostate cancer, mesothelioma, pancreatic cancer, melanoma, breast cancer, colorectal cancer, lung cancer, ovarian cancer. More preferably, the tumor-associated antigen is from bladder cancer. In certain embodiments, the tumor associated antigen is any one of p53, Ras, c-Myc, A-Raf, B-Raf, C-Raf, NY-ESO-1, LAGE-1, MAGE-A1, MAGE-A2, MAGE-A3, MAGE-A4, MAGE-A6, MAGE-A10, MAGE-A12, CT7, CT10, GAGE, IMP3, BK T-antigen, MART-1, DAM-6, NA88-A, Gp100, PSA, PSM, Tyrosinase, TRP-1, TRP-2, ART-4, CAMEL, CEA, Cyp-B, hTERT, hTRT, MUC1, MUC2, TRK receptors, PRAME, P15, SART-1, SART-2, SART-3, Wilms' tumor antigen (WT1), AFP, CEA, ELF2M, GnT-V, G250, HSP70-2M, HST-2, MUM-1, MUM-2, MUM-3, RAGE, 707-AP, BCR-ABL, interferon regulatory factor 4 (IRF4), Tumor-associated calcium signal transducer 1 (TACSTD1) TACSTD2, receptor tyrosine kinases, Epidermal Growth Factor Receptor (EGFR), platelet derived growth factor receptor (PDGFR), vascular endothelial growth factor receptor (VEGFR), cytoplasmic tyrosine kinases, src-family, Nuclear Factor-Kappa B (NF-κB), Notch receptors, c-Met, extracellular signal-regulated kinases (ERKs), PMSA, PR-3, MDM2, Mesothelin, renal cell carcinoma-5T4, SM22-alpha, STEAD, hTERT, sarcoma translocation breakpoints, EpCAM, NA17, PAX3, ALK, androgen receptor, cyclin B1, MYCN, BORIS, sperm protein 17, SSX2, B7H3, TIE2, Page4, MAD-CT-1, FAP, MAD-CT-2, and fos related antigen 1. In another embodiment, a method is provided herein wherein the tumor-associated antigen is selected from a bladder cancer antigen. In one embodiment, the bladder cancer antigen is any one of CTA, NY-ESO-1, LAGE-1, MAGE-A1, MAGE-A3, MAGE-A4, MAGE-A10, CT7, CT10, GAGE, PRAME; BAGE; RAGE, SAGE, HAGE, MPHOSPH1, DEPDCI, IMP3 and MAGE-A, and BK T-antigen.

When the expression vector is a viral vector genome, the viral vector genome may be typically constructed in a plasmid form that may be transfected into a packaging or producer cell line for production of the viral vector genome construct. The plasmid generally comprises sequences useful for replication of the plasmid in bacteria. Such plasmids are well known in the art. In addition, vectors that include a prokaryotic origin of replication may also include a gene whose expression confers a detectable or selectable marker such as a drug resistance. As will be understood by those of skill in the art, it can be advantageous to modify a coding sequence to enhance its expression in a particular host. The genetic code is redundant with 64 possible codons, but most organisms preferentially use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias". Optimized coding sequences containing codons preferred by a particular prokaryotic or eukaryotic host can be prepared, for example, to increase the rate of translation or to produce recombinant RNA transcripts having desirable properties, such as a longer half-life, as compared with transcripts produced from a non-optimized sequence. In various embodiments, the nucleic acid sequence(s) encoding at least 4-1BBL, scIL-12, and/or IL-2 is codon-optimized for expression in human. In preferred embodiments of the present disclosure, the nucleic acid sequence encoding 4-1BBL is human cDNA (human gene of 4-1BBL), the nucleic acid sequence encoding scIL-12 is human cDNA (human gene of scIL-12), and/or the nucleic acid sequence encoding IL-2 is human cDNA (human gene of IL-2).

In various embodiments, the nucleic acid sequence(s) of the novel vector/vector system of the present disclosure are cDNA sequences. The nucleic acid sequences of the genes of 4-1BBL, scIL-12, and/or IL-2 contained in the novel vector/vector system of the present disclosure may be considered as heterologous nucleic acid sequences. The terms nucleic acid sequence(s) and polynucleotide(s) may be used interchangeably herein. As described herein, the term "nucleic acid sequence" may encompass both single-stranded and double-stranded nucleic acid sequences. In various embodiments, a nucleic acid sequence is DNA sequence.

In various embodiments, the vector is a DNA vector. In various embodiments, the vector is an RNA vector. The novel vector of the present disclosure may be more specifically described as a circular vector, even more specifically as a circular expression vector. As described herein, the term "vector" may encompass both single-stranded and double-stranded vectors, including, but not limited to, single-stranded and double-stranded DNA vectors.

As described herein, nucleic acid sequences of genes encoding 4-1BBL encompass nucleic acid sequences encoding variants of 4-1BBL, in particular variants of 4-1BBL having the amino acid sequence as shown in SEQ ID NO: 2 (FIG. 13). Such variant sequences are described in further detail herein below. Likewise, nucleic acid sequences of genes encoding IL-2 encompass nucleic acid sequences encoding variants of IL-2, in particular variants of IL-2 having the amino acid sequence as shown in SEQ ID NO: 4 (FIG. 14). Such variant sequences are described in further detail herein below. Also, nucleic acid sequences of genes encoding scIL-12 encompass nucleic acid sequences encoding variants of scIL-12, in particular variants of scIL-12 having the amino acid sequence as shown in SEQ ID NO: 6 (FIG. 15). Such variant sequences are described in further detail herein below.

In various embodiments of the disclosure, the nucleic acid sequence (of the gene) encoding 4-1BBL comprises (i) the nucleic acid sequence of SEQ ID NO: 1, wherein the nucleic acid sequence is codon-optimized for expression in human, (ii) the nucleic acid sequence (of the gene) encoding IL-2 comprises the nucleic acid sequence of SEQ ID NO: 3, wherein the nucleic acid sequence is codon-optimized for expression in human, and/or (iii) the nucleic acid sequence (of the gene) encoding scIL-12 comprises the nucleic acid sequence of SEQ ID NO: 5, wherein the nucleic acid sequence is codon-optimized for expression in human. 4-1BB is a member of the Tumor Necrosis Factor (TNF) receptor family. CD137 is the designation for 4-1BB according to the CD nomenclature. In the present disclosure, the terms CD137 and 4-1BB can be used interchangeably. Accordingly, the terms 4-1BB ligand (4-1BBL) and CD137 ligand can also be used interchangeably in the present disclosure. In various embodiments of the disclosure, the nucleic acid sequence encoding 4-1BBL (or CD137 ligand) shows at least 70% homology or sequence identity to the nucleic acid sequence of SEQ ID NO: 1 (FIG. 13), wherein the variant nucleic acid sequence encodes a 4-1BBL protein capable of specifically binding activated T cells, preferably CD4+ helper cells and CD8+ T cells. Preferably, the nucleic acid sequence encoding 4-1BBL shows at least 80% homology or sequence identity to the nucleic acid sequence of SEQ ID NO: 1 (FIG. 13), wherein the variant nucleic acid sequence encodes a 4-1BBL protein capable of specifically binding activated T cells, preferably CD4+ helper cells and CD8+ T cells. More preferably, the nucleic acid sequence encoding 4-1BBL shows at least 90% homology or sequence identity to the nucleic acid sequence of SEQ ID NO: 1 (FIG. 13), wherein the variant nucleic acid sequence encodes a 4-1BBL protein capable of specifically binding activated T cells, preferably CD4+ helper cells and CD8+ T cells. Even more preferably, the nucleic acid sequence encoding 4-1BBL shows at least 95%, 96%, 97%, 98%, or 99% homology or sequence identity to the nucleic acid sequence of SEQ ID NO: 1 (FIG. 13), wherein the variant nucleic acid sequence encodes a 4-1BBL protein capable of specifically binding activated T cells, preferably CD4+ helper cells and CD8+ T cells. In certain embodiments, variants of 4-1BBL as described above exhibit the same binding specificity for T cells, preferably CD4+ helper cells and CD8+ T cells, as the native 4-1BBL encoded by the sequence of SEQ ID NO: 1 (FIG. 13). In a particularly preferred embodiment, the nucleic acid sequence encoding 4-1BBL comprises (or consists of) the sequence of SEQ ID NO: 1 (FIG. 13). In various preferred embodiments, a variant sequence of the nucleic acid sequence of human 4-1BBL as described herein is not a nucleotide sequence encoding mouse 4-1BBL. Thus, in various preferred embodiments the novel vector/vector system of the present disclosure does not comprise a nucleic acid sequence encoding 4-1BBL of mouse origin.

In various embodiments of the disclosure the nucleic acid sequence encoding IL-2 shows at least 70% homology or sequence identity to the nucleic acid sequence of SEQ ID NO: 3 (FIG. 14), wherein the variant nucleic acid sequence encodes an IL-2 protein having immune stimulating activity, preferably T helper cell and CD8+ T cell stimulating activity. Preferably, the nucleic acid sequence encoding IL-2 shows at least 80% homology or sequence identity to the nucleic acid sequence of SEQ ID NO: 3 (FIG. 14), wherein the variant nucleic acid sequence encodes an IL-2 protein having immune stimulating activity, preferably T helper cell and CD8+ T cell stimulating activity. More preferably, the nucleic acid sequence encoding IL-2 shows at least 90% homology or sequence identity to the nucleic acid sequence of SEQ ID NO: 3 (FIG. 14), wherein the variant nucleic acid sequence encodes an IL-2 protein having immune stimulating activity, preferably T helper cell and CD8+ T cell stimulating activity. Even more preferably, the nucleic acid sequence encoding IL-2 shows at least 95%, 96%, 97%, 98% or 99% homology or sequence identity to the nucleic acid sequence of SEQ ID NO: 3 (FIG. 14), wherein the variant nucleic acid sequence encodes an IL-2 protein having immune stimulating activity, preferably T helper cell and CD8+ T cell stimulating activity. In certain embodiments, variants of IL-2 as described above exhibit the same immune stimulating activity, preferably T helper cell and CD8+ T cell stimulating activity, as the native IL-2 encoded by the sequence of SEQ ID NO: 3 (FIG. 14). In a particularly preferred embodiment, the nucleic acid sequence encoding IL-2 comprises (or consists of) the sequence of SEQ ID NO: 3 (FIG. 14). In various preferred embodiments, a variant sequence of the nucleic acid sequence of human IL-2 as described herein is not a nucleotide sequence encoding mouse IL-2. Thus, in various preferred embodiments the novel vector/vector system of the present disclosure does not comprise a nucleic acid sequence encoding IL-2 of mouse origin.

In various embodiments of the disclosure, the nucleic acid sequence encoding scIL-12 shows at least 70% homology or sequence identity to the nucleic acid sequence of SEQ ID NO: 5 (FIG. 15), wherein the variant nucleic acid sequence encodes a scIL-12 protein having immune stimulating activity, preferably T helper cell and CD8+ T cell stimulating activity. Preferably, the nucleic acid sequence encoding scIL-12 shows at least 80% homology or sequence identity to the nucleic acid sequence of SEQ ID NO: 5 (FIG. 15), wherein the variant nucleic acid sequence encodes a scIL-12 protein having immune stimulating activity, preferably T helper cell and CD8+ T cell stimulating activity. More preferably, the nucleic acid sequence encoding scIL-12 shows at least 90% homology or sequence identity to the nucleic acid sequence of SEQ ID NO: 5 (FIG. 15), wherein the variant nucleic acid sequence encodes a scIL-12 protein having immune stimulating activity, preferably T helper cell and CD8+ T cell stimulating activity. Even more preferably, the nucleic acid sequence encoding scIL-12 shows at least 95%, 96%, 97%, 98% or 99% homology or sequence identity to the nucleic acid sequence of SEQ ID NO: 5 (FIG. 15), wherein the variant nucleic acid sequence encodes a scIL-12 protein having immune stimulating activity, preferably T helper cell and CD8+ T cell stimulating activity. As described herein, a protein is considered a scIL-12 protein if it comprises an amino acid sequence comprising the two subunits of the native IL-12 protein as a fusion protein. The sequence of SEQ ID NO: 5 (FIG. 15) shows the sequence of the gene encoding the 40 kDa and 35 kDa subunits of human IL-12 linked by a linker. In the nucleotide sequence of SEQ ID NO: 5 depicted in FIG. 15, the linker sequence is shown in boldface. In certain embodiments, variants of scIL-12 as described above exhibit the same immune stimulating activity, preferably T helper cell and CD8+ T cell stimulating activity, as the native scIL-12 encoded by the sequence of SEQ ID NO: 5 (FIG. 15). In a particularly preferred embodiment, the nucleic acid sequence encoding scIL-12 comprises (or consists of) the sequence of SEQ ID NO: 5 (FIG. 15). In various preferred embodiments, a variant sequence of the nucleic acid sequence of human scIL-12 as described herein is not a nucleotide sequence encoding mouse scIL-12. Thus, in various preferred embodiments the novel vector/vector system of the present disclosure does not comprise a nucleic acid sequence encoding scIL-12 of mouse origin.

In various embodiments of the disclosure, the nucleic acid sequence of (the gene for) 4-1BBL encodes a 4-1BBL polypeptide comprising an amino acid sequence having at least 70% homology or sequence identity to the amino acid sequence of SEQ ID NO: 2 (FIG. 13), wherein the 4-1BBL polypeptide is capable of specifically binding activated T cells, preferably activated CD4+ T helper cells and CD8+ T cells. Preferably, the nucleic acid sequence of (the gene for) 4-1BBL encodes a 4-1BBL polypeptide comprising an amino acid sequence having at least 80% homology or sequence identity to the amino acid sequence of SEQ ID NO: 2 (FIG. 13), wherein the 4-1BBL polypeptide is capable of specifically binding T cells, preferably activated CD4+ T helper cells and CD8+ T cells. More preferably, the nucleic acid sequence of (the gene for) 4-1BBL encodes a 4-1BBL polypeptide comprising an amino acid sequence having at least 90% homology or sequence identity to the amino acid sequence of SEQ ID NO: 2 (FIG. 13), wherein the 4-1BBL polypeptide is capable of specifically binding activated T cells, preferably CD8+ T cells. Even more preferably, the nucleic acid sequence of (the gene for) 4-1BBL encodes a 4-1BBL polypeptide comprising an amino acid sequence having at least 95%, 96%, 97%, 98%, or 99% homology or sequence identity to the amino acid sequence of SEQ ID NO: 2 (FIG. 13), wherein the 4-1BBL polypeptide is capable of specifically binding activated T cells, preferably activated CD4+ T helper cells and CD8+ T cells. In certain embodiments, variant nucleic acid sequences of (the gene for) 4-1BBL as described above encode a 4-1BBL polypeptides, which exhibit the same binding specificity for T cells, preferably for CD8+ T cells, as the native 4-1BBL having the amino acid sequence of SEQ ID NO: 2 (FIG. 13). In a preferred embodiment, the nucleic acid sequence of (the gene for) 4-1BBL encodes a polypeptide comprising (or consisting of) the amino acid sequence of SEQ ID NO: 2 (FIG. 13).

In various embodiments of the disclosure, the nucleic acid sequence of (the gene for) IL-2 encodes an IL-2 polypeptide comprising an amino acid sequence having at least 70% homology or sequence identity to the amino acid sequence of SEQ ID NO: 4 (FIG. 14), wherein the IL-2 polypeptide has immune stimulating activity, preferably T helper cell and CD8+ T cell stimulating activity. Preferably, the nucleic acid sequence of (the gene for) IL-2 encodes an IL-2 polypeptide comprising an amino acid sequence having at least 80% homology or sequence identity to the amino acid sequence of SEQ ID NO: 4 (FIG. 14), wherein the IL-2 polypeptide has immune stimulating activity, preferably T helper cell and CD8+ T cell stimulating activity. More preferably, the nucleic acid sequence of (the gene for) IL-2 encodes an IL-2 polypeptide comprising an amino acid sequence having at least 90% homology or sequence identity to the amino acid sequence of SEQ ID NO: 4 (FIG. 14), wherein the IL-2 polypeptide has immune stimulating activity, preferably T helper cell and CD8+ T cell stimulating activity. Even more preferably, the nucleic acid sequence of (the gene for) IL-2 encodes an IL-2 polypeptide comprising an amino acid sequence having at least 95%, 96%, 97%, 98% or 99% homology or sequence identity to the amino acid sequence of SEQ ID NO: 4 (FIG. 14), wherein the IL-2 polypeptide has immune stimulating activity, preferably T helper cell and CD8+ T cell stimulating activity. In certain embodiments, variant nucleic acid sequences of IL-2 as described above encode IL-2 polypeptides, which exhibit the same immune stimulating activity, preferably T helper cell and CD8+ T cell stimulating activity, as the native IL-2 having the amino acid sequence of SEQ ID NO: 4 (FIG. 14). In a preferred embodiment, the nucleic acid sequence of (the gene for) IL-2 encodes a polypeptide comprising (or consisting of) the amino acid sequence of SEQ ID NO: 4 (FIG. 14).

In various embodiments of the disclosure, the nucleic acid sequence of (the gene for) scIL-12 encodes a scIL-12 polypeptide comprising an amino acid sequence having at least 70% homology or sequence identity to the amino acid sequence of SEQ ID NO: 6 (FIG. 15), wherein the scIL-12 polypeptide has immune stimulating activity, preferably monocyte, T helper cell and CD8+ T cell stimulating activity. Preferably, the nucleic acid sequence of (the gene for) scIL-12 encodes a scIL-12 polypeptide comprising an amino acid sequence having at least 80% homology or sequence identity to the amino acid sequence of SEQ ID NO: 6 (FIG. 15), wherein the scIL-12 polypeptide has immune stimulating activity, preferably monocyte, T helper cell and CD8+ T cell stimulating activity. More preferably, the nucleic acid sequence of (the gene for) scIL-12 encodes a scIL-12 polypeptide comprising an amino acid sequence having at least 90% homology or sequence identity to the amino acid sequence of SEQ ID NO: 6 (FIG. 15), wherein the scIL-12 polypeptide has immune stimulating activity, preferably monocyte, T helper cell and CD8+ T cell stimulating activity. Even more preferably, the nucleic acid sequence of (the gene for) scIL-12 encodes a scIL-12 polypeptide comprising an amino acid sequence having at least 95%, 96%, 97%, 98%, or 99% homology or sequence identity to the amino acid sequence of SEQ ID NO: 6 (FIG. 15), wherein the scIL-12 polypeptide has immune stimulating activity, preferably monocyte, T helper cell and CD8+ T cell stimulating activity. In certain embodiments, variant nucleic acid sequences of scIL-12 as described above encode scIL-12 polypeptides, which exhibit the same immune stimulating activity, preferably T helper cell and CD8+ T cell stimulating activity, as the native scIL-12 having the amino acid sequence of SEQ ID NO: 6 (FIG. 15). In a preferred embodiment, the nucleic acid sequence of (the gene for) scIL-12 encodes a polypeptide comprising (or consisting of) the amino acid sequence of SEQ ID NO: 6 (FIG. 15).

As described herein, one or more poly- or multicistronic expression units may be used that include two or three polynucleotide sequences encoding two or all three proteins, i.e., two polynucleotide sequences each encoding at least (i) 4-1BBL or scIL-12, or (ii) 4-1BBL or IL-2, or (iii) scIL-12 or IL-2; or three polynucleotide sequences each encoding at least 4-1BBL, scIL-12, or 4-1BBL, respectively. The use of multicistronic vectors (or expression units) reduces the total number of nucleic acid molecules required and thus may avoid possible difficulties associated with coordinating expression from multiple vector genomes. In a multicistronic vector the various elements to be expressed may be operatively linked to one or more promoters (and other expression control elements as necessary).

When using several promoters, one may observe mutual inhibition of the promoters. Particularly high expression rates can be achieved using vectors that are at least tricistronic, and which are further characterized in that they contain only one promoter per expression cassette, and furthermore comprise an IRES sequence for each cistron that is not localized immediately downstream of the promoter. The combination of promoters and IRES (internal ribosomal entry sites) sequences is considered to provide for an improved protein expression. The use of different IRES sequences may provide for the additional advantage that the frequency of recombination can be among these sequences can be minimized. In various embodiments of the present disclosure, the IRES is from EMCV (encephalomyocarditis virus). In various embodiments of the present disclosure, the IRES is from PV (poliovirus). In various embodiments of the disclosure, the novel vector/vector system comprises two IRES between the three transgenes 4-1BBL (CD137L), IL-2 and single chain IL-12, wherein one IRES may be the EMCV IRES, and the other IRES may be the PV IRES. In various embodiments of the disclosure, the novel vector/vector system comprises two IRES between the three transgenes 4-1BBL (CD137L), IL-2 and single chain IL-12, wherein both IRES may be the EMCV IRES, or both IRES may be the PV IRES. When using tetracistronic vectors, it may be useful to split them onto different expression cassettes. In this case, it is preferred that one promoter is present per expression cassette. The separation in two expression cassettes, which preferably show the maximum possible distance from each other, provides for spatially separating the promoters, thereby reducing mutual inhibition.

In various embodiments, the novel vector/vector system of the present disclosure comprises the three genes of 4-1BBL (CD137L), IL-2 and single chain IL-12 organized in this order (i.e., 5' to 3' with the gene encoding IL-2 located downstream of the gene encoding 4-1BBL, and the gene encoding scIL-12 located downstream of the gene encoding IL-2) in a tricistronic construct linked by internal ribosomal entry sites (IRES). Preferably, the three genes are genes of human 4-1BBL (CD137L), human IL-2 and human single chain IL-12. More preferably, the three genes are driven by a Cytomegalovirus (CMV) promoter, i.e., the vector system comprises a CMV promoter upstream of the tricistronic construct comprising the three genes of human 4-1BBL (CD137L), human IL-2 and human single chain IL-12. Still more preferably, transcript polyadenylation is induced by a SV40-derived signal, i.e., the novel vector/vector system comprises a gene encoding a SV40 polyadenylation signal downstream of the tricistronic construct comprising the three genes of human 4-1BBL (CD137L), human IL-2 and human single chain IL-12 (human scIL-12). Even more preferably, the vector DNA is adenoviral vector DNA.

Thus, in one preferred embodiment, the novel vector/vector system of the present disclosure comprises an expression cassette comprising (i) the three genes of human 4-1BBL (CD137L), human IL-2 and human single chain IL-12 organized in this order (i.e., 5' to 3' with the gene encoding IL-2 located downstream of the gene encoding 4-1BBL, and the gene encoding scIL-12 located downstream of the gene encoding IL-2) in a tricistronic construct linked by internal ribosomal entry sites (IRES), (ii) a CMV promoter upstream of the tricistronic construct comprising the three genes of human 4-1BBL (CD137L), human IL-2 and human single chain IL-12, and (iii) a gene encoding a SV40 polyadenylation signal downstream of the said tricistronic construct, wherein the vector is an adenoviral vector.

In various embodiments, the novel vector/vector system of the disclosure comprises an expression construct, in which the three genes of 4-1BBL (CD137L), IL-2 and single chain IL-12 are organized as depicted in any one of (a) to (f) below (Prom.=Promoter):

(a) -Prom.>-|hu 4-1BBL|-|hu IL-2|-|hu scIL-12|-
(b) -Prom.>-|hu 4-1BBL|-(IRES)-|hu IL-2|-(IRES)-|hu scIL-12|-
(c) -Prom.>-|hu 4-1BBL|-(IRES)-|hu IL-2|-(IRES)-|hu scIL-12|-|polyA|-
(d) -Prom.>-|hu 4-1BBL|-Prom.>-|hu IL-2|-|hu scIL-12|-
(e) -Prom.>-|hu 4-1BBL|-|hu IL-2|-Prom.>-|hu scIL-12|-
(f) -Prom.>-|hu 4-1BBL|-Prom.>-|hu IL-2|-Prom.>-|hu scIL-12|-

In various embodiments, the novel vector of the present disclosure comprises a promoter upstream of (an expression construct comprising) the three genes of 4-1BBL, IL-2 and scIL-12 organized in an order as described elsewhere herein.

Preferably, the gene of human 4-1BBL is at position 1 of the three genes of the novel vector, more specifically at position 1 of the expression construct comprising the said three genes.

In various embodiments, the novel vector of the present disclosure comprises an expression cassette comprising a nucleic acid sequence having at least 70% homology or sequence identity to the nucleic acid sequence of SEQ ID NO: 12 (FIG. 18), wherein expression of the variant nucleic acid sequence provides for the same immune stimulating activity, preferably T helper cell and CD8+ T cell stimulating activity, as the expression of the expression cassette of SEQ ID NO: 12. Preferably, the expression cassette comprises a nucleic acid sequence having at least 80% homology or sequence identity to the nucleic acid sequence of SEQ ID NO: 12 (FIG. 18), wherein expression of the variant nucleic acid sequence provides for the same immune stimulating activity, preferably T helper cell and CD8+ T cell stimulating activity, as the expression of the expression cassette of SEQ ID NO: 12. More preferably, the expression cassette comprises a nucleic acid sequence having at least 90% homology or sequence identity to the nucleic acid sequence of SEQ ID NO: 12 (FIG. 18), wherein expression of the variant nucleic acid sequence provides for the same immune stimulating activity, preferably T helper cell and CD8+ T cell stimulating activity, as the expression of the expression cassette of SEQ ID NO: 12. Even more preferably, the expression cassette comprises a nucleic acid sequence having at least 95%, 96%, 97%, 98% or 99% homology or sequence identity to the nucleic acid sequence of SEQ ID NO: 12 (FIG. 18), wherein expression of the variant nucleic acid sequence provides for the same immune stimulating activity, preferably T helper cell and CD8+ T cell stimulating activity, as the expression of the expression cassette of SEQ ID NO: 12. In a preferred embodiment, the novel vector of the present disclosure comprises an expression cassette comprising (or consisting of) the nucleic acid sequence of SEQ ID NO: 12 (FIG. 18).

In various embodiments, the novel vector of the present disclosure comprises an expression cassette comprising a nucleic acid sequence having at least 70% homology or sequence identity to a reference expression cassette comprising the following nucleic acid sequences of SEQ ID NO: 11 (FIG. 17): (i) the nucleic acid sequence of bp 1,080-1,844 (human 4-1BBL), (ii) the nucleic acid sequence of bp 1,885-2,388 (EMCV IRES), (iii) the nucleic acid sequence of bp 2,409-2,870 (human IL-2), (iv) the nucleic acid sequence of bp 2,914-3,545 (PV IRES), and (v) the nucleic acid sequence of bp 3,581-5,203 (human scIL-12 comprising p40 and p35 subunit of human IL-12 linked by a linker), wherein expression of the variant expression cassette provides for the same immune stimulating activity, preferably T helper cell and CD8+ T cell stimulating activity, as the expression of the said reference expression cassette. Preferably, the expression cassette comprises a nucleic acid sequence having at least 80% homology or sequence identity to the said reference expression cassette, wherein expression of the variant expression cassette provides for the same immune stimulating activity, preferably T helper cell and CD8+ T cell stimulating activity, as the expression of the said reference expression cassette. More preferably, the expression cassette comprises a nucleic acid sequence having at least 90% homology or sequence identity to the said reference expression cassette, wherein expression of the variant expression cassette provides for the same immune stimulating activity, preferably T helper cell and CD8+ T cell stimulating activity, as the expression of the said reference expression cassette. Even more preferably, the expression cassette comprises a nucleic acid sequence having at least 95%, 96%, 97%, 98% or 99% homology or sequence identity to the said reference expression cassette, wherein expression of the variant expression cassette provides for the same immune stimulating activity, preferably T helper cell and CD8+ T cell stimulating activity, as the expression of the said reference expression cassette. In a preferred embodiment, the novel vector of the present disclosure comprises an expression cassette comprising (or consisting of) the following nucleic acid sequences of SEQ ID NO: 11 (FIG. 17): (i) the nucleic acid sequence of bp 1,080-1,844 (human 4-1BBL), (ii) the nucleic acid sequence of bp 1,885-2,388 (EMCV IRES), (iii) the nucleic acid sequence of bp 2,409-2,870 (human IL-2), (iv) the nucleic acid sequence of bp 2,914-3,545 (PV IRES), and (v) the nucleic acid sequence of bp 3,581-5,203 (human scIL-12 comprising p40 and p35 subunit of human IL-12 linked by a linker).

In various embodiments, the novel vector of the present disclosure comprises an expression cassette comprising a nucleic acid sequence having at least 70% homology or sequence identity to a reference expression cassette comprising the following nucleic acid sequences of SEQ ID NO: 11 (FIG. 17): (i) the nucleic acid sequence of bp 484-1,059 (CMV promoter), (ii) the nucleic acid sequence of bp 1,080-1,844 (human 4-1BBL), (iii) the nucleic acid sequence of bp 1,885-2,388 (EMCV IRES), (iv) the nucleic acid sequence of bp 2,409-2,870 (human IL-2), (v) the nucleic acid sequence of bp 2,914-3,545 (PV IRES), (vi) the nucleic acid sequence of bp 3,581-5,203 (human scIL-12 comprising p40 and p35 subunit of human IL-12 linked by a linker), and (vii) the nucleic acid sequence of bp 5,271-5,510 (SVpolyA), wherein expression of the variant expression cassette provides for the same immune stimulating activity, preferably T helper cell and CD8+ T cell stimulating activity, as the expression of the said reference expression cassette. Preferably, the expression cassette comprises a nucleic acid sequence having at least 80% homology or sequence identity to the said reference expression cassette, wherein expression of the variant expression cassette provides for the same immune stimulating activity, preferably T helper cell and CD8+ T cell stimulating activity, as the expression of the said reference expression cassette. More preferably, the expression cassette comprises a nucleic acid sequence having at least 90% homology or sequence identity to the said reference expression cassette, wherein expression of the variant expression cassette provides for the same immune stimulating activity, preferably T helper cell and CD8+ T cell stimulating activity, as the expression of the said reference expression cassette. Even more preferably, the expression cassette comprises a nucleic acid sequence having at least 95%, 96%, 97%, 98% or 99% homology or sequence identity to the said reference expression cassette, wherein expression of the variant expression cassette provides for the same immune stimulating activity, preferably T helper cell and CD8+ T cell stimulating activity, as the expression of the said reference expression cassette. In a preferred embodiment, the novel vector of the present disclosure comprises an expression cassette comprising (or consisting of) the following nucleic acid sequences of SEQ ID NO: 11 (FIG. 17): (i) the nucleic acid sequence of bp 484-1,059 (CMV promoter), (ii) the nucleic acid sequence of bp 1,080-1,844 (human 4-1BBL), (iii) the nucleic acid sequence of bp 1,885-2,388 (EMCV IRES), (iv) the nucleic acid sequence of bp 2,409-2,870 (human IL-2), (v) the nucleic acid sequence of bp 2,914-3,545 (PV IRES), (vi) the nucleic acid sequence of bp 3,581-5,203 (human scIL-12 comprising p40 and p35 subunit of human IL-12 linked by a linker), and (vii) the nucleic acid sequence of bp 5,271-5,510 (SVpolyA).

In various embodiments, the vector system comprises the three genes of 4-1BBL (CD137L), IL-2 and single chain IL-12 organized in three separate vectors. Preferably, the three genes are human genes of 4-1BBL (CD137L), IL-2 and single chain IL-12. More preferably, the three genes are each driven by a Cytomegalovirus (CMV) promoter, i.e., each vector comprises a CMV promoter upstream of the gene of human 4-1BBL (CD137L), human IL-2 and human single chain IL-12, respectively. Still more preferably, transcript polyadenylation is induced by a SV40-derived signal, i.e., each vector system comprises a gene encoding a SV40 polyadenylation signal downstream of the gene of human 4-1BBL (CD137L), human IL-2 and human single chain IL-12 (human scIL-12), respectively. Even more preferably, the vector DNA of each separate vector is adenoviral vector DNA.

Thus, in one preferred embodiment, the vector system comprises three adenoviral vectors, each comprising (i) the gene of human 4-1BBL (CD137L), human IL-2 or human single chain IL-12, (ii) a CMV promoter upstream of the gene of human 4-1BBL (CD137L), human IL-2 and human single chain IL-12, respectively, and (iii) a nucleic acid sequence encoding a SV40 polyadenylation signal downstream of the gene of human 4-1BBL (CD137L), human IL-2 and human single chain IL-12, respectively.

In various aspects, the vector system comprises the three genes of 4-1BBL (CD137L), IL-2 and single chain IL-12 organized in two separate vectors. Specifically, in various embodiments, one of the two vectors comprises the genes of 4-1BBL (CD137L) and IL-2, and the other vector comprises the gene of single chain IL-12. Preferably, the genes are human genes of 4-1BBL (CD137L), IL-2 and single chain IL-12. More preferably, the genes are driven by a Cytomegalovirus (CMV) promoter, i.e., the vector comprising the genes of human 4-1BBL (CD137L) and human IL-2 comprises a CMV promoter upstream of the gene of human 4-1BBL (CD137L) in case the gene of human 4-1BBL (CD137L) is located upstream of the gene of human IL-2, or upstream of the gene of human IL-2 in case the gene of human IL-2 is located upstream of the gene of human 4-1BBL (CD137L), and the vector comprising the gene of human scIL-12 comprises a CMV promoter upstream of the gene of human scIL-12. Still more preferably, transcript polyadenylation is induced by a SV40-derived signal, i.e., each of the two vectors comprises a nucleic acid sequence encoding a SV40 polyadenylation signal, i.e., the vector comprising the genes of human 4-1BBL (CD137L) and human IL-2 comprises a gene encoding a SV40 polyadenylation signal downstream of the gene of human IL-2 in case the gene of human 4-1BBL (CD137L) is located upstream of the gene of human IL-2, or comprises a gene encoding a SV40 polyadenylation signal downstream of the gene of human 4-1BBL (CD137L) in case the gene of human IL-2 is located upstream of the gene of human 4-1BBL (CD137L), and the vector comprising the gene of human scIL-12 comprises a nucleic acid sequence encoding a SV40 polyadenylation signal downstream of the gene of human scIL-12. Even more preferably, the vector DNA of each separate vector is adenoviral vector DNA.

Thus, in one preferred embodiment, the vector system comprises two adenoviral vectors, one comprising the genes of human 4-1BBL (CD137L) and human IL-2, and the other comprising the gene of human scIL-12, wherein (i) the vector comprising the genes of human 4-1BBL (CD137L)

and human IL-2 further comprises a CMV promoter upstream of the gene of human 4-1BBL (CD137L) in case the gene of human 4-1BBL (CD137L) is located upstream of the gene of human IL-2, or upstream of the gene of human IL-2 in case the gene of human IL-2 is located upstream of the gene of human 4-1BBL (CD137L), and wherein the vector comprising the gene of human scIL-12 comprises a CMV promoter upstream of the gene of human scIL-12, and (ii) the vector comprising the genes of human 4-1BBL (CD137L) and human IL-2 still further comprises a gene encoding a SV40 polyadenylation signal downstream of the gene of human IL-2 in case the nucleic acid sequence of human 4-1BBL (CD137L) is located upstream of the gene of human IL-2, or a gene encoding a SV40 polyadenylation signal downstream of the gene of human 4-1BBL (CD137L) in case the gene of human IL-2 is located upstream of the gene of human 4-1BBL (CD137L), and wherein the vector comprising the gene of human scIL-12 comprises a gene encoding a SV40 polyadenylation signal downstream of the gene of human scIL-12.

In various other embodiments, the vector system comprises two separate vectors, wherein one of the two vectors comprises the genes of 4-1BBL (CD137L) and single chain IL-12 (scIL-12), and the other vector comprises the gene of IL-2. Preferably, the genes are human genes of 4-1BBL (CD137L), scIL-12 and IL-2. More preferably, the genes are driven by a Cytomegalovirus (CMV) promoter, i.e., the vector comprising the genes of human 4-1BBL (CD137L) and human scIL-12 comprises a CMV promoter upstream of the gene of human 4-1BBL (CD137L) in case the gene of human 4-1BBL (CD137L) is located upstream of the gene of human scIL-12, or upstream of the gene of human scIL-12 in case the gene of human scIL-12 is located upstream of the gene of human 4-1BBL (CD137L), and the vector comprising the gene of human IL-2 comprises a CMV promoter upstream of the gene of human IL-2. Still more preferably, transcript polyadenylation is induced by a SV40-derived signal, i.e., each of the two vectors comprises a nucleic acid sequence encoding a SV40 polyadenylation signal, i.e., the vector comprising the genes of human 4-1BBL (CD137L) and human scIL-12 comprises a gene encoding a SV40 polyadenylation signal downstream of the gene of human scIL-12 in case the gene of human 4-1BBL (CD137L) is located upstream of the gene of human scIL-12, or comprises a gene encoding a SV40 polyadenylation signal downstream of the gene of human 4-1BBL (CD137L) in case the gene of human scIL-12 is located upstream of the gene of human 4-1BBL (CD137L), and the vector comprising the gene of human IL-2 comprises a nucleic acid sequence encoding a SV40 polyadenylation signal downstream of the gene of human IL-2. Even more preferably, the vector DNA of each separate vector is adenoviral vector DNA.

Thus, in one preferred embodiment, the vector system comprises two adenoviral vectors, one comprising the genes of human 4-1BBL (CD137L) and human scIL-12, and the other comprising the gene of human IL-2, wherein (i) the vector comprising the genes of human 4-1BBL (CD137L) and human scIL-12 further comprises a CMV promoter upstream of the gene of human 4-1BBL (CD137L) in case the gene of human 4-1BBL (CD137L) is located upstream of the gene of human scIL-12, or upstream of the gene of human scIL-12 in case the gene of human scIL-12 is located upstream of the gene of human 4-1BBL (CD137L), and wherein the vector comprising the gene of human IL-2 comprises a CMV promoter upstream of the gene of human IL-2, and (ii) the vector comprising the genes of human 4-1BBL (CD137L) and human scIL-12 still further comprises a gene encoding a SV40 polyadenylation signal downstream of the gene of human scIL-12 in case the gene of human 4-1BBL (CD137L) is located upstream of the gene of human scIL-12, or a nucleic acid sequence encoding a SV40 polyadenylation signal downstream of the gene of human 4-1BBL (CD137L) in case the gene of human scIL-12 is located upstream of the gene of human 4-1BBL (CD137L), and wherein the vector comprising the gene of human IL-2 comprises a nucleic acid sequence encoding a SV40 polyadenylation signal downstream of the gene of human IL-2.

In various other embodiments, the vector system comprises two separate vectors, wherein one of the two vectors comprises the genes of IL-2 and single chain IL-12 (scIL-12), and the other vector comprises the gene of 4-1BBL (CD137L). Preferably, the genes are human genes of IL-2, scIL-12 and 4-1BBL (CD137L). More preferably, the genes are driven by a Cytomegalovirus (CMV) promoter, i.e., the vector comprising the genes of human IL-2 and human scIL-12 comprises a CMV promoter upstream of the gene of human IL-2 in case the gene of human IL-2 is located upstream of the gene of human scIL-12, or upstream of the gene of human scIL-12 in case the gene of human scIL-12 is located upstream of the gene of human IL-2, and the vector comprising the gene of human 4-1BBL (CD137L) comprises a CMV promoter upstream of the gene of human 4-1BBL (CD137L). Still more preferably, transcript polyadenylation is induced by a SV40-derived signal, i.e., each of the two vectors comprises a nucleic acid sequence encoding a SV40 polyadenylation signal, i.e., the vector comprising the genes of human IL-2 and human scIL-12 comprises a nucleic acid sequence encoding a SV40 polyadenylation signal downstream of the gene of human scIL-12 in case the gene of human IL-2 is located upstream of the gene of human scIL-12, or comprises a nucleic acid sequence encoding a SV40 polyadenylation signal downstream of the gene of human IL-2 in case the gene of human scIL-12 is located upstream of the gene of human IL-2, and the vector comprising the gene of human 4-1BBL (CD137L) comprises a nucleic acid sequence encoding a SV40 polyadenylation signal downstream of the gene of human 4-1BBL (CD137L). Even more preferably, the vector DNA of each separate vector is adenoviral vector DNA.

Thus, in one preferred embodiment, the vector system comprises two adenoviral vectors, one comprising the genes of human IL-2 and human scIL-12, and the other comprising the gene of human 4-1BBL (CD137L), wherein (i) the vector comprising the genes of human IL-2 and human scIL-12 further comprises a CMV promoter upstream of the gene of human IL-2 in case the gene of human IL-2 is located upstream of the gene of human scIL-12, or upstream of the gene of human scIL-12 in case the gene of human scIL-12 is located upstream of the gene of human IL-2, and wherein the vector comprising the gene of human 4-1BBL (CD137L) comprises a CMV promoter upstream of the gene of human 4-1BBL (CD137L), and (ii) the vector comprising the genes of human IL-2 and human scIL-12 still further comprises a gene encoding a SV40 polyadenylation signal downstream of the gene of human scIL-12 in case the gene of human IL-2 is located upstream of the gene of human scIL-12, or a nucleic acid sequence encoding a SV40 polyadenylation signal downstream of the gene of human IL-2 in case the gene of human scIL-12 is located upstream of the gene of human IL-2, and wherein the vector comprising the gene of human 4-1BBL (CD137L) comprises a nucleic acid sequence encoding a SV40 polyadenylation signal downstream of the gene of human 4-1BBL (CD137L). For virus particles of the disclosure, the expression units further include a sequence encoding an envelope/capsid molecule or one or more maturation factors necessary for production of the desired vector particle in packaging cells.

Internal ribosome entry sites (IRES) elements are used to create multigene, or multi- or polycistronic, messages. IRES elements are able to bypass the ribosome scanning model of 5' methylated Cap dependent translation and begin translation at internal sites. IRES elements can be linked to heterologous open reading frames. Multiple open reading frames can be transcribed together, each separated by an IRES, creating multi- or polycistronic messages. Each component to be expressed in a multicistronic expression vector may be separated by an IRES element to allow for separate expression of the various proteins from the same promoter. Tools that can be used to separate genetic elements in a multicistronic vector, in particular IRES elements, are known in the art. The efficacy of a particular multicistronic vector can readily be tested by detecting expression of each of the genes using standard protocols. In various embodiments of the present disclosure, the nucleic acid sequence(s) encoding at least 4-1BBL, scIL-12 and IL-2 are organized in one vector, wherein the nucleic acid sequence(s) encoding scIL-12 and IL-2 are located downstream of the nucleic acid sequence encoding 4-1BBL. Such a vector is considered a multicistronic expression vector. In certain embodiments, the multicistronic expression vector is a tricistronic expression vector containing the nucleic acid sequences (of the genes) encoding 4-1BBL, scIL-12 and IL-2, wherein the genes are organized in 5' to 3' orientation in a sequential order 1, 2, 3, with the proviso that the gene encoding scIL-12 is not at position 1. In various embodiments, the nucleic acid sequence(s) encoding scIL-12 and IL-2 are located downstream of the nucleic acid sequence encoding 4-1BBL. Preferably, in a multicistronic or tricistronic expression vector, the nucleic acid sequence encoding IL-2 is located downstream of the nucleic acid sequence encoding 4-1BBL, and the nucleic acid sequence encoding scIL-12 is located downstream of the nucleic acid sequence encoding IL-2. In various embodiments of a multicistronic or tricistronic expression, a promoter is located upstream of the nucleic acid sequence encoding 4-1BBL, but not upstream of the nucleic acid sequence(s) encoding scIL-12 and/or IL-2.

In certain embodiments of a multicistronic or tricistronic expression vector, the nucleic acid sequence(s) encoding at least 4-1BBL, scIL-12 and/or IL-2 are linked by internal ribosomal entry sites (IRES).

In a specific exemplification, a viral vector genome comprises: an enhancer/promoter sequence, preferably a cytomegalovirus (CMV) enhancer/promoter sequence; the R and U5 sequences from a virus 5' LTR; optionally a packaging sequence; an internal enhancer; an internal promoter; one or more polynucleotides encoding at least 4-1BBL, scIL-12 and/or IL-12; a U3 element with a deletion of its enhancer sequence; and the R and U5 sequences of a viral 3' LTR. Construction of the vector genome can be accomplished using any suitable genetic engineering techniques known in the art, including, without limitation, the standard techniques of restriction endonuclease digestion, ligation, transformation, plasmid purification, and DNA sequencing, for example as described, e.g., in Sambrook et al. (1989 and 2001 editions; Molecular Cloning: A Laboratory Manual, Cold Spring Harbor Laboratory Press, NY). Vectors constructed for transient expression in mammalian cells may also be used. Transient expression involves the use of an expression vector that is able to replicate efficiently in a host cell, such that the host cell accumulates many copies of the expression vector and, in turn, synthesizes high levels of a the polypeptide encoded by the polynucleotide in the expression vector. See Sambrook et al., supra, pp. 16.17-16.22, 1989. Other vectors and methods suitable for adaptation to the expression of polypeptides are well known in the art and are readily adapted to the specific circumstances.

By using the teachings provided herein and the knowledge in the art, a person skilled in the art will recognize that the efficacy of a particular expression system can be tested by transfecting packaging cells with a vector comprising a polynucleotide sequence encoding a reporter protein and measuring the expression using a suitable technique, for example, measuring fluorescence from a green fluorescent protein conjugate. Other suitable reporter genes are well known in the art.

It is also contemplated by the present disclosure that in certain embodiments the novel vector/vector system provided by the present disclosure may comprise native IL-12 instead of scIL-12, i.e., may comprise a nucleic acid sequence (of a gene) encoding native IL-12. IL-12 is a disulfide-linked heterodimeric cytokine composed of the two separately encoded p35 and p40 subunits. In various embodiments, the nucleic acid sequence (of a gene) may encode native human IL-12. Accordingly, in various embodiments, the novel vector/vector system provided by the present disclosure may comprise three genes encoding (i) 4-1BB ligand (4-1BBL), (ii) IL-12 p40 and p35 subunits, and (iii) IL-2, wherein the said genes are organized in 5' to 3' orientation in a sequential order 1, 2, and 3 with the proviso that the gene(s) encoding the IL-12 p35 and IL-12 p40 subunits is/are not at position 1.

In various embodiments, the novel vector/vector system of the present disclosure may comprise three genes encoding 4-1BB ligand (4-1BBL), native IL-12, and IL-2, wherein the said genes are organized in 5' to 3' orientation in a sequential order 1, 2, and 3, with the proviso that the gene(s) encoding the IL-12 p35 and p40 subunits is/are not at position 1, wherein the gene(s) encoding IL-12 subunits p40 and p35 may comprise a nucleic acid sequence having at least 70% homology or sequence identity to the nucleic acid sequences of SEQ ID NOs: 7 and 9 (FIG. 16), wherein the variant nucleic acids sequence encodes an IL-12 protein having immune stimulating activity, preferably T helper cell and CD8+ T cell stimulating activity. Preferably, the gene(s) encoding IL-12 subunits p35 and p40 may comprise a nucleic acid sequence having at least 80% homology or sequence identity to the nucleic acid sequences of SEQ ID NOs: 7 and 9 (FIG. 16), wherein the variant nucleic acids sequence encodes an IL-12 protein having immune stimulating activity, preferably T helper cell and CD8+ T cell stimulating activity. More preferably, the gene(s) encoding IL-12 subunits p40 and p35 may comprise a nucleic acid sequence having at least 90% homology or sequence identity to the nucleic acid sequences of SEQ ID NOs: 7 and 9 (FIG. 16), wherein the variant nucleic acids sequence encodes an IL-12 protein having immune stimulating activity, preferably T helper cell and CD8+ T cell stimulating activity. Even more preferably, the gene(s) encoding IL-12 subunits p40 and p35 may comprise a nucleic acid sequence having at least 95%, 96%, 97%, 98% or 99% homology or sequence identity to the nucleic acid sequences of SEQ ID NOs: 7 and 9 (FIG. 16), wherein the variant nucleic acid sequence encodes an IL-12 protein having immune stimulating activity, preferably T helper cell and CD8+ T cell stimulating activity. In particularly preferred embodiments, the gene(s) encoding IL-12 subunits p40 and p35 may comprise the nucleic acid sequences of SEQ ID NOs: 7 and 9 (FIG. 16). In certain embodiments, variants of IL-12 subunits p35 and p40 as described above exhibit the same immune stimulating activity, preferably T helper cell and CD8+ T cell stimulating activity, as the IL-12 subunits p35 and p40 encoded by the sequences of SEQ ID NOs: 7 and 9.

In various embodiments, the gene(s) of IL-12 subunits p40 and p35 encode a polypeptide having at least 70% homology or sequence identity to the amino acid sequences of SEQ ID NOs: 8 and 10 (FIG. 16), wherein the polypeptide has immune stimulating activity, preferably T helper cell and CD8+ T cell stimulating activity. Preferably, the gene(s) of IL-12 subunits p40 and p35 encode(s) a polypeptide having at least 70% homology or sequence identity to the amino acid sequences of SEQ ID NOs: 8 and 10 (FIG. 16), wherein the polypeptide has immune stimulating activity, preferably T helper cell and CD8+ T cell stimulating activity. More preferably, the gene(s) of IL-12 subunits p40 and p35 encode(s) a polypeptide having at least 90% or 95% homology or sequence identity to the amino acid sequences of SEQ ID NOs: 8 and 10 (FIG. 16), wherein the polypeptide has immune stimulating activity, preferably T helper cell and CD8+ T cell stimulating activity. Even more preferably, the gene(s) of IL-12 subunits p40 and p35 encode(s) a polypeptide having the amino acid sequences of SEQ ID NOs: 8 and 10 (FIG. 16).

Preferably, a variant sequence of the nucleic acid sequence of human IL-12 subunits p35 and p40 as described herein is not a nucleotide sequence encoding the mouse IL-12 subunits p35 and p40. Thus, preferably the novel vector/vector system of the present disclosure comprising three genes encoding 4-1BB ligand (4-1BBL), IL-12 subunits p35 and p40, and IL-2 as described above (i.e., wherein the said genes are organized in 5' to 3' orientation in a sequential order 1, 2, and 3, with the proviso that the gene(s) encoding IL-12 subunits p35 and p40 is/are not at position 1), does not comprise a nucleic acid sequence encoding IL-12 subunits p35 and p40 of mouse origin.

In another embodiment, vector particles are provided. The present disclosure provides virus particles comprising a vector system of the present disclosure. A vector particle comprises any one of the novel vector/vector systems described herein that comprise one or more vectors comprising polynucleotide sequence(s) encoding at least 4-1BBL, scIL-12 and/or IL-2. Also provided herein are methods for delivering a vector system of the disclosure encoding at least 4-1BBL, scIL-12 and/or IL-2 (as described herein) to a target cell. Such methods comprise contacting (i.e., permitting interaction) of the target cell with a vehicle that delivers the vector system of the disclosure. In particular embodiments, methods for delivering the novel vector/vector system comprise contacting the cell by administering to a subject a vector particle that comprises a novel vector/vector system of the disclosure that that comprises one or more vectors comprising polynucleotide sequence(s) encoding at least 4-1BBL, scIL-12 and/or IL-2. In certain embodiments, the vector particle is a viral vector particle and the one or more vectors of the novel vector/vector system is any of a RNA vector, a plasmid vector, a nanoparticle vector, and naked DNA. In other certain embodiments, the vector particle is a particle derived from bacteria such as, for example, *Listeria monocytogenes, Salmonella* spp., *Mycobacterium bovis, Escherichia coli, Shigella* spp., and *Yersinia* spp., and the one or more vectors of the vector system is any of a RNA vector, a plasmid vector, a nanoparticle vector, and naked DNA. Exemplary viral vector particles include a lentiviral vector particle that comprises a lentiviral vector genome; a poxvirus vector particle that comprises a poxvirus vector genome; a vaccinia virus vector particle that comprises a vaccinia virus vector genome; an adenovirus vector particle that comprises a adenovirus vector genome; an adenovirus-associated virus vector particle that comprises a adenovirus-associated virus vector genome; a herpes virus vector particle that comprises a herpes virus vector genome (e.g., Herpes simplex virus I or II); or an alpha virus vector particle that comprises an alpha virus vector genome.

The vector particles (e.g., the viral vector particles described herein) may be injected in vivo, in particular to a tumor, where the particles provide for an immunostimulating effect by expression of 4-1BBL, scIL-12, and IL-2. The amount of viral particles is at least $3 \times 10^6$ ivp (infectious viral particles), and can be at least $1 \times 10^7$ ivp, at least $3 \times 10^7$ ivp, at least $1 \times 10^8$ ivp, at least $3 \times 10^8$ ivp, at least $1 \times 10^9$ ivp, or at least $3 \times 10^9$ ivp. At selected intervals, cells from the recipient's malignant (tumor) or target pathogen-infected tissue may be used to measure expression of 4-1BBL, scIL-12 and IL-2, for example, by observing marker expression, such as GFP or luciferase if co-expressed by a polynucleotide sequence present in the vector system included in the vector particle. In particular, T-cells from malignant (tumor) or target pathogen-infected tissue of vector particle-treated recipients may be measured for expression of 4-1BBL, scIL-12 and IL-2.

The term "replication competent adenoviral vector" refers to any adenoviral vector that is not deficient in any gene function required for viral replication in specific cells or tissues. The vector must is capable of replicating and being packaged, but might replicate only conditionally in specific cells or tissues.

Adenovirus (Ad) is a large (about 36 kb) DNA virus that infects humans, but which displays a broad host range. There are approximately 50 serotypes of human adenovirus, which are divided into six families based on molecular, immunological, and functional criteria. By adulthood, virtually every human has been infected with the more common adenovirus serotypes, the major effect being cold-like symptoms. Adenoviral infection of host cells results in adenoviral DNA being maintained episomally, which reduces the potential genotoxicity associated with integrating vectors. Also, adenoviruses are structurally stable, and no genome rearrangement has been detected after extensive amplification.

The adenoviral vectors used in the present disclosure can be any adenoviral vectors suitable for use in a method of treating a human or animal. Alternatively, various types of adenoviral vectors can be used according to the present disclosure. Also, the vectors may be modified in any way known in the art, e.g. by deleting, inserting, mutating or modifying any viral areas. The vectors can be made tumor specific with regard to replication. For example, the adenoviral vector may comprise modifications in E1, E3 and/or E4 such as the insertion of tumor specific promoters, deletions of areas and insertion of transgenes.

Human Ad-5 is a human adenovirus serotype that is well characterized genetically and biochemically (GenBank M73260; AC_000008). Thus, in a preferred embodiment, the adenovirus is a replication competent Ad5 serotype or a hybrid serotype comprising an Ad5 component. The adenovirus may be a wild type strain or may be genetically modified to enhance tumor selectivity, for example by attenuating the ability of the virus to replicate within normal quiescent cells without affecting the ability of the virus to replicate in tumor cells. Non-limiting examples of adenoviruses encompassed by the present disclosure include Delta-24, Delta-24-RGD, ICOVIR-5, ICOVIR-7, ONYX-015, ColoAd1, and H1O1. In one particular embodiment, the adenovirus is Delta-24 or Delta-24-RGD. The Delta-24 adenovirus is derived from adenovirus type 5 (Ad-5) and contains a 24-base-pair deletion within the CR2 portion of the E1A gene. Delta-24-RGD further comprises an insertion of the RGD-4C sequence. The E1A deletion increases the selectivity of the virus for cancer cells; the RGD-4C sequence increases the infectivity of the virus in gliomas.

Furthermore, the backbone of the adenoviral vector may be of any serotype. Still further, the vectors may be chimeric vectors, e.g. Ad5/3 vectors. As an example, "Ad5/3 vector" refers to a chimeric vector having parts of both Ad5 and Ad3 vectors.

The adenovirus is an attractive delivery system, and is well-established for use in gene transfer in several therapeutic applications. The adenovirus enters the permissive host cell via a cell surface receptor, and it is then internalized.

The absence or the presence of low levels of the coxsackie virus and adenovirus receptor (CAR) on tumor types can limit the efficacy of the adenovirus. Modifying the capsid allows CAR independent target cell infection. Also, adenoviral uptake into target tissue can be improved by the addition of transfectant-like polycationic compounds. It has been demonstrated herein (see Example 10) that the adenoviral uptake is particularly improved using the transfectant protamine sulfate. Thus, in various embodiments, protamine sulfate is used for transfection of the vector systems of the present disclosure, preferably for transfection of an adenoviral vector system of the disclosure.

In expression, one will typically include a polyadenylation signal to effect proper polyadenylation of the transcript. The nature of the polyadenylation signal is not believed to be crucial to the successful practice of the present disclosure, and any such sequence may be employed. Preferred embodiments include the SV40 polyadenylation signal and/or the bovine growth hormone polyadenylation signal, convenient and/or known to function well in various target cells. Also contemplated herein as an element of the expression construct is a transcriptional termination site. These elements can serve to enhance message levels and/or to minimize read through from the cassette into other sequences.

In certain embodiments of the disclosure, cells infected by the novel vector/vector system of the disclosure may be identified in vitro by including a reporter gene in the vector system. Generally, a selectable reporter is one that confers a property that allows for selection. A positive selectable reporter is one in which the presence of the reporter gene allows for its selection, while a negative selectable reporter is one in which its presence prevents its selection. An example of a positive selectable marker is a drug resistance marker. Other types of reporters include screenable reporters such as GFP (green fluorescent protein).

Embodiments of the disclosure can use current viral vector platform technologies designed to create vaccines or gene therapy constructs. Aspects of the viral vector construction include inserting genetic material into a viral vector and confirming the construct through characterization and sequencing of the nucleic acid, virus and virus product. The viral vector is then put through a series of feasibilities studies designed to assess scalability.

The present disclosure provides a polynucleotide comprising a nucleic acid sequence encoding the novel vector/vector system of the disclosure.

Furthermore, the present disclosure provides a composition comprising the novel vector/vector system or a virus particle as disclosed herein. The present disclosure also provides a composition comprising a polynucleotide disclosed herein, i.e., a polynucleotide comprising a nucleic acid sequence encoding the novel vector/vector system of the disclosure.

Without being bound by theory, the use of the novel vector/vector system expressing 4-1BBL, scIL-12 and IL-2 results in the local production of cytokines in or around the tumor, which will direct systemically or locally induced tumor specific cytotoxic T-cells to the site of the cancer. Through the immune-stimulatory effect provided by this mechanism, the efficacy of immunotherapy of cancers, viral infections and immune system disorders will be greatly enhanced. The immunostimulating effect provided by the novel vector/vector system of the present disclosure has been demonstrated in the examples.

The present disclosure encompasses compositions comprising the novel vector/vector system or virus particle disclosed herein for use as a medicament. The present disclosure provides a medicament comprising the novel vector/vector system or a virus particle disclosed herein. The present disclosure also provides a medicament comprising a polynucleotide disclosed herein, i.e., a polynucleotide comprising a nucleic acid sequence encoding the novel vector/vector system of the disclosure.

The present disclosure encompasses the novel vector/vector system or virus particle disclosed herein for use as a therapeutic vaccine, more specifically for use as a therapeutic vaccine for the treatment of cancer or viral infections.

The present disclosure also provides an immune cell or a cancer cell transduced or transfected with the novel vector/vector system or a virus particle disclosed herein. Such transduced or transfected cells may be used for ex vivo therapies, in particular ex vivo cancer therapy. In various embodiments of such therapies, at least 5% of the cancer cells transduced or transfected with the novel vector/vector system or a virus particle disclosed herein are expressing 4-1BBL.

In the present disclosure, the cancer cell preferably is a cell of a tumor, i.e., a tumor cell, more specifically a cell of a solid tumor.

Furthermore, the present disclosure provides a composition comprising such an immune cell or cancer cell transduced or transfected with the novel vector/vector system or a virus particle disclosed herein. Still further, the present disclosure provides a medicament comprising such an immune cell or cancer cell transduced or transfected with the novel vector/vector system or a virus particle disclosed herein. In various embodiments, the immune cell is a T-cell, an NK cell, a monocyte lineage cell type (macrophages, dendritic cells, Langerhans cells, mast cells), a fibroblast. In various embodiments, at least 5% of the cancer cells transduced or transfected with the novel vector/vector system or a virus particle disclosed herein are expressing 4-1BBL. The novel vector/vector system or the virus particles of the present disclosure can be used in methods for treating or ameliorating cancer, viral infections and/or immune system disorders. Also, the polynucleotide of the present disclosure can be used in the treatment of cancer, viral infections and/or immune system disorders. Also, the above described composition or medicament of the disclosure can be used in the treatment of cancers, viral infections and/or immune system disorders. In various embodiments, the novel vector/vector system or virus particles of the disclosure can be considered as active agents. Also, in various embodiments the polynucleotide of the disclosure, i.e., a polynucleotide comprising a nucleic acid sequence encoding the novel vector/vector system of the disclosure, and the cancer cell transduced or transfected with the novel vector/vector system or a virus particle disclosed herein, can be considered as active agents. This applies in particular in the context of the medical treatments disclosed herein.

The present disclosure provides a method for treating or ameliorating cancer, a viral infectious disease (viral infection), or an immune system disorder comprising administering to a subject in need thereof a therapeutically effective amount of the novel vector/vector system or a virus particle of the disclosure. The present disclosure also provides a method for treating or ameliorating cancer, a viral infectious disease (viral infection), or an immune system disorder comprising administering to a subject in need thereof a therapeutically effective amount of a polynucleotide of the disclosure, i.e., a polynucleotide comprising a nucleic acid sequence encoding the novel vector/vector system of the disclosure. The present disclosure also provides a method for treating or ameliorating cancer, a viral infectious disease (viral infection), or an immune system disorder comprising administering to a subject in need thereof a therapeutically effective amount of an immune cell or cancer cell of the disclosure, i.e., an immune cell or cancer cell transduced or transfected with the novel vector/vector system or a virus particle disclosed herein. In various embodiments, the method of treating or ameliorating cancer is performed as ex vivo therapy comprising obtaining cancer cells from a patient, transducing or transfecting the autologous cancer cells with a vector system or a virus particle disclosed herein, and administering the autologous cancer cells transduced or transfected with the novel vector/vector system or a virus particle disclosed herein to the patient. The present disclosure also provides a method for treating or ameliorating cancer, a viral infectious disease (viral infection), or an immune system disorder comprising administering to a subject in need thereof a therapeutically effective amount of a medicament or composition of the disclosure described above.

As used herein, the term "therapeutically effective amount" refers to an amount of an active agent, composition or medicament disclosed herein, with which the harmful effects of a disease or disorder (e.g., cancer or an infectious disease) are, at a minimum, ameliorated.

In preferred embodiments, the cancer is any one of breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, mesothelioma, osteogenic sarcoma, primary macro globulinemia, and retinoblastoma.

In other preferred embodiments, the cancer is any one of melanoma, cancer metastasis, adenocarcinoma, thyoma, lymphoma, sarcoma, lung cancer, colon cancer, Hodgkins lymphoma, uterine cancer, breast cancer, prostate cancer, ovarian cancer, cervical cancer, kidney cancer, and pancreatic cancer. In particularly preferred embodiments, the cancer is an urogenital cancer, preferably bladder cancer. In other particularly preferred embodiments, the cancer is liver cancer. In still other particularly preferred embodiments, the cancer is skin cancer. The means and methods provided by the present disclosure are also particularly useful in methods for treating or preventing cancer metastasis.

In various embodiments, the cancer comprises one or more tumors that are accessible to allow for direct injection either into or around the tumor of an active agent (e.g., a vector system or virus particle), composition or medicament of the present disclosure. In particularly preferred embodiments, the cancer comprises a solid tumor or is a solid tumor. In certain embodiments, the solid tumor is a carcinoma, a sarcoma or a lymphoma. In this regard, while lymphomas are generally considered liquid tumors, accessible "solid" tumors may form in the lymph node and thus may be treated according to the methods and uses disclosed herein.

In various embodiments, the infectious disease is an infectious disease caused by a pathogenic bacterium. In other embodiments, the infectious disease is an infectious disease caused by a virus. In still other embodiments, the infectious disease is an infectious disease caused by a pathogenic parasite, protozoa or fungi.

Viral diseases that can be treated, protected against, and/or managed according to the present disclosure include, but are not limited to, those caused by hepatitis type A, hepatitis type B, hepatitis type C, influenza (e.g., influenza A or influenza B), varicella, adenovirus, herpes simplex type I (HSV-I), herpes simplex type II (HSV-II), rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), Ebola, Zika, and agents of viral diseases such as viral meningitis, encephalitis, dengue or small pox.

Bacterial diseases caused by bacteria that can be treated, protected against and/or managed in accordance with the present disclosure include, but are not limited to, Lyme disease, anthrax, tetanus, cholera, plague, diptheria, chlamydia, and pertussis.

Protozoan diseases caused by protozoa that can be treated, protected against, and/or managed in accordance with the present disclosure include, but are not limited to, leishmania and malaria. Parasitic diseases caused by parasites that can be treated, protected against, and/or managed in accordance with the present disclosure include, but are not limited to, chlamydia and rickettsia.

In the present disclosure, an immune system disorder is characterized by a downregulation of the immune system, in particular a downregulation of the immune response. The novel vector/vector system of the present disclosure enables control of such immune system disorders by converting an inactive into an active immune microenvironment and thereby treating an immune system disorder.

Likewise, in the present disclosure, cancer may be characterized by a downregulation of the immune system, in particular a downregulation of the immune response. Thus, the novel vector/vector system of the present disclosure enables control or treatment of cancer by converting an inactive into an active tumor microenvironment and thereby treating or controlling cancer.

Also, in the present disclosure, an infectious disease may be characterized by a downregulation of the immune system, in particular a downregulation of the immune response. Thus, the novel vector/vector system of the present disclosure enables control or treatment of infectious diseases by converting an inactive into an active immune microenvironment and thereby treating or controlling infectious diseases.

In various embodiments of the present disclosure, the vector system is present in a concentration of not more than $1 \times 10^{11}$ ivp, preferably not more than $1 \times 10^{10}$ ivp, more preferably not more than $1 \times 10^9$ ivp, even more preferably not more than $1 \times 10^7$ or $1 \times 10^6$ ivp per dose unit. This applies in particular to, but is not limited to, the medical treatments disclosed herein. Furthermore, in various embodiments of the present disclosure the virus particle is present in a concentration of not more than $1 \times 10^{11}$ ivp, preferably not more than $1 \times 10^{10}$ ivp, more preferably not more than $1 \times 10^9$ ivp, even more preferably not more than $1 \times 10^7$ or $1 \times 10^6$ ivp per dose unit. This applies in particular to, but is not limited to, the medical treatments disclosed herein.

In various embodiments, $5 \times 10^6$ ivp (infectious viral particles) of the novel vector/vector system or virus particle of the present disclosure is administered to a patient in need thereof. In various other embodiments, $5 \times 10^7$ ivp of the novel vector/vector system or virus particle of the present disclosure is administered to a patient in need thereof. In various other embodiments, $5 \times 10^8$ ivp of the novel vector/vector system or virus particle of the present disclosure is administered to a patient in need thereof.

In the present disclosure, the terms "medicament" or "pharmaceutical composition" may be used interchangeably. The medicament or pharmaceutical composition may be in any form, such as solid, semisolid or liquid form, suitable for administration. A formulation can be any one of, but not limited to, a solution, emulsion or suspension. Means and methods for formulating the present pharmaceutical preparations are known to persons skilled in the art, and may be manufactured in a manner, which is in itself known. The medicament (or pharmaceutical composition) may be administered in combination with a pharmaceutically acceptable carrier, excipient or diluent. Pharmaceutically acceptable carriers are well known in the art and include, but are not limited to, saline, buffered saline, dextrose, water, glycerol, amino acids, sterile isotonic aqueous buffer, and combinations thereof.

The active agents (e.g., the novel vector/vector system or viral particles), compositions and medicaments of the present disclosure may be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms. Formulations for parenteral and nonparenteral drug delivery are known in the art and are set forth in Remington's Pharmaceutical Sciences, $19^{th}$ Edition, Mack Publishing (1995), which is hereby incorporated by reference in its entirety.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

Subjects to be treated in accordance with the present disclosure are subjects that are at risk of developing, or have developed, cancer, an infectious disease, or an immune system disorder. Such subjects include human and non-human animals, preferably mammals or avian species. Exemplary mammalian subjects include, without limitation, humans, non-human primates, dogs, cats, rodents, cattle, horses, sheep, and pigs. Exemplary avian subjects include, without limitation, chicken, quail, turkey, duck or goose.

An effective amount of a therapeutic or preventive active agent, composition or medicament of the disclosure is determined based on the intended goal, for example stimulation of an immune response against a tumor or an infectious disease. Those of skill in the art are well aware of how to apply gene delivery in vivo and ex vivo. For viral vectors, one generally will prepare a viral vector stock. Depending on the kind of virus and the titer attainable, one will deliver at least about, at most about, or about $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ infectious viral particles, or any value or range there between, to a subject. In other aspects, the viral vector(s) according to the present disclosure may be administered in a single administration or multiple administrations. The viral vector(s) may be administered at dosage of $1 \times 10^5$ infectious viral particles (ivp), $5 \times 105$ ivp, at least $1 \times 10^6$ ivp, $5 \times 10^6$ or about $5 \times 106$ ivp, $1 \times 10^7$, at least $1 \times 107$ ivp, $1 \times 10^8$ or about $1 \times 108$ ivp, at least $1 \times 108$ ivp, about or at least $5 \times 10^8$ ivp, $1 \times 10^9$ or at least $1 \times 10^9$ ivp, $5 \times 10^9$ or at least $5 \times 10^9$ ivp, $1 \times 10^{10}$ ivp or at least $1 \times 1010$ ivp, $5 \times 10^{10}$ or at least $5 \times 10^{10}$ ivp, $1 \times 10^{11}$ or at least $1 \times 10^{11}$, $1 \times 10^{12}$ or at least $1 \times 10^{12}$, $1 \times 10^{13}$ or at least $1 \times 10^{13}$ ivp. For example, the viral vector(s) may be administered at a dosage of between about $10^7$-$10^{13}$ ivp, between about $10^8$-$10^{13}$ ivp, between about $10^8$-$10^{12}$ ivp, or between about $10^9$-$10^{12}$ ivp.

A therapeutic effect may be achieved with only one administration of an active agent (e.g., a vector system or virus particle), composition or medicament of the present disclosure. On the other hand, the treatment may contain several administrations.

The effective dose of vectors depends on at least the subject in need of the treatment, type of the disease and stage of the disease. The dose may vary for example from about $1 \times 10^8$ ivp (infectious viral particles) to about $1 \times 10^{14}$ ivp, specifically from about $1 \times 10^9$ ivp to about $1 \times 10^{13}$ ivp, and more specifically from about $5 \times 10^9$ ivp to about $1 \times 10^{12}$ ivp.

Administration of the active agent (e.g., a vector system or virus particle), composition or medicament of the present disclosure can be conducted through any suitable method known to a person skilled in the art. In one embodiment of the disclosure, the administration is conducted through an intratumoral, intra-arterial, intravenous, intrapleural, intravesicular, intracavitary or peritoneal injection, or an oral administration. In another embodiment of the disclosure, the administration is conducted intramuscularly, intradermally, subcutaneously, parenterally, intranasally, intratracheally, percutaneously, intraspinally, ocularly, or intracranially. It is also possible to combine different routes of administration. In a preferred embodiment, the administration is conducted through an intratumoral administration, i.e., administration of the active agent (e.g., a vector system or virus particle), composition or medicament of the present disclosure into the tumor.

The active agent (e.g., a vector system or virus particle), composition or medicament of the present disclosure may also be used together (simultaneously, sequentially, or concomitantly) with other therapeutic agents or therapeutic methods or a combination of treatments. For example, the therapeutic methods or uses of the disclosure may further comprise radiotherapy, chemotherapy, administration of other drugs, e.g. antibodies addressing tumor growth mechanisms, immune cell checkpoint targets, cancer vaccines, or any clinical operations.

As described herein, methods and uses are provided for immunostimulation (i.e., inducing, controlling and/or activating and/or stimulating immune response mechanisms in the context of the treatment of cancer, an infectious disease or an immune system disorder, in particular for attracting or recruiting cells induced, activated and/or stimulated by the immunostimulation to a site of interest (e.g., to a tumor, or a mucosal site of infection). Cells of the immune system that are involved in an immune response are referred to, generally, as immune cells and include lymphocytes and non-lymphoid cells such as accessory cells. Lymphocytes are cells that specifically recognize and respond to foreign antigens. Major classes of lymphocytes include B lymphocytes (B cells), T lymphocytes (T cells), and natural killer (NK) cells, which are large granular lymphocytes. B cells are capable of producing antibodies. T lymphocytes are further subdivided and include helper T cells (CD4+ T cells) and cytolytic or cytotoxic T cells (CD8+ T cells). Helper cells secrete cytokines that promote proliferation and differentiation of the T cells and other cells, including B cells and macrophages, and recruit and activate inflammatory leukocytes. Another subgroup of T cells, called regulatory T cells or suppressor T cells, actively suppress activation of the immune system and prevent pathological self-reactivity, that is, autoimmune disease.

The immunostimulation methods described herein is considered to induce a cell-mediated immune response involving various types of T cells. In a cell mediated response, the various types of T lymphocytes act to eliminate an antigen by a number of mechanisms. For example, helper T cells that are capable of recognizing specific antigens may respond by releasing soluble mediators such as cytokines to recruit additional cells of the immune system to participate in an immune response. Also, cytotoxic T cells are capable of specifically recognizing an antigen and may respond by binding to and destroying or damaging an antigen-bearing cell or particle.

An immune response in a host or subject may be determined by any number of well-known immunological methods with which those having ordinary skill in the art will be familiar. As described herein, methods and techniques for determining the presence and level of an immune response include, for example, fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence, immunoassays, (such as enzyme-linked immunosorbant assays (ELISA), radioimmunoassay, immunoblotting, immunohistochemistry, and the like), surface plasmon resonance, cell-based assays such as those that use reporter genes, and functional assays (e.g., assays that measure immune function and immunoresponsiveness).

Such assays include, but need not be limited to, in vivo or in vitro determination of the presence and level of soluble antibodies, soluble mediators such as cytokines (e.g., IFN-γ, IL-2, IL-4, IL-10, IL-12, IL-6, IL-23, TNF-α, and TGF-β), lymphokines, chemokines, hormones, growth factors, and the like, as well as other soluble small peptide, carbohydrate, nucleotide and/or lipid mediators. Levels of cytokines may be determined according to methods described and practiced in the art, including, for example, ELISA, ELISPOT, intracellular cytokine staining, and flow cytometry and combinations thereof (e.g., intracellular cytokine staining and flow cytometry).

Immunoassays also include determining cellular activation state changes by analyzing altered functional or structural properties of cells of the immune system, for example, cell proliferation, altered motility, induction of specialized activities such as specific gene expression or cytolytic behavior; cell maturation, such as maturation of dendritic cells in response to a stimulus; alteration in relationship between a Th1 response and a Th2 response; cellular differentiation by cells of the immune system, including altered surface antigen expression profiles or the onset of apoptosis (programmed cell death). Other methods are also available for measuring cell surface markers to identify various populations of immune cells, such as, but not limited to, antigen-specific CD4+ and/or CD8+ T cells, effector memory T cells (Tem), central memory T cells (Tcm) and/or tissue-resident memory T cells (Trm). Procedures for performing these and similar assays are described in the literature. Cytotoxicity assays for determining CTL activity (or CD8+ T cell activity) may be performed using any one of several techniques and methods routinely practiced in the art.

In particular embodiments, a 2-50 fold increase in locally infiltrating antigen-specific T cells is observed following the methods and uses disclosed herein. In certain embodiments, a 2-40 fold increase, a 2-30 fold increase, a 2-20 fold increase, a 2-10 fold increase, 3-8 fold increase, a 4-7 fold increase, or a 5-6 fold increase in locally infiltrating (e.g., tumor-infiltrating) antigen-specific T cells is observed. Generally, the increase in locally infiltrating antigen-specific T cells is as compared to the number of locally infiltrating antigen-specific T cells present in the absence of administration or as compared to an appropriate control administration. The methods and uses disclosed herein are considered to provide an increase in a statistically, biologically, and/or clinically significant manner of the locally infiltrating antigen-specific T cells as compared to an appropriate control in the absence of administering the active agent, composition or medicament of the disclosure.

A biological sample may be obtained from the subject for determining the presence and level of an immune response in the subject who has received a treatment with an active agent (e.g., a vector system or virus particle), composition or medicament of the disclosure according to the methods disclosed herein. A "biological sample" as used herein may be a blood sample (from which serum or plasma may be prepared), apheresis sample, biopsy specimen, tumor biopsy specimen, body fluids (e.g., lung lavage, ascites, mucosal washings, synovial fluid), bone marrow, lymph nodes, tissue explant, organ culture, or any other tissue or cell preparation from the subject or a biological source.

With respect to all immunoassays and methods described herein for determining an immune response, a person skilled in the art will also readily appreciate and understand which controls are appropriately included when practicing these methods. Concentrations of reaction components, buffers, temperature, and time period sufficient to permit interaction of the reaction components can be determined and/or adjusted according to methods with which a person skilled in the art is familiar.

Another aspect of the present disclosure provides a method of increasing T-cells in the tumor microenvironment comprising administering to a subject having a tumor an active agent (e.g., a vector system or virus particle), composition or medicament of the disclosure according to the methods disclosed herein, thereby inducing an immune response against the tumor.

As understood by a person skilled in the medical art, the terms "treat" and "treatment" refer to medical management of a disease, disorder, or condition of a subject (i.e., patient). In general, an appropriate dose and treatment regimen provide the active agent (e.g., a vector system or virus particle), composition or medicament of the disclosure in an amount sufficient to provide therapeutic and/or prophylactic benefit. Therapeutic and/or prophylactic benefit includes, for example, an improved clinical outcome, both therapeutic treatment and prophylactic or preventative measures, wherein the object is to prevent or slow or retard (lessen) an undesired physiological change or disorder, or to prevent or slow or retard (lessen) the expansion or severity of such disease or disorder. Beneficial or desired clinical results from treating a subject include, but are not limited to, abatement, lessening, or alleviation of symptoms that result from or are associated with the disease or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. "Treatment" can also mean prolonging survival when compared to expected survival if a subject were not receiving treatment. Subjects in need of treatment include those who already have the disease or disorder as well as subjects prone to have or at risk of developing the disease or disorder).

Nucleic acid molecules, including vector systems according to the present disclosure, may be delivered into a cell according to any one of several methods described in the art. Such delivery methods known to persons having skill in the art, include, but are not restricted to, encapsulation in liposomes, by iontophoresis, or by incorporation into other vehicles, such as biodegradable polymers; hydrogels; cyclodextrins; poly(lactic-co-glycolic)acid (PLGA) and PLCA microspheres; biodegradable nanocapsules; and bioadhesive microspheres, or by proteinaceous vectors.

The present disclosure provides a combination of proteins comprising 4-1BB ligand (4-1BBL), IL-2 and single chain IL-12 (scIL-12), wherein the amount of 4-1BBL is higher than the amount of scIL-12 and IL-2.

In various embodiments, the 4-1BB ligand comprises an amino acid sequence having at least 70% homology or identity to the amino acid sequence of SEQ ID NO: 2 (FIG. 13), wherein the 4-1BB ligand is capable of specifically binding T cells, preferably activated CD4+ T helper cells and CD8+ T cells. Preferably, the 4-1BB ligand comprises an amino acid sequence having at least 80% homology or identity to the amino acid sequence of SEQ ID NO: 2 (FIG. 13), wherein the 4-1BB ligand is capable of specifically binding T cells, preferably CD8+ T cells. More preferably, the 4-1BB ligand comprises an amino acid sequence having at least 90% homology or identity to the amino acid sequence of SEQ ID NO: 2 (FIG. 13), wherein the 4-1BB ligand is capable of specifically binding T cells, preferably activated CD4+ T helper cells and CD8+ T cells. Even more preferably, the 4-1BB ligand comprises an amino acid sequence having at least 95% homology or identity to the amino acid sequence of SEQ ID NO: 2 (FIG. 13), wherein the 4-1BB ligand is capable of specifically binding T cells, preferably activated CD4+ T helper cells and CD8+ T cells. In certain embodiments, variants of 4-1BBL as described above exhibit the same binding specificity for T cells, preferably for activated CD4+ T helper cells and CD8+ T cells, as the native 4-1BBL having the amino acid sequence of SEQ ID NO: 2 (FIG. 13).

In various embodiments of the disclosure, the IL-2 protein shows at least 70% homology or sequence identity to the amino acid sequence of SEQ ID NO: 4 (FIG. 14), wherein the IL-2 protein has immune stimulating activity, preferably T helper cell and CD8+ T cell stimulating activity. Preferably, the IL-2 protein shows at least 80% homology or sequence identity to the amino acid sequence of SEQ ID NO: 4 (FIG. 14), wherein the IL-2 protein has immune stimulating activity, preferably T helper cell and CD8+ T cell stimulating activity. More preferably, the IL-2 protein shows at least 90% homology or sequence identity to the amino acid sequence of SEQ ID NO: 4 (FIG. 14), wherein the IL-2 protein has immune stimulating activity, preferably T helper cell and CD8+ T cell stimulating activity. Even more preferably, the IL-2 protein shows at least 95% homology or sequence identity to the amino acid sequence of SEQ ID NO: 4 (FIG. 14), wherein the IL-2 protein has immune stimulating activity, preferably T helper cell and CD8+ T cell stimulating activity. In certain embodiments, variants of IL-2 as described above exhibit the same immune stimulating activity, preferably T helper cell and CD8+ T cell stimulating activity, as the native IL-2 having the amino acid sequence of SEQ ID NO: 4 (FIG. 14).

In various embodiments of the disclosure, the scIL-12 protein comprises an amino acid sequence having at least 70% homology or sequence identity to the amino acid sequence of SEQ ID NO: 6 (FIG. 15), wherein the scIL-12 protein has immune stimulating activity, preferably monocyte, T helper cell and CD8+ T cell stimulating activity. Preferably, the scIL-12 protein comprises an amino acid sequence having at least 80% homology or sequence identity to the amino acid sequence of SEQ ID NO: 6 (FIG. 15), wherein the scIL-12 protein has immune stimulating activity, preferably monocyte, T helper cell and CD8+ T cell stimulating activity. More preferably, the scIL-12 protein comprises an amino acid sequence having at least 90% homology or sequence identity to the amino acid sequence of SEQ ID NO: 6 (FIG. 15), wherein the scIL-12 protein has immune stimulating activity, preferably monocyte, T helper cell and CD8+ T cell stimulating activity. Even more preferably, the scIL-12 protein comprises an amino acid sequence having at least 95% homology or sequence identity to the amino acid sequence of SEQ ID NO: 6 (FIG. 15), wherein the scIL-12 protein has immune stimulating activity, preferably monocyte, T helper cell and CD8+ T cell stimulating activity. In certain embodiments, variants of scIL-2 as described above exhibit the same immune stimulating activity, preferably monocyte, T helper cell and CD8+

T cell stimulating activity, as the native scIL-2 having the amino acid sequence of SEQ ID NO: 6 (FIG. 15).

As disclosed herein, a protein is considered a scIL-12 protein if it comprises an amino acid sequence comprising the two subunits p35 and p40 of the native IL-12 protein as a fusion protein. The sequences of SEQ ID NOs: 8 and 10 show the amino acid sequence of the 40 kDa and 35 kDa subunits of human IL-12. In certain embodiments, variants of scIL-12 as described above exhibit the same immune stimulating activity as the native scIL-12 encoded by the amino acid sequences of SEQ ID NOs: 8 and 10. Preferably, the linker of the scIL-12 of the present disclosure is a peptide or polypeptide linker. The present disclosure encompasses variants of the scIL-12 as described herein, in which in particular the linker sequence shown in boldface in FIG. 15 (SEQ ID NOs: 5 and 6) is modified, specifically with respect to the length of the linker sequence. The length of the amino acid sequence of the linker can be selected empirically or with guidance from structural information or by using a combination of the two approaches. Those skilled in the art will recognize that there are many such sequences that vary in length or composition that can serve as linkers with the primary consideration being that they be neither excessively long nor short.

The novel vector/vector system or virus particles provided by the present disclosure can be packaged as kits. Kits can optionally include one or more components such as instructions for use and administration, devices (e.g., for administering the composition or compositions to a subject), and additional reagents, and components, such as tubes, containers, e.g. vials, and syringes for practice of the methods and uses. Kits comprising a polynucleotide comprising a nucleic acid sequence encoding a vector system of the disclosure are also contemplated herein. Kits comprising a cancer cell transduced or transfected with a vector system or virus particle of the disclosure are also contemplated herein. Kits comprising an active agent, a composition, or a medicament of the disclosure are also contemplated herein.

Kits comprising the novel viral vector/vector system of the disclosure and optionally a polynucleotide sequence encoding a maturation factor are also contemplated herein.

In light of the present disclosure, herein encompassed are, without being limited thereto, the following items, which are to be considered in the context of the aspects and embodiments described elsewhere herein:

1. Vector comprising nucleic acid sequences of genes encoding 4-1BB ligand (4-1BBL), single chain IL-12 (scIL-12) and IL-2, wherein the said genes are organized in 5' to 3' orientation in a sequential order 1, 2, 3, with the proviso that the gene encoding scIL-12 is not at position 1.

2. The vector of item 1, wherein the vector is any one of an adenoviral vector, an adeno-associated virus vector, a lentiviral vector, a retroviral vector, a herpes simplex virus vector, a pox virus vector, a RNA vector, a plasmid vector, a nanoparticle vector, and naked DNA.

3. The vector of item 2, wherein the RNA vector comprises inserted modified ribonucleotides.

4. The vector of any one of items 1-3, wherein the nucleic acid sequence of the gene encoding 4-1BBL is human cDNA, the nucleic acid sequence of the gene encoding scIL-12 is human cDNA, and/or the nucleic acid sequence of the gene encoding IL-2 is human cDNA.

5. The vector of any one of items 1-4, wherein the nucleic acid sequence of the gene encoding 4-1BBL shows at least 70% homology or sequence identity to the nucleic acid sequence of SEQ ID NO: 1 (FIG. 13), wherein the variant nucleic acid sequence encodes a 4-1BBL protein capable of specifically binding T cells, preferably activated T cells.

6. The vector of any one of items 1-4, wherein the nucleic acid sequence of the gene encoding IL-2 shows at least 70% homology or sequence identity to the nucleic acid sequence of SEQ ID NO: 3 (FIG. 14), wherein the variant nucleic acid sequence encodes a IL-2 protein having immune stimulating activity.

7. The vector of any one of items 1-4, wherein the nucleic acid sequence of the gene encoding scIL-12 shows at least 70% homology or sequence identity to the nucleic acid sequence of SEQ ID NO: 5 (FIG. 15), wherein the variant nucleic acid sequence encodes an scIL-12 protein having immune stimulating activity.

8. The vector of any one of items 1-7, wherein the nucleic acid sequences of the genes encoding scIL-12 and IL-2 are located downstream of the nucleic acid sequence of the gene encoding 4-1BBL.

9. The vector of item 8, wherein the nucleic acid sequence of the gene encoding IL-2 is located downstream of the nucleic acid sequence of the gene encoding 4-1BBL, and the nucleic acid sequence of the gene encoding scIL-12 is located downstream of the nucleic acid sequence encoding IL-2.

10. The vector of item 8 or 9, wherein a promoter is located upstream of the nucleic acid sequence of the gene encoding 4-1BBL, but not upstream of the nucleic acid sequences of the genes encoding scIL-12 and/or IL-2.

11. The vector of any one of items 8-10, wherein the nucleic acid sequences of the genes encoding 4-1BBL, scIL-12 and IL-2 are linked by internal ribosomal entry sites (IRES).

12. Virus particle comprising the vector of any one of items 1-11.

13. A polynucleotide comprising a nucleic acid sequence encoding the vector of any one of items 1-11.

14. A cancer cell or an immune cell, transduced or transfected with the vector of any one of items 1-11 or the virus particle of item 12.

15. A composition comprising the vector of any one of items 1-11, the virus particle of item 12, the polynucleotide of item 13, or the cancer cell or immune cell of item 14.

16. A medicament comprising the vector of any one of items 1-11, the virus particle of item 12, the polynucleotide of item 13, or the cancer cell or immune cell of item 14.

17. The vector of any one of items 1-11, the virus particle of item 12, the polynucleotide of item 13, the cancer cell or immune cell of item 14, the composition of item 15, or the medicament of item 16 for use in a method of treating cancer, a viral infection and/or an immune system disorder.

18. The vector for use according to item 17, the virus particle for use according to item 17, the polynucleotide for use according to item 17, the cancer cell or immune cell for use according to item 17, the composition for use according to item 17, or the medicament for use according to item 17, wherein the cancer is any one of breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, mesothelioma, osteogenic sarcoma, primary macro globulinemia, and retinoblastoma.

19. The vector of any one of items 1-11, the virus particle of item 12, the composition of item 13, or the medicament of item 14 for use in a method of preventing or treating cancer metastasis.

20. The vector for use according to any one of items 17-19, characterized in that the vector system is present in a concentration of not more than $1\times10^{11}$ ivp (infectious viral particles), preferably not more than $1\times10^{10}$ ivp, more preferably not more than $1\times10^{9}$ ivp, even more preferably not more than $1\times10^{7}$ ivp or $1\times10^{6}$ ivp per dose unit.

21. The virus particle for use according to any one of items 17-19, characterized in that the virus particle is present in a concentration of not more than $1\times10^{11}$ ivp, preferably not more than $1\times10^{10}$ ivp, more preferably not more than $1\times10^{9}$ ivp, even more preferably not more than $1\times10^{7}$ ivp or $1\times10^{6}$ ivp per dose unit.

22. A combination of proteins comprising 4-1BB ligand (4-1BBL), IL-2 and single chain IL-12 (scIL-12), wherein the amount of 4-1BBL is higher than the amount of scIL-12 and IL-2

It is to be acknowledged that the present disclosure is not limited to the particular methodology, protocols, cell lines, genera, and reagents described herein, as such may vary. It is also to be acknowledged that the terminology used herein is for the purpose of describing particular embodiments only, and is not intended to be limiting the scope of the present disclosure.

The following examples are offered by way of illustration and not by way of limitation.

Other embodiments and uses will be apparent to one skilled in the art in light of the present disclosures. The following examples are provided merely as illustrative of various embodiments and shall not be construed to limit the present disclosure in any way.

EXAMPLES

Example 1: Transgene Expression of IL-12, IL-2 and 4-1BBL and IFN-γ Response of Murine and Human Im01

Im01 is an adenoviral vector comprising an expression construct comprising the human genes for single chain IL-12, 4-1BBL, and IL-2 in the order as shown in the following scheme:

-CMV>-|scIL-12|-(IRES)-|4-1BBL|-(IRES)-|IL-2|-

The construction of vector Im01 is described in WO 2004/035799 with the above scheme depicted in FIG. 1 of WO 2004/035799. The vector name in WO 2004/036799 is "Ad-3". In the present disclosure, the internal vector code for the earlier vector is Im01.

Human A549 cells and murine Hepa1-6 cells were transduced one hour with Im01 carrying the three human or mouse genes, respectively, at the indicated multiplicity of infection (MOI, numbers given in [brackets]). Human peripheral blood mononuclear cells (PBMCs) or mouse lymphocytes were added 4 hours after transduction and supernatants were collected for cytokine assays after 34 hours of co-culture. Cytokine levels were detected by ELISA (eBioscience). Tumor cells were detached and assayed by flow-cytometry for 4-1BBL expression. As a result, even though the murine and human vector architecture is identical, the expression level of the transgenes clearly varies between murine and human species in that the human Im01 shows up to 15-fold higher IL-12 expression than the murine Im01. In the clinical setting such increased IL-12 levels carry the risk for toxicity and for limited therapeutic applicability.

Example 2: Vector Design and Study Overview

Im02

A vector according to the present disclosure has been designed and produced for an ex vivo therapy simulation study. The vector is based on an adenoviral vector and has been named Im02 (internal vector code "Im02"). Im02 comprises an expression construct comprising the human genes for 4-1BBL, IL-2 and single chain IL-12 (scIL-12) in the order as shown in the following scheme:

-CMV>-|4-1BBL|-(IRES)-|IL-2|-(IRES)-|scIL-12|-

FIG. 2 shows a schematic gene map of the shuttle plasmid pE1.1 Im02. The expression cassette for Im02 is illustrated as a precursor transfer plasmid based on plasmid pE1.1, suitable for sub-cloning into a plasmid carrying, e.g., adenoviral vector DNA. More specifically, the expression cassette contained in the adenoviral vector Im02 is the expression cassette as shown in FIG. 18 comprising the nucleotide sequence of SEQ ID NO: 12. The vector of the present disclosure has been identified to induce immune defense mechanisms against tumor cells in bladder cancer by multivalent modification of the intratumoral immune microenvironment.

Patient Cohort Overview

Ex vivo cultures of human tumor biopsy samples were chosen as study model for the novel vector system. Samples were provided by the Clinic of Urology, Asklepios hospital, Hamburg-Barmbek. In total 244 tumor samples and 270 normal bladder tissue control biopsies from 43 patients have been analyzed. From eight patients samples were collected during transurethral resection (TUR), the major part of the study-included samples was from cystectomy. In this study, tumor and bladder tissues were analyzed across a wide range of disease stages, varying from early to late stage. Samples from 16 females and 27 males have been analyzed. Pretreatments in this patient cohort were serial TUR, chemotherapy, or anti-androgen therapy, due to concomitant diagnosis of prostate carcinoma.

Example 3: Transgene Expression of 4-1BBL, IL-2 and scIL-12, and IFN-γ Response of Im02 and the Earlier Vector Im01

Transgene expression of 4-1BBL, IL-2 and IL-12, and IFN-γ response of Im02 (see Example 2) and the earlier vector Im01 (see Example 1) were compared.

Human A549-cells were transduced one hour with Im01 or Im02 at the MOI (multiplicity of infection, i.e., infectious viral particles per target cell) indicated in FIG. 3 (MOI numbers in brackets). Human peripheral blood mononuclear cells (PBMCs) were added 4 hours after transduction and supernatants were collected for cytokine assays after 34 hours of co-culture. Cytokine levels were detected by ELISA. Tumor cells were detached and cells positive for 4-1BBL were detected by flow cytometry. Indicated data points are the mean of four individual donors each with four replicates.

As shown in FIG. 3, the arrangement of the genes for 4-1BBL, IL-2 and scIL-12 in Im02 provides for an increased expression of 4-1BBL as compared to the arrangement of the same genes in Im01, concurrent with a decrease of IL-12, leading to an increase in IFN-γ response. In particular, the arrangement of the genes for 4-1BBL, IL-2 and scIL-12 in Im02 leads to a 1.7-fold increase of 4-1BBL expression, and a 1.5-fold increase of IL-2 expression in mean, as compared to the arrangement of genes in the earlier vector Im01. This is combined with a 2.6-fold decrease of the IL-12 expression level. With the arrangement of the genes in Im02, the molar ratio of IL-2/IL-12 was increased from 2.5% to 9.1% on average. Furthermore, higher IL-2 and 4-1BBL expression leads to a 1.4-fold higher IFN-γ induction detected at all dose ranges, MOI 2.5, 5, 10, and 50.

Im02 provides for an IFN-γ response, which is superior over that of Im01. As a result, Im02 shows an improved effect in immunostimulation as compared to the earlier vector Im01.

Example 4: Comparison of Single Vectors and Im02 and Im01 in a Tissue-Based Model Single-dose treatments using adenoviral vectors expressing scIL-12, IL-2 or 4-1BBL alone were examined as well as Im02 and Im01 (see Example 1 for further details of the latter one). To study the Im02 effects on the tumor microenvironment, a therapy simulation model based on undissociated tumor tissue samples was established. Tissue samples derived from transurethral resection or bladder cystectomy were used.

Bladder tumor ("T") and normal bladder ("B") tissues were transduced with $10^8$ ivp (infectious virus particles) of Im02 or Im01. Viability of tumor and bladder tissue samples was monitored in culture medium supernatants using an enzymatic LDH-release assay. Expression of transgenes and IFN-γ response was measured by ELISA in culture supernatant at day 6 after transduction. The results are shown in FIG. 4. Even at high expression levels of scIL-12 and IL-2 alone the IFN-γ response is close to background. This result suggests the cooperative action of the three genes in the tissue context of bladder and tumor. Furthermore, Im02 leads to an increase of IL-2 and IFN-γ response as compared to Im01. FIG. 4 shows an improved effect for Im02 in immunostimulation in the tumor microenvironment as compared to the earlier vector Im01.

Example 5: Comparison of Im02 and Im01 at Different Dose Levels

Im02 and Im01 (see Examples 2 and 3 for further details of these vectors) were compared at escalating doses for transgene expression and IFN-γ response in the tumor microenvironment. Tumor samples were derived from individual patients, and a matched pair of bladder tumor ("T") and normal bladder ("B") tissues was examined for the dose-levels $10^7$ and $10^8$ ivp (infectious virus particles). Expression was measured at day 6 by ELISA. The results are shown in FIG. 5. At different dose levels, Im02 provides for an IFN-γ response, which is superior over that of Im01. As a result, at different dose levels Im02 shows an improved effect in immunostimulation in the tumor microenvironment as compared to the earlier vector Im01.

Example 6: Gene Expression Profiling for Im02 and Im01

A transcriptome analysis has been performed to show the therapeutic gene expression profile for Im02. In particular, in order to obtain a comprehensive profile of leukocyte activation by Im02 and Im01, tumor cells of a co-culture experiment with tumor cells and PBMCs were transduced with Im02, Im01, and Ad0 (empty vector), and a mRNA gene activity analysis (Illumina Chip HT12 whole genome expression analysis) of the leukocytes was performed. To this end, peripheral leukocytes were added to the co-culture after transduction. Leukocytes on non-transduced tumor cells were used as control. After 4, 24, 32, 48, 72 and 96 hours, leukocytes were collected and the RNA was isolated and purified. After quality check, the RNA is reversely transcribed into complimentary DNA (cDNA), labeled according to the protocol of the bead chip and was loaded onto the bead chip HT12 and a scan was performed (Life & Brain, department of human genetics at the University of Bonn). The obtained data were transferred to the GenomeStudio Software (Illumina). Subsequently, the data were evaluated using the IPA® Software (Ingenuity). A core analysis was performed showing the differentially regulated processes. In order to gain an overview of the regulated processes, and to illustrate their significance and the involved number of molecules, an IPA® process analysis was performed. See Tables 1 and 2:

TABLE 1

Im02, the five most heavily regulated processes at 24 h

| Name | p-value | #Molecules |
|---|---|---|
| Molecular and Cellular Functions | | |
| Cell-to-Cell Signaling and Interaction | 1.28E−22-4.91E−03 | 103 |
| Cellular Function and Maintenance | 4.34E−22-4.52E−03 | 90 |
| Cell Death and Survival | 3.48E−17-3.98E−03 | 69 |
| Cellular Development | 1.46E−16-5.71E−03 | 101 |
| Cellular Growth and Proliferation | 1.46E−16-5.71E−03 | 89 |
| Physiological System Development and Function | | |
| Hematological System Development and Function | 1.28E−22-5.71E−03 | 162 |
| Immune Cell Trafficking | 1.28E−22-4.96E−03 | 108 |
| Tissue Morphology | 9.81E−17-5.59E−03 | 86 |
| Cell-mediated Immune Response | 6.66E−10-3.84E−03 | 61 |
| Tissue Development | 1.53E−08-4.91E−03 | 54 |

TABLE 2

Im01, the five most heavily regulated processes at 24 h

| Name | p-value | #Molecules |
|---|---|---|
| Molecular and Cellular Functions | | |
| Cell-to-Cell Signalling and Interaction | 8.05E−17-7.51E−03 | 61 |
| Cell Death and Survival | 1.27E−11-7.77E−03 | 42 |
| Cellular Function and Maintenance | 8.69E−11-7.16E−03 | 46 |
| Cellular Growth and Proliferation | 1.39E−09-7.16E−03 | 47 |
| Cellular Compromise | 3.44E−08-3.39E−03 | 25 |
| Physiological System Development and Function | | |
| Hematological System Development and Function | 8.05E−17-7.51E−03 | 83 |
| Immune Cell Trafficking | 8.05E−17-7.51E−03 | 64 |

TABLE 2-continued

Im01, the five most heavily regulated processes at 24 h

| Name | p-value | #Molecules |
|---|---|---|
| Tissue Development | 4.10E−07-6.95E−03 | 31 |
| Hematopoiesis | 1.04E−06-6.95E−03 | 35 |
| Tissue Morphology | 2.17E−06-6.95E−03 | 40 |

As a result, Im02 provides for an immunostimulation, which is characterized by a "cell-mediated immune response" involving 61 regulated genes (see Table 1, lower part) among the five most heavily regulated processes of physiological development and function (by virtue of significance and number of molecules involved). For Im01 (see Table 2, lower part), this function (i.e., "cell-mediated immune response") does not appear among the five most heavily regulated processes of physiological development and function because here only a total of 28 molecules are differentially regulated. The other systems mentioned in the table (like the hematological system, immune cell trafficking, tissue morphology, and general tissue development), suggest extensive changes caused by multivalent immune therapeutics. What becomes clear from the transcriptome analysis is that the therapeutic gene expression profile for Im02 is unique and superior, in particular superior over that of the earlier vector Im01.

The regulated processes have been allocated to specifically regulated (cell) functions using the IPA® software (Ingenuity Pathway Analysis, Qiagen). This permits more accurate information as regards the activation/inactivation of biological processes.

As a result (data not shown), the five most heavily induced functions are lymphoycyte activation, activation of mononuclear leukocytes, cytotoxicity of leukocytes, differentiation of mononuclear leukocytes, and activation of T lymphocytes (T cells).

Example 7: Gene Expression Analysis for Activation of Major Immune Cell Types

The activation of major immune cell types over a time course of 96 hours has been analyzed using the CELLMIX software, which allows analyzing gene expression data for the presence and state of activation of all major immune cell types. The heat plot in FIG. 6 illustrates the activation of all major blood immune cell subtypes except for B-cells (peripheral blood mononuclear cells, PBMCs) over a time course of 4 days (96 hours) in co-culture with human bladder RT-4 carcinoma cells. As shown in FIG. 6, the activation of T helper cells and cytotoxic T cells by Im02 is superior over the activation of the same immune cells by Im01.

Example 8: Ex Vivo Tissue Study Results

Tissue Profiling by Histology
Variation in tissue quality and cellular composition were monitored in tissue sections either after formalin fixation and paraffin embedding or after tissue freezing and fixation. Overall quality was evaluated after hematoxylin-eosin staining (HE).

As shown in FIG. 7, Im02 induced histological rearrangements (C), which were not seen with an Ad0 control vector (B), or single gene vectors (data not shown). Im02 induced morphological alterations observed in tumor tissues (FIG. 7, panel C) include the number and distribution of immune cell infiltrates with respect to tissues treated with either control Ad0/AdNull (panel B) or single-gene vectors (data not shown).

Furthermore, FIG. 8 shows that Im02 induces apparent histological rearrangements in the distribution and frequency of leukocyte infiltrates. The arrow in the lower panel of FIG. 8 indicates a tumor region with signs of cell death. These morphological changes provide histological evidence for an Im02-induced immune response.

Identification of Target Cell Types
Transmission electron microscopy (TEM) on tissues transduced with Im02 was performed to identify, inter alia, the target cell type of adenoviral particle uptake, the route of uptake, judged by the presence and morphology of vesicle membranes, and the abundance of particles per cell.

Tumor tissue from a cystectomy was dissected and transduced by submerging the sample with 500 µl culture medium containing $10^8$ ivp Im02 for 1 hour at 37° C., uptake was stopped by medium replacement with ice-cold fixation solution containing 2% glutaraldehyde. Tissue samples were then processed by standard procedures and images taken by transmission electron microscopy, supplied by Vironova SA, Stockholm, Sweden.

In positive stain transmission electron microscopy, adenoviral particles were identified by their size of about 80 nm and by particle geometry. The results are shown in FIG. 9. After one hour of transduction, Im02 adenoviral particles are detectable in a variety of cell types as identified by ultrastructural morphology analyses. Presence and morphology of vesicle structures around adenoviral particles indicate the uptake mechanism.

By their individual morphology, different cell types were found as target cells in bladder carcinoma samples, including tumor cells (not shown), connective tissue cells (fibroblast, Panel 4) of the tumor stroma and immune cells. Adenoviral particles were detected in cells of lymphocyte (Panel 3) and monocyte morphology (Panel 2). In bladder carcinoma, monocyte morphology indicates presence of Langerhans cells, macrophages or dendritic cells.

Importantly, this finding is of particular value for the mode-of-action, since all these identified target immune cells are described to undergo activation and differentiation into effector cell types after transduction with cytokines, while 4-1BBL-expression was shown to support activating processes when expressed in antigen-presenting cells and on lymphocytes, by reverse signal transduction (Ju et al., 2009, *International Immunology*, 21(10), 1135-1144). Route of uptake and abundance: Adenoviral particles were found in the cytoplasm of target cells in different positions and with different surroundings. The classical uptake is mediated after binding to the Coxsackie and Adenovirus receptor, followed by shuttling in endocytotic vesicles.

This pathway is suggested to be active in Panel 6A, where a particle is imaged in the process of vesicle formation. In Panel 6B, an adenoviral particle is located in a large vesicle also containing other non-defined structures, suggesting a pinocytotic way of uptake. In Panel 3A, an adenoviral particle was captured in a circular membrane structure suggesting advanced endocytotic uptake.

Exposure of tissue samples to Im02 for only one hour was chosen in accordance with a future intravesicular instillation protocol. In our tissue model particles reach areas at a depth of several cell layers. Regularly groups of up to 30 adenoviral particles per cell were identified (Panel 5A).

Example 9: Comparison of Differential Expression in Normal Bladder and Bladder Tumor Samples Normal bladder and tumor tissues were transduced with $10^8$ ivp Im02. Cultures were continued until day 6. Differential expression was determined in comparison to samples treated with Ad0 (empty adenoviral vector) as a control. FIG. 10 shows the results for a pool of 9 bladder and 10 tumor tissue samples. The overall stimulation (i.e., induction of immune response processes) is higher in tumor tissues than in normal bladder tissues (see FIG. 10). This effect points on differences in the microenvironment between normal and tumor tissues, e.g., differences in immune cell infiltrate numbers or the level of suppression in the vicinity to tumor cells.

Example 10: Examination of Transfectants for Adenoviral Uptake

Adenoviral uptake into intact bladder tissue can be improved by the addition of transfectant-like polycationic compounds. For ex vivo tissue sample perfusion of Im02, protamine sulfate (10 μg/ml) was identified to enable adenoviral product uptake independent of Coxsackie-Adenovirus-receptor (CAR) expression in a candidate compound screen in a set of cell lines (see FIG. 11). The human bladder carcinoma line RT-4 reportedly expresses CAR, whereas the mouse colon carcinoma line CT-26 does not. The adenoviral product was formulated in the buffers as indicated in the legend of FIG. 11. Human bladder cancer cell line RT-4 and the CAR-negative murine colon cancer cell line CT-26 were transduced with an Ad-GFP (adenoviral vector carrying GFP) at different multiplicities per target cell (MOI: multiplicity of infection). Results are illustrated as percentage of GFP-positive cells 48 hours after transduction, measured by flow cytometry. As a result, in both cell lines protamine sulfate at 10 μg/ml enabled highest transduction efficiency.

Abbreviations: Merck Buffer: 5 mM Tris pH 8.0, 75 mM NaCl, 5% Sucrose, 0.005% Polysorbate 80, 1 mM $MgCl_2$; all further additions are formulated in Merck Buffer; Chitosan: 1%, Mannitol: 1 M; Protamine: 10 μg/ml protamine sulfate, Pluronic F68: 0.001%; Blended: a blend of Sucrose, Mannitol and Pluronic F68. Merck-buffer indicates the basic formulation without supporting transfectant additives. Presence of CAR is indicated by sufficient transduction at low multiplicity of infection (MOI, infectious viral particles per target cell). In the absence of CAR, uptake is achieved only by low affinity uptake via integrin-mediated uptake. The effect without additive is illustrated in RT-4 (approx. 25% transduction at MOI 100) versus CT-26 (<5% transduction at MOI 5000). Addition of 10 μg/ml protamine sulfate doubles transduction in RT-4 and triples it in CT-26.

A cooperative adjuvant effect of protamine sulfate was also found in the ex vivo tissue culture (see FIG. 12). Tumor and bladder tissues were transduced with $10^8$ ivp Im02 or Ad0 (empty adenoviral vector) with or without addition of 10 μg/ml protamine sulfate. Transgene expression and IFN-γ expression as response cytokine was measured at day 6 after transduction in the culture supernatant by ELISA. In the presence of 10 μg/ml protamine sulfate, the expression of the response cytokine IFN-γ is higher at even lower transgene expression, which suggests that Im02 in the presence of protamine sulfate stimulates more immune cells.

Based on results on the panel of cell lines and the evaluation of target cell condition, this formulation was applied in the ex vivo therapy simulation study.

Example 11: Transgene Expression of 4-1BBL, IL-2, and scIL-12 of Im02 and of Single-Gene Expressing Vectors at Different MOI, and IFN-γ Response Transgene expression of 4-1BBL, IL-2 and scIL-12 and IFN-γ response of Im02, and combinations of single-gene expressing vectors reveal that IFN-γ expression is dependent on increasing 4-1BBL levels.

Human A549-cells were transduced for one hour with Im02 or combinations of single-gene adenoviral vectors expressing scIL-12, IL-2, and 4-1BBL, respectively, at multiplicities of infection (MOI, i.e., infectious viral particles per target cell) as indicated by numbers in brackets (see FIG. 19). Human peripheral blood mononuclear cells (PBMCs) were added 4 hours after transduction and supernatants were collected for cytokine assays after 34 hours of co-culture. Cytokine levels were detected by ELISA. Tumor cells were detached and cells positive for 4-1BBL were detected by flow cytometry. Indicated data points are the mean of four individual donors, each with four replicates.

As shown in FIG. 19, single-gene vectors expressing IL-12, IL-2, and 4-1BBL alone at MOI [5] lead to induction of basic levels of up to 4.2 ng/ml IFN-γ. A combination of IL-12 and IL-2 does not significantly increase this level. Combinations of constant levels of IL-12 and IL-2, both at MOI [5], with increasing levels of 4-1BBL up to MOI [100], lead to increasing IFN-γ induction at moderate IL-12 levels.

It is important to note that the IL-12 expression must not be increased unlimitedly as expressed by the vector Im01 described in Example 3 (see FIG. 3). High IL-12 expression is considered to induce down-regulation of immune activation and to cause toxicity. This condition of high IFN-γ and moderate IL-12 expression is fulfilled by the vector of the present disclosure, in particular by the arrangement of 4-1BBL, IL-2, and IL-12 shown in vector Im02.

The invention claimed is:

1. A method of treating cancer comprising administering to a subject in need thereof a therapeutically effective amount of a pharmaceutical composition comprising a vector, wherein the vector comprises the nucleotide sequence of SEQ ID NO: 12, which comprises nucleic acid sequences encoding 4-1BB ligand (4-1BBL), single chain IL-12 (scIL-12) and IL-2, and wherein the administration is intratumoral administration.

2. The method of claim 1, wherein the vector is any one of an adenoviral vector, an adeno-associated virus vector, a lentiviral vector, a herpes simplex virus vector, a pox virus vector, an RNA vector, a plasmid vector, a nanoparticle vector, and naked DNA.

3. The method of claim 1, wherein the cancer is any one of bladder cancer, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, cervical hyperplasia, neuroblastoma, rhabdomyosarcoma, Kaposi's sarcoma, Hodgkin's disease, non-Hodgkin's lymphoma, soft-tissue sarcoma, mesothelioma, osteogenic sarcoma, primary macro-globulinemia, and retinoblastoma.

4. The method of claim 1, wherein the method is a method of treating cancer metastasis.

* * * * *

SEQUENCE LISTING

```
<160> NUMBER OF SEQ ID NOS: 12

<210> SEQ ID NO 1
<211> LENGTH: 765
<212> TYPE: DNA
<213> ORGANISM: Homo sapiens

<400> SEQUENCE: 1
atggaatacg cctctgacgc ttcactggac cccgaagccc cgtggcctcc cgcgccccgc      60
gctcgcgcct gccgcgtact gccttgggcc ctggtcgcgg ggctgctgct gctgctgctg     120
ctcgctgccg cctgcgccgt cttcctcgcc tgcccctggg ccgtgtccgg ggctcgcgcc     180
tcgcccggct ccgcggccag cccgagactc cgcgagggtc ccgagctttc gcccgacgat     240
```

```
cccgccggcc tcttggacct gcggcagggc atgtttgcgc agctggtggc ccaaaatgtt    300
ctgctgatcg atgggcccct gagctggtac agtgacccag gcctggcagg cgtgtccctg    360 acgggggggcc tgagctacaa agaggacacg aaggagctgg tggtggccaa ggctggagtc    420
tactatgtct tctttcaact agagctgcgg cgcgtggtgg ccggcgaggg ctcaggctcc    480
gtttcacttg cgctgcacct gcagccactg cgctctgctg ctggggccgc cgccctggct    540
ttgaccgtgg acctgccacc cgcctcctcc gaggctcgga actcggcctt cggtttccag    600
ggccgcttgc tgcacctgag tgccggccag cgcctgggcg tccatcttca cactgaggcc    660
agggcacgcc atgcctggca gcttacccag ggcgccacag tcttgggact cttccgggtg    720 accccccgaaa tcccagccgg actcccttca ccgaggtcgg aataa    765
```

<210> SEQ ID NO 2
<211> LENGTH: 254
<212> TYPE: PRT
<213> ORGANISM: Homo sapiens

<400> SEQUENCE: 2

```
Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Ala Ala Cys Ala Val Phe
            35                  40                  45

Leu Ala Cys Pro Trp Ala Val Ser Gly Ala Arg Ala Ser Pro Gly Ser
50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250
```

<210> SEQ ID NO 3
<211> LENGTH: 462
<212> TYPE: DNA
<213> ORGANISM: Homo sapiens

<400> SEQUENCE: 3

```
atgtacagga tgcaactcct gtcttgcatt gcactaagtc ttgcacttgt cacaaacagt      60
gcacctactt caagttctac aaagaaaaca cagctacaac tggagcattt actgctggat    120
ttacagatga ttttgaatgg aattaataat tacaagaatc ccaaactcac caggatgctc    180
acatttaagt tttacatgcc aagaaggcc acagaactga acatcttca gtgtctagaa      240
gaagaactca aacctctgga ggaagtgcta aatttagctc aaagcaaaaa ctttcactta    300
agacccaggg acttaatcag caatatcaac gtaatagttc tggaactaaa gggatctgaa    360
acaacattca tgtgtgaata tgctgatgag acagcaacca ttgtagaatt tctgaacaga    420
tggattacct tttgtcaaag catcatctca acactgactt ga                      462
```

<210> SEQ ID NO 4
<211> LENGTH: 153
<212> TYPE: PRT
<213> ORGANISM: Homo sapiens

<400> SEQUENCE: 4

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 5
<211> LENGTH: 1623
<212> TYPE: DNA
<213> ORGANISM: Artificial Sequence
<220> FEATURE:
<223> OTHER INFORMATION: Nucleotide sequence of human single-chain IL-12

<400> SEQUENCE: 5

```
atgtgtcacc agcagttggt catctcttgg ttttccctgg ttttctggc atctcccctc     60
gtggccatat gggaactgaa gaaagatgtt tatgtcgtag aattggattg gtatccggat   120
gcccctggag aaatggtggt cctcacctgt gacacccctg aagaagatgg tatcacctgg   180
accttggacc agagcagtga ggtcttaggc tctggcaaaa ccctgaccat ccaagtcaaa   240
gagtttggag atgctggcca gtacacctgt cacaaaggag cgaggttct aagccattcg   300
ctcctgctgc ttcacaaaaa ggaagatgga atttggtcca ctgatatttt aaaggaccag   360
```

-continued

```
aaagaaccca aaaataagac ctttctaaga tgcgaggcca agaattattc tggacgtttc    420
acctgctggt ggctgacgac aatcagtact gatttgacat tcagtgtcaa aagcagcaga    480
ggctcttctg accccaagg ggtgacgtgc ggagctgcta cactctctgc agagagagtc     540
agagggaca acaaggagta tgagtactca gtggagtgcc aggaggacag tgcctgccca     600
gctgctgagg agagtctgcc cattgaggtc atggtggatg ccgttcacaa gctcaagtat    660
gaaaactaca ccagcagctt cttcatcagg acatcatca aacctgaccc acccaagaac     720
ttgcagctga agccattaaa gaattctcgg caggtggagg tcagctggga gtaccctgac    780
acctggagta ctccacattc ctacttctcc ctgacattct gcgttcaggt ccagggcaag    840
agcaagagag aaaagaaaga tagagtcttc acggacaaga cctcagccac ggtcatctgc    900
cgcaaaaatg ccagcattag cgtgcgggcc caggaccgct actatagctc atcttggagc    960
gaatgggcat ctgtgccctg cagtggtggc ggtggaagcg gcggtggcgg aagcggcggt   1020
ggcggcagca gaaccctccc cgtggccact ccagacccag gaatgttccc atgccttcac   1080
cactcccaaa acctgctgag ggccgtcagc aacatgctcc agaaggccag acaaactcta   1140
gaattttacc cttgcacttc tgaagagatt gatcatgaag atatcacaaa agataaaacc   1200
agcacagtgg aggcctgttt accattggaa ttaaccaaga atgagagttg cctaaattcc   1260
agagagacct ctttcataac taatgggagt tgcctggcct ccagaaagac ctcttttatg   1320
atggccctgt gccttagtag tatttatgaa gacttgaaga tgtaccaggt ggagttcaag   1380
accatgaatg caaagcttct gatggatcct aagaggcaga tctttctaga tcaaaacatg   1440
ctggcagtta ttgatgagct gatgcaggcc ctgaatttca acagtgagac tgtgccacaa   1500
aaatcctccc ttgaagaacc ggattttat aaaactaaaa tcaagctctg catacttctt   1560
catgctttca gaattcgggc agtgactatt gatagagtga tgagctatct gaatgcttcc   1620
taa                                                                 1623
```

<210> SEQ ID NO 6
<211> LENGTH: 540
<212> TYPE: PRT
<213> ORGANISM: Artificial Sequence
<220> FEATURE:
<223> OTHER INFORMATION: Amino acid sequence of human single-chain IL-12

<400> SEQUENCE: 6

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
```

```
            130                 135                 140
Leu Thr Thr Ile Ser Thr Asp Leu Thr Phe Ser Val Lys Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Gly Ser Gly Gly Gly
                325                 330                 335

Gly Ser Gly Gly Gly Ser Arg Asn Leu Pro Val Ala Thr Pro Asp
            340                 345                 350

Pro Gly Met Phe Pro Cys Leu His His Ser Gln Asn Leu Leu Arg Ala
        355                 360                 365

Val Ser Asn Met Leu Gln Lys Ala Arg Gln Thr Leu Glu Phe Tyr Pro
    370                 375                 380

Cys Thr Ser Glu Glu Ile Asp His Glu Asp Ile Thr Lys Asp Lys Thr
385                 390                 395                 400

Ser Thr Val Glu Ala Cys Leu Pro Leu Glu Leu Thr Lys Asn Glu Ser
                405                 410                 415

Cys Leu Asn Ser Arg Glu Thr Ser Phe Ile Thr Asn Gly Ser Cys Leu
            420                 425                 430

Ala Ser Arg Lys Thr Ser Phe Met Met Ala Leu Cys Leu Ser Ser Ile
        435                 440                 445

Tyr Glu Asp Leu Lys Met Tyr Gln Val Glu Phe Lys Thr Met Asn Ala
    450                 455                 460

Lys Leu Leu Met Asp Pro Lys Arg Gln Ile Phe Leu Asp Gln Asn Met
465                 470                 475                 480

Leu Ala Val Ile Asp Glu Leu Met Gln Ala Leu Asn Phe Asn Ser Glu
                485                 490                 495

Thr Val Pro Gln Lys Ser Ser Leu Glu Glu Pro Asp Phe Tyr Lys Thr
            500                 505                 510

Lys Ile Lys Leu Cys Ile Leu Leu His Ala Phe Arg Ile Arg Ala Val
        515                 520                 525

Thr Ile Asp Arg Val Met Ser Tyr Leu Asn Ala Ser
    530                 535                 540

<210> SEQ ID NO 7
```

<211> LENGTH: 987
<212> TYPE: DNA
<213> ORGANISM: Homo sapiens

<400> SEQUENCE: 7

```
atgtgtcacc agcagttggt catctcttgg tttccctgg tttttctggc atctcccctc    60
gtggccatat gggaactgaa gaaagatgtt tatgtcgtag aattggattg gtatccggat   120
gcccctggag aaatggtggt cctcacctgt gacacccctg aagaagatgg tatcacctgg   180
accttggacc agagcagtga ggtcttaggc tctggcaaaa ccctgaccat ccaagtcaaa   240
gagtttggag atgctggcca gtacacctgt cacaaaggag gcgaggttct aagccattcg   300
ctcctgctgc ttcacaaaaa ggaagatgga atttggtcca ctgatatttt aaaggaccag   360
aaagaaccca aaaataagac ctttctaaga tgcgaggcca agaattattc tggacgtttc   420
acctgctggt ggctgacgac aatcagtact gatttgacat tcagtgtcaa agcagcaga   480
ggctcttctg acccccaagg ggtgacgtgc ggagctgcta cactctctgc agagagagtc   540
agagggaca acaaggagta tgagtactca gtggagtgcc aggaggacag tgcctgccca   600
gctgctgagg agagtctgcc cattgaggtc atggtggatg ccgttcacaa gctcaagtat   660
gaaaactaca ccagcagctt cttcatcagg gacatcatca acctgacccc acccaagaac   720
ttgcagctga agccattaaa gaattctcgg caggtggagg tcagctggga gtaccctgac   780
acctggagta ctccacattc ctacttctcc ctgacattct gcgttcaggt ccagggcaag   840
agcaagagag aaaagaaaga tagagtcttc acggacaaga cctcagccac ggtcatctgc   900
cgcaaaaatg ccagcattag cgtgcgggcc caggaccgct actatagctc atcttggagc   960
gaatgggcat ctgtgccctg cagttag                                      987
```

<210> SEQ ID NO 8
<211> LENGTH: 328
<212> TYPE: PRT
<213> ORGANISM: Homo sapiens

<400> SEQUENCE: 8

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
```

165                 170                 175
Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 9
<211> LENGTH: 762
<212> TYPE: DNA
<213> ORGANISM: Homo sapiens

<400> SEQUENCE: 9
atgtggcccc ctgggtcagc ctcccagcca ccgccctcac ctgccgcggc cacaggtctg      60
catccagcgg ctcgccctgt gtccctgcag tgccggctca gcatgtgtcc agcgcgcagc     120
ctcctccttg tggctaccct ggtcctcctg gaccacctca gtttggccag aaacctcccc     180
gtggccactc cagacccagg aatgttccca tgccttcacc actcccaaaa cctgctgagg     240
gccgtcagca acatgctcca gaaggccaga caaactctag aattttaccc ttgcacttct     300
gaagagattg atcatgaaga tatcacaaaa gataaaacca gcacagtgga ggcctgttta     360
ccattggaat taaccaagaa tgagagttgc taaattccag agagacctct tcataact      420
aatgggagtt gcctggcctc agaaagacc tcttttatga tggccctgtg ccttagtagt     480
atttatgaag acttgaagat gtaccaggtg gagttcaaga ccatgaatgc aaagcttctg     540
atggatccta agaggcagat ctttctagat caaaacatgc tggcagttat tgatgagctg     600
atgcaggccc tgaatttcaa cagtgagact gtgccacaaa atcctccct tgaagaaccg     660
gatttttata aaactaaaat caagctctgc atacttcttc atgctttcag aattcgggca     720
gtgactattg atagagtgat gagctatctg aatgcttcct aa                       762

<210> SEQ ID NO 10
<211> LENGTH: 253
<212> TYPE: PRT
<213> ORGANISM: Homo sapiens

<400> SEQUENCE: 10

Met Trp Pro Pro Gly Ser Ala Ser Gln Pro Pro Pro Ser Pro Ala Ala
1               5                   10                  15

Ala Thr Gly Leu His Pro Ala Ala Arg Pro Val Ser Leu Gln Cys Arg
            20                  25                  30

```
Leu Ser Met Cys Pro Ala Arg Ser Leu Leu Val Ala Thr Leu Val
            35                  40                  45

Leu Leu Asp His Leu Ser Leu Ala Arg Asn Leu Pro Val Ala Thr Pro
 50                  55                  60

Asp Pro Gly Met Phe Pro Cys Leu His His Ser Gln Asn Leu Leu Arg
 65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
            115                 120                 125

Ser Cys Leu Asn Ser Arg Glu Thr Ser Phe Ile Thr Asn Gly Ser Cys
130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
            195                 200                 205

Glu Thr Val Pro Gln Lys Ser Ser Leu Glu Glu Pro Asp Phe Tyr Lys
            210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250

<210> SEQ ID NO 11
<211> LENGTH: 7845
<212> TYPE: DNA
<213> ORGANISM: Artificial Sequence
<220> FEATURE:
<223> OTHER INFORMATION: Nucleotide sequence of the shuttle vector hu
      pE1.1

<400> SEQUENCE: 11
ttaacatcat caataatata ccttattttg gattgaagcc aatatgataa tgagggggtg      60
gagtttgtga cgtggcgcgg ggcgtgggaa cggggcgggt gacgtagtag tgtgcggaa     120 gtgtgatgtt gcaagtgtgg cggaacacat gtaagcgacg gatgtggcaa aagtgacgtt     180
tttggtgtgc gccggtgtac acaggaagtg acaattttcg cgcggtttta ggcggatgtt     240
gtagtaaatt tgggcgtaac cgagtaagat ttggccattt tcgcgggaaa actgaataag     300
aggaagtgaa atctgaataa ttttgtgtta ctcatagcgc gtaatatttg tctaggagga     360
tcttctagac ccgggagcgg ccggccgctg tcgaccgtaa ctataacggt cctaaggtag     420
cgaaccacgt caggtcgagt gttcatgaat ggaagatatc tgcgccctag cgccggcgag     480
ctctagtaat caattacggg gtcattagtt catagcccat atatggagtt ccgcgttaca     540
taacttacgg taaatggccc gcctggctga ccgcccaacg accccgccc attgacgtca     600 ataatgacgt atgttcccat agtaacgcca atagggactt tccattgacg tcaatgggtg     660
gagtatttac ggtaaactgc ccacttggca gtacatcaag tgtatcatat gccaagtacg     720
ccccctattg acgtcaatga cggtaaatgg cccgcctggc attatgccca gtacatgacc     780
```

```
ttatgggact ttcctacttg gcagtacatc tacgtattag tcatcgctat taccatggtg      840
atgcggtttt ggcagtacat caatgggcgt ggatagcggt ttgactcacg ggatttccca     900
agtctccacc ccattgacgt caatgggagt ttgttttggc accaaaatca acgggacttt     960
ccaaaatgtc gtaacaactc cgccccattg acgcaaatgg gcggtaggcg tgtacggtgg    1020
gaggtctata taagcagagc tggtttagtg aaccgtcaga tccgctagac ggaccgacca    1080
tggaatacgc ctctgacgct tcactggacc ccgaagcccc gtggcctccc gcgcccgcg     1140 ctcgcgcctg ccgcgtactg ccttgggccc tggtcgcggg gctgctgctg ctgctgctgc    1200
tcgctgccgc ctgcgccgtc ttcctcgcct gccctgggc cgtgtccggg gctcgcgcct     1260
cgcccggctc cgcggccagc ccgagactcc gcgagggtcc cgagctttcg cccgacgatc    1320
ccgccggcct cttggacctg cggcagggca tgtttgcgca gctggtggcc caaaatgttc    1380
tgctgatcga tgggcccctg agctggtaca gtgacccagg cctggcaggc gtgtccctga    1440 cgggggggcct gagctacaaa gaggacacga aggagctggt ggtggccaag gctggagtct    1500
actatgtctt ctttcaacta gagctgcggc gcgtggtggc cggcgagggc tcaggctccg    1560
tttcacttgc gctgcacctg cagccactgc gctctgctgc tggggccgcc gccctggctt    1620
tgaccgtgga cctgccaccc gcctcctccg aggctcggaa ctcggccttc ggtttccagg    1680
gccgcttgct gcacctgagt gccggccagc gcctgggcgt ccatcttcac actgaggcca    1740
gggcacgcca tgcctggcag cttacccagg gcgccacagt cttgggactc ttccgggtga    1800
cccccgaaat cccagccgga ctcccttcac cgaggtcgga ataagaacgc tagctcttgt    1860
gactggcgcg cctgatcaat cgatgtttaa acgttatttt ccaccatatt gccgtctttt    1920
ggcaatgtga gggcccggaa acctggccct gtcttcttga cgagcattcc tagggggtctt   1980 tcccctctcg ccaaaggaat gcaaggtctg ttgaatgtcg tgaaggaagc agttcctctg    2040
gaagcttctt gaagacaaac aacgtctgta gcgacccttt gcaggcagcg gaaccccca    2100 cctggcgaca ggtgcctctg cggccaaaag ccacgtgtat aagatacacc tgcaaaggcg    2160
gcacaacccc agtgcgacgt tgtgagttgg atagttgtgg aaagagtcaa atggctctcc    2220
tcaagcgtat tcaacaaggg gctgaaggat gcccagaagg tacccccatg tatgggatct    2280
gatctggggc ctcggtgcac atgctttacg tgtgtttagt cgaggttaaa aaaacgtcta    2340
ggccccccga accacgggga cgtggttttc ctttgaaaaa cacgattctc gagactagtc    2400
gtacgaccat gtacaggatg caactcctgt cttgcattgc actaagtctt gcacttgtca    2460
caaacagtgc acctacttca agttctacaa agaaaacaca gctacaactg gagcatttac    2520
tgctggattt acagatgatt ttgaatggaa ttaataatta caagaatccc aaactcacca    2580
ggatgctcac atttaagttt tacatgccca agaaggccac agaactgaaa catcttcagt    2640
gtctagaaga agaactcaaa cctctggagg aagtgctaaa tttagctcaa agcaaaaact    2700
ttcacttaag acccagggac ttaatcagca atatcaacgt aatagttctg gaactaaagg    2760
gatctgaaac aacattcatg tgtgaatatg ctgatgagac agcaaccatt gtagaatttc    2820
tgaacagatg gattacctt tgtcaaagca tcatctcaac actgacttga acgcgtgcta    2880
gcaggcccgg ccgccttgt taagacagg atgaagctta aaacagctct ggggttgtac      2940
ccaccccaga ggcccacgtg gcggctagta ctccggtatt gcggtaccct tgtacgcctg    3000
ttttatactc ccttcccgta acttagacgc acaaaaccaa gttcaataga aggggtaca    3060 aaccagtacc accacgaaca agcacttctg tttccccggt gatgtcgtat agactgcttg    3120
```

```
cgtggttgaa agcgacggat ccgttatccg cttatgtact tcgagaagcc cagtaccacc    3180
tcggaatctt cgatgcgttg cgctcagcac tcaaccccag agtgtagctt aggctgatga    3240
gtctggacat ccctcaccgg tgacggtggt ccaggctgcg ttggcggcct acctatggct    3300
aacgccatgg gacgctagtt gtgaacaagg tgtgaagagc ctattgagct acataagaat    3360
cctccggccc ctgaatgcgg ctaatcccaa cctcggagca ggtggtcaca aaccagtgat    3420
tggcctgtcg taacgcgcaa gtccgtggcg gaaccgacta ctttgggtgt ccgtgtttcc    3480
ttttatttta ttgtggctgc ttatggtgac aatcacagat tgttatcata aagcgaattg    3540
gattgcgtac gcggaccgaa ctagtttcgc cgcctccaac atgtgtcacc agcagttggt    3600
catctcttgg ttttccctgg tttttctggc atctcccctc gtggccatat gggaactgaa    3660
gaaagatgtt tatgtcgtag aattggattg gtatccggat gccctggag aaatggtggt     3720 cctcacctgt gacacccctg aagaagatgg tatcacctgg accttggacc agagcagtga    3780
ggtcttaggc tctggcaaaa ccctgaccat ccaagtcaaa gagtttggag atgctggcca    3840
gtacacctgt cacaaaggag gcgaggttct aagccattcg ctcctgctgc ttcacaaaaa    3900
ggaagatgga atttggtcca ctgatatttt aaaggaccag aaagaaccca aaaataagac    3960 cttttctaaga tgcgaggcca agaattattc tggacgtttc acctgctggt ggctgacgac    4020
aatcagtact gatttgacat tcagtgtcaa aagcagcaga ggctcttctg acccccaagg    4080
ggtgacgtgc ggagctgcta cactctctgc agagagagtc agaggggaca caaggagta    4140 tgagtactca gtggagtgcc aggaggacag tgcctgccca gctgctgagg agagtctgcc    4200
cattgaggtc atggtggatg ccgttcacaa gctcaagtat gaaaactaca ccagcagctt    4260
cttcatcagg gacatcatca aacctgaccc acccaagaac ttgcagctga agccattaaa    4320
gaattctcgg caggtggagg tcagctggga gtaccctgac acctggagta ctccacattc    4380
ctacttctcc ctgacattct gcgttcaggt ccagggcaag agcaagagag aaaagaaaga    4440
tagagtcttc acgacaagaa cctcagccac ggtcatctgc cgcaaaaatg ccagcattag    4500
cgtgcgggcc caggaccgct actatagctc atcttggagc gaatgggcat ctgtgccctg    4560
cagtggtggc ggtggaagcg gcggtggcgg aagcggcggt ggcggcagca gaaacctccc    4620
cgtggccact ccagacccag gaatgttccc atgccttcac cactcccaaa acctgctgag    4680
ggccgtcagc aacatgctcc agaaggccag acaaactcta gaatttttacc cttgcacttc    4740 tgaagagatt gatcatgaag atatcacaaa agataaaacc agcacagtgg aggcctgttt    4800
accattggaa ttaaccaaga atgagagttg cctaaattcc agagagacct ctttcataac    4860
taatgggagt tgcctggcct ccagaaagac ctctttatg atggccctgt gccttagtag    4920
tatttatgaa gacttgaaga tgtaccaggt ggagttcaag accatgaatg caaagcttct    4980
gatggatcct aagaggcaga tctttctaga tcaaaacatg ctggcagtta ttgatgagct    5040
gatgcaggcc ctgaatttca cagtgagac tgtgccacaa aaatcctccc ttgaagaacc    5100
ggatttttat aaaactaaaa tcaagctctg catacttctt catgctttca gaattcgggc    5160
agtgactatt gatagagtga tgagctatct gaatgcttcc taaaaaccgg cccggccggc    5220
cccgcggccg ctcgagccta agcttctaga taagatatcc gatccaccgg atctagataa    5280
ctgatcataa tcagccatac cacatttgta gaggttttac ttgctttaaa aaacctccca    5340
cacctccccc tgaacctgaa acataaaatg aatgcaattg ttgttgttaa cttgtttatt    5400
gcagcttata atggttacaa ataaagcaat agcatcacaa atttcacaaa taaagcattt    5460
ttttcactgc attctagttg tggtttgtcc aaactcatca atgtatctta gcgccggcgg    5520
```

```
gtcgacagcc tagtggtacc cacgaggtgg caggagctgc atcgatgtcg cttcctcgct   5580
cactgactcg ctgcgctcgg tcgttcggct gcggcgagcg gtatcagctc actcaaaggc   5640
ggtaatacgg ttatccacag aatcaggggga taacgcagga agaacatgt gagcaaaagg    5700 ccagcaaaag gccaggaacc gtaaaaaggc cgcgttgctg gcgttttcc ataggctccg    5760 cccccctgac gagcatcaca aaaatcgacg ctcaagtcag aggtggcgaa acccgacagg   5820
actataaaga taccaggcgt ttccccctgg aagctccctc gtgcgctctc ctgttccgac   5880
cctgccgctt accggatacc tgtccgcctt tctcccttcg ggaagcgtgg cgctttctca   5940
tagctcacgc tgtaggtatc tcagttcggt gtaggtcgtt cgctccaagc tgggctgtgt   6000
gcacgaaccc cccgttcagc ccgaccgctg cgccttatcc ggtaactatc gtcttgagtc   6060
caacccggta agacacgact tatcgccact ggcagcagcc actggtaaca ggattagcag   6120
agcgaggtat gtaggcggtg ctacagagtt cttgaagtgg tggcctaact acggctacac   6180
tagaaggaca gtatttggta tctgcgctct gctgaagcca gttaccttcg gaaaaagagt   6240
tggtagctct tgatccggca aacaaaccac cgctggtagc ggtggttttt ttgtttgcaa   6300
gcagcagatt acgcgcagaa aaaaaggatc tcaagaagat cctttgatct tttctacggg   6360
gtctgacgct cagtggaacg aaaactcacg ttaagggatt ttggtcatga gattatcaaa   6420
aaggatcttc acctagatcc ttttaaatta aaaatgaagt tttaaatcaa tctaaagtat   6480
atatgagtaa acttggtctg acagttacca atgcttaatc agtgaggcac ctatctcagc   6540
gatctgtcta tttcgttcat ccatagttgc ctgactcccc acagtggcc agagactgca    6600 ttcgaaaacg tttgaattga taattattat catttgcggg tcaattctta gaaaaactca   6660
tcgagcatca aatgaaactg caatttattc atatcaggat tatcaatacc atattttga    6720 aaaagccgtt tctgtaatga aggagaaaac tcaccgaggc agttccatag gattgcaaga   6780
tcctggtatc ggtctgcgat tccgactcgt ccaacatcaa tacaacctat taatttcccc   6840
tcgtcaaaaa taaggttatc aagtgagaaa tcaccatgag tgacgactga atccggtgag   6900
aatggcaaaa gcttatgcat ttctttccag acttgttcaa caggccagcc attacgctcg   6960
tcatcaaaat cactcgcatc aaccaaaccg ttattcattc gtgattgcgc ctgagcgaga   7020
cgaaatacgc gatcgctgtt aaaaggacaa ttacaaacag gaatcgaatg caaccggcgc   7080
aggaacactg ccagcgcatc aacaatattt tcacctgaat caggatattc ttctaatacc   7140
tggaatgctg ttttcccggg gatcgcagtg gtgagtaacc atgcatcatc aggagtacgg   7200
ataaaatgct tgatggtcgg aagaggcata aattccgtca gccagtttag tctgaccatc   7260
tcatctgtaa catcattggc aacgctacct ttgccatgtt tcagaaacaa ctctggcgca   7320
tcgggcttcc catacaatcg atagattgtc gcacctgatt gcccgacatt atcgcgagcc   7380
catttatacc catataaatc agcatccatg ttggaattta atcgcggcct cgagcaagac   7440
gtttcccgtt gaatatggct cataacaccc cttgtattac tgtttatgta agcagacagt   7500
tttattgttc atgcgaaaac gtttgaattg ataattatta tcatttgcgg gtcctttccg   7560
gcgatccgcc ttgttacggg gcggcgacct cgcgggtttt cgctatttat gaaaattttc   7620
cggtttaagg cgtttccgtt cttcttcgtc ataacttaat gttttatttt aaaataccct   7680
ctgaaaagaa aggaaacgac agctgaaagc gagcttttg gcctctgtcg tttcctttct   7740
ctgtttttgt ccgtggaatg aacaatggaa gtcggcctcg tgatacgcct attttttatag   7800 gttaatgtca tgataataat ggtttcttag cgatatttaa attaa                    7845
```

<210> SEQ ID NO 12
<211> LENGTH: 5545
<212> TYPE: DNA
<213> ORGANISM: Artificial Sequence
<220> FEATURE:
<223> OTHER INFORMATION: Nucleotide sequence of the expression cassette comprising CMV, human 4-1BBL, EMCV IRES, human IL-2, PV IRES, human scIL-12, and SV40polyA as contained in hu pE1.1

<400> SEQUENCE: 12

```
taacatcatc aataatatac cttattttgg attgaagcca atatgataat gagggggtgg      60
agtttgtgac gtggcgcggg gcgtgggaac ggggcgggtg acgtagtagt gtggcggaag     120
tgtgatgttg caagtgtggc ggaacacatg taagcgacgg atgtggcaaa agtgacgttt     180
ttggtgtgcg ccggtgtaca caggaagtga caattttcgc gcggttttag gcggatgttg     240
tagtaaattt gggcgtaacc gagtaagatt tggccatttt cgcgggaaaa ctgaataaga     300
ggaagtgaaa tctgaataat tttgtgttac tcatagcgcg taatatttgt ctagggagat     360
cttctagacc cggagcggc cggccgctgt cgaccgtaac tataacggtc ctaaggtagc     420
gaaccacgtc aggtcgagtg ttcatgaatg aagatatct gcgccctagc gccggcgagc     480
tctagtaatc aattacgggg tcattagttc atagcccata tatggagttc cgcgttacat     540
aacttacggt aaatggcccg cctggctgac cgcccaacga ccccgccca ttgacgtcaa     600 taatgacgta tgttcccata gtaacgccaa tagggacttt ccattgacgt caatgggtgg     660
agtatttacg gtaaactgcc cacttggcag tacatcaagt gtatcatatg ccaagtacgc     720
cccctattga cgtcaatgac ggtaaatggc ccgcctggca ttatgcccag tacatgacct     780
tatgggactt tcctacttgg cagtacatct acgtattagt catcgctatt accatggtga     840
tgcggttttg gcagtacatc aatgggcgtg atagcggtt tgactcacgg ggatttccaa     900
gtctccaccc cattgacgtc aatgggagtt tgttttggca ccaaaatcaa cgggactttc     960
caaaatgtcg taacaactcc gccccattga cgcaaatggg cggtaggcgt gtacggtggg    1020
aggtctatat aagcagagct ggtttagtga accgtcagat ccgctagacg gaccgaccat    1080
ggaatacgcc tctgacgctt cactggaccc cgaagcccg tggcctcccg cgccccgcgc    1140
tcgcgcctgc cgcgtactgc cttgggccct ggtcgcgggg ctgctgctgc tgctgctgct    1200 cgctgccgc tgcgccgtct tcctcgcctg ccctgggcc gtgtccgggg ctcgcgcctc    1260
gcccggctcc gcggccagcc cgagactccg cgagggtccc gagctttcgc ccgacgatcc    1320
cgccggcctc ttggacctgc ggcagggcat gtttgcgcag ctggtggccc aaaatgttct    1380
gctgatcgat gggcccctga gctggtacag tgacccaggc ctggcaggcg tgtccctgac    1440 gggggggcctg agctacaaag aggacacgaa ggagctggtg gtggccaagg ctggagtcta    1500
ctatgtcttc tttcaactag agctgcggcg cgtggtggcc ggcgagggct caggctccgt    1560
ttcacttgcg ctgcacctgc agccactgcg ctctgctgct ggggccgcg ccctggcttt    1620 gaccgtggac ctgccacccg cctcctccga ggctcggaac tcggccttcg gtttccaggg    1680
ccgcttgctg cacctgagtg ccggccagcg cctgggcgtc atcttcaca ctgaggccag    1740 ggcacgccat gcctggcagc ttacccaggg cgccacagtc ttgggactct ccgggtgac    1800 ccccgaaatc ccagccggac tcccttcacc gaggtcggaa taagaacgct agctcttgtg    1860
actggcgcgc ctgatcaatc gatgtttaaa cgttattttc caccatattg ccgtcttttg    1920
gcaatgtgag ggcccggaaa cctggccctg tcttcttgac gagcattcct aggggtcttt    1980
cccctctcgc caaaggaatg caaggtctgt tgaatgtcgt gaaggaagca gttcctctgg    2040
```

```
aagcttcttg aagacaaaca acgtctgtag cgacccttg caggcagcgg aaccccccac    2100
ctggcgacag gtgcctctgc ggccaaaagc cacgtgtata agatacacct gcaaaggcgg    2160
cacaacccca gtgcgacgtt gtgagttgga tagttgtgga aagagtcaaa tggctctcct    2220
caagcgtatt caacaagggg ctgaaggatg cccagaaggt accccattgt atgggatctg    2280
atctggggcc tcggtgcaca tgctttacgt gtgtttagtc gaggttaaaa aaacgtctag    2340 gcccccccgaa ccacggggac gtggttttcc tttgaaaaac acgattctcg agactagtcg    2400
tacgaccatg tacaggatgc aactcctgtc ttgcattgca ctaagtcttg cacttgtcac    2460
aaacagtgca cctacttcaa gttctacaaa gaaaacacag ctacaactgg agcatttact    2520
gctggattta cagatgattt tgaatggaat taataattac aagaatccca aactcaccag    2580
gatgctcaca tttaagtttt acatgcccaa gaaggccaca gaactgaaac atcttcagtg    2640
tctagaagaa gaactcaaac ctctggagga agtgctaaat ttagctcaaa gcaaaaactt    2700
tcacttaaga cccagggact taatcagcaa tatcaacgta atagttctgg aactaaaggg    2760
atctgaaaca acattcatgt gtgaatatgc tgatgagaca gcaaccattg tagaatttct    2820
gaacagatgg attaccttt gtcaaagcat catctcaaca ctgacttgaa cgcgtgctag    2880
caggcccggc cggccttgtt aaagacagga tgaagcttaa aacagctctg gggttgtacc    2940 cacccccagag gcccacgtgg cggctagtac tccggtattg cggtacccttt gtacgcctgt    3000 tttatactcc cttcccgtaa cttagacgca caaaaccaag ttcaatagaa gggggtacaa    3060
accagtacca ccacgaacaa gcacttctgt tccccggtg atgtcgtata gactgcttgc    3120
gtggttgaaa gcgacggatc cgttatccgc ttatgtactt cgagaagccc agtaccacct    3180
cggaatcttc gatgcgttgc gctcagcact caacccccaga gtgtagctta ggctgatgag    3240
tctggacatc cctcaccggt gacggtggtc caggctgcgt tggcggccta cctatggcta    3300
acgccatggg acgctagttg tgaacaaggt gtgaagagcc tattgagcta cataagaatc    3360
ctccggcccc tgaatgcggc taatcccaac ctcggagcag gtggtcacaa accagtgatt    3420
ggcctgtcgt aacgcgcaag tccgtggcgg aaccgactac tttgggtgtc cgtgtttcct    3480
tttattttat tgtggctgct tatggtgaca atcacagatt gttatcataa agcgaattgg    3540
attgcgtacg cggaccgaac tagtttcgcc gcctccaaca tgtgtcacca gcagttggtc    3600
atctcttggt tttccctggt ttttctggca tctcccctcg tggccatatg ggaactgaag    3660
aaagatgttt atgtcgtaga attggattgg tatccggatg cccctggaga atggtggtc    3720 ctcacctgtg acaccctga agaagatggt atcacctgga ccttggacca gagcagtgag    3780
gtcttaggct ctggcaaaac cctgaccatc caagtcaaag agtttggaga tgctggccag    3840
tacacctgtc acaaggagg cgaggttcta agccattcgc tcctgctgct tcacaaaaag    3900
gaagatggaa tttggtccac tgatatttta aaggaccaga agaacccaa aaataagacc    3960 tttctaagat gcgaggccaa gaattattct ggacgtttca cctgctggtg gctgacgaca    4020
atcagtactg atttgacatt cagtgtcaaa agcagcagag gctcttctga cccccaaggg    4080
gtgacgtgcg gagctgctac actctctgca gagagagtca gagggacaa caaggagtat    4140 gagtactcag tggagtgcca ggaggacagt gcctgcccag ctgctgagga gagtctgccc    4200
attgaggtca tggtggatgc cgttcacaag ctcaagtatg aaaactacac cagcagcttc    4260
ttcatcaggg acatcatcaa acctgaccca cccaagaact tgcagctgaa gccattaaag    4320
aattctcggc aggtggaggt cagctgggag tacctgaca cctggagtac tccacattcc    4380
```

```
tacttctccc tgacattctg cgttcaggtc cagggcaaga gcaagagaga aaagaaagat    4440
agagtcttca cggacaagac ctcagccacg gtcatctgcc gcaaaaatgc cagcattagc    4500
gtgcgggccc aggaccgcta ctatagctca tcttggagcg aatgggcatc tgtgccctgc    4560
agtggtggcg gtggaagcgg cggtggcgga agcggcggtg gcggcagcag aaacctcccc    4620
gtggccactc cagacccagg aatgttccca tgccttcacc actcccaaaa cctgctgagg    4680
gccgtcagca acatgctcca gaaggccaga caaactctag aattttaccc ttgcacttct    4740
gaagagattg atcatgaaga tatcacaaaa gataaaacca gcacagtgga ggcctgttta    4800
ccattggaat taaccaagaa tgagagttgc ctaaattcca gagagacctc tttcataact    4860
aatgggagtt gcctggcctc cagaaagacc tcttttatga tggccctgtg ccttagtagt    4920
atttatgaag acttgaagat gtaccaggtg gagttcaaga ccatgaatgc aaagcttctg    4980
atggatccta agaggcagat ctttctagat caaaacatgc tggcagttat tgatgagctg    5040
atgcaggccc tgaatttcaa cagtgagact gtgccacaaa aatcctccct tgaagaaccg    5100 gattttata aaactaaaat caagctctgc atacttcttc atgctttcag aattcgggca    5160
gtgactattg atagagtgat gagctatctg aatgcttcct aaaaaccggc ccggccggcc    5220
ccgcggccgc tcgagcctaa gcttctagat aagatatccg atccaccgga tctagataac    5280
tgatcataat cagccatacc acatttgtag aggttttact tgctttaaaa aacctcccac    5340
acctccccct gaacctgaaa cataaaatga atgcaattgt tgttgttaac ttgtttattg    5400
cagcttataa tggttacaaa taaagcaata gcatcacaaa tttcacaaat aaagcatttt    5460
tttcactgca ttctagttgt ggtttgtcca aactcatcaa tgtatcttag cgccggcggg    5520
tcgacagcct agtggtaccc acgag                                          5545
```